(12) United States Patent (10) Patent No.: US 7,435,549 B1
Kufer et al. (45) Date of Patent: Oct. 14, 2008

(54) METHOD OF IDENTIFYING BINDING SITE DOMAINS THAT RETAIN THE CAPACITY OF BINDING TO AN EPITOPE

(75) Inventors: Peter Kufer, Moosburg (DE); Tobias Raum, Munich (DE); Katrin Borschert, Munich (DE); Florian Zettl, Kempten (DE); Ralf Lutterbuse, Munich (DE)

(73) Assignee: Micromet AG, Munich (DE)

( * ) Notice: Subject to any disclaimer, the term of this patent is extended or adjusted under 35 U.S.C. 154(b) by 0 days.

(21) Appl. No.: 09/554,465

(22) PCT Filed: Nov. 16, 1998

(86) PCT No.: PCT/EP98/07313

§ 371 (c)(1),
(2), (4) Date: Oct. 19, 2000

(87) PCT Pub. No.: WO99/25818

PCT Pub. Date: May 27, 1999

(30) Foreign Application Priority Data

Nov. 17, 1997 (EP) .................................. 97120096

(51) Int. Cl.
*G01N 33/53* (2006.01)
(52) U.S. Cl. ..................... 435/7.1; 435/7.2; 435/328; 530/387.2; 530/387.3; 424/133; 424/134
(58) Field of Classification Search ................. 435/7.1, 435/7.2, 172.3, 328; 530/387.2, 387.3; 424/134, 424/133.1
See application file for complete search history.

(56) References Cited

U.S. PATENT DOCUMENTS

| 5,225,539 | A |   | 7/1993  | Winter et al.      |           |
|-----------|---|---|---------|--------------------|-----------|
| 5,837,242 | A | * | 11/1998 | Holliger et al.    | 424/136.1 |
| 6,027,930 | A | * | 2/2000  | Borrebaeck         | 435/235.1 |
| 6,551,592 | B2| * | 4/2003  | Lindhofer et al.   | 424/136.1 |
| 6,667,150 | B1| * | 12/2003 | Rudert et al.      | 435/5     |

FOREIGN PATENT DOCUMENTS

WO  WO-95/25167  9/1995

OTHER PUBLICATIONS

See Paul, Fundamental Immunology, (textbook), 1999, under the heading Immunoglobulins: Structure and Function, , pp. 37, 43, 58, 59.*
Janeway et al. eds. Immunobiology 1999, third edition, section 3-6 and 3-7.*
Rudikoff et al., Proc. Natl Acad Sci USA (1982) vol. 79 p. 1979.*
Current Opinion in Immunology 9(1997); 201-12 Hayden et al "Antibody . . . ".
The Journal of Immunology 158(1997), 3965-70 Mack et al "Biologic . . . ".
Nature Biotechnology 14(Sep. 1996), 1149-54 McGuinness et al "Phage . . . ".
Proc. Natl. Acad. Sci. USA 92(Jul. 1995) 7021-25 Mack et al. "A small . . . ".
TIBTECH 12(May 1994) 173-84 Clackson et al "In vitro selection from . . . ".
Proc. Natl. Acad. Sci. USA 88(Sep. 1991), 7978-82 Barbas et al.
Int. J. Cancer 38(1986), 47-53 Gottlinger et al "The epithelial cell . . . ".
Kabat, Elvin A. et al., "Sequences of Proteins of Immunological Interest," NIH, 1991, pp. xiv-xvii.
Kufer, P. et al.; "Construction and biological activity of a recombinant bispecific single-chain antibody desgined for therapy of minimal residual colorectal cancer", Cancer Immunol Immunother., 1997, vol. 45, pp. 193-197.
Gunneriusson, Elin et al., "Surface display of a functional single-chain Fv antibody on staphylococci", Journal of Bacteriology, Mar. 1996, vol. 178, No. 5, pp. 1341-1346.

* cited by examiner

*Primary Examiner*—Lone V. Le
*Assistant Examiner*—Jacob Cheu
(74) *Attorney, Agent, or Firm*—Birch, Stewart, Kolasch & Birch, LLP

(57) ABSTRACT

The present invention relates to a method of identifying binding site domains that retain the capacity of binding to an epitope when positioned C-terminal of at least one further domain in a recombinant bi- or multivalent polypeptide. The present invention further relates to a kit comprising components such as panels of recombinant vectors of bacterial libraries transfected with a panel of recombinant vectors which is useful in carrying out the method of the invention. Furthermore, binding site domains and fusion proteins obtainable by the method of the invention as well as antibody-like molecules comprising such domains and proteins are described. Furthermore, pharmaceutical and diagnostic compositions containing the above-described fusion proteins and polypeptides are provided.

47 Claims, 40 Drawing Sheets

Figure 4:
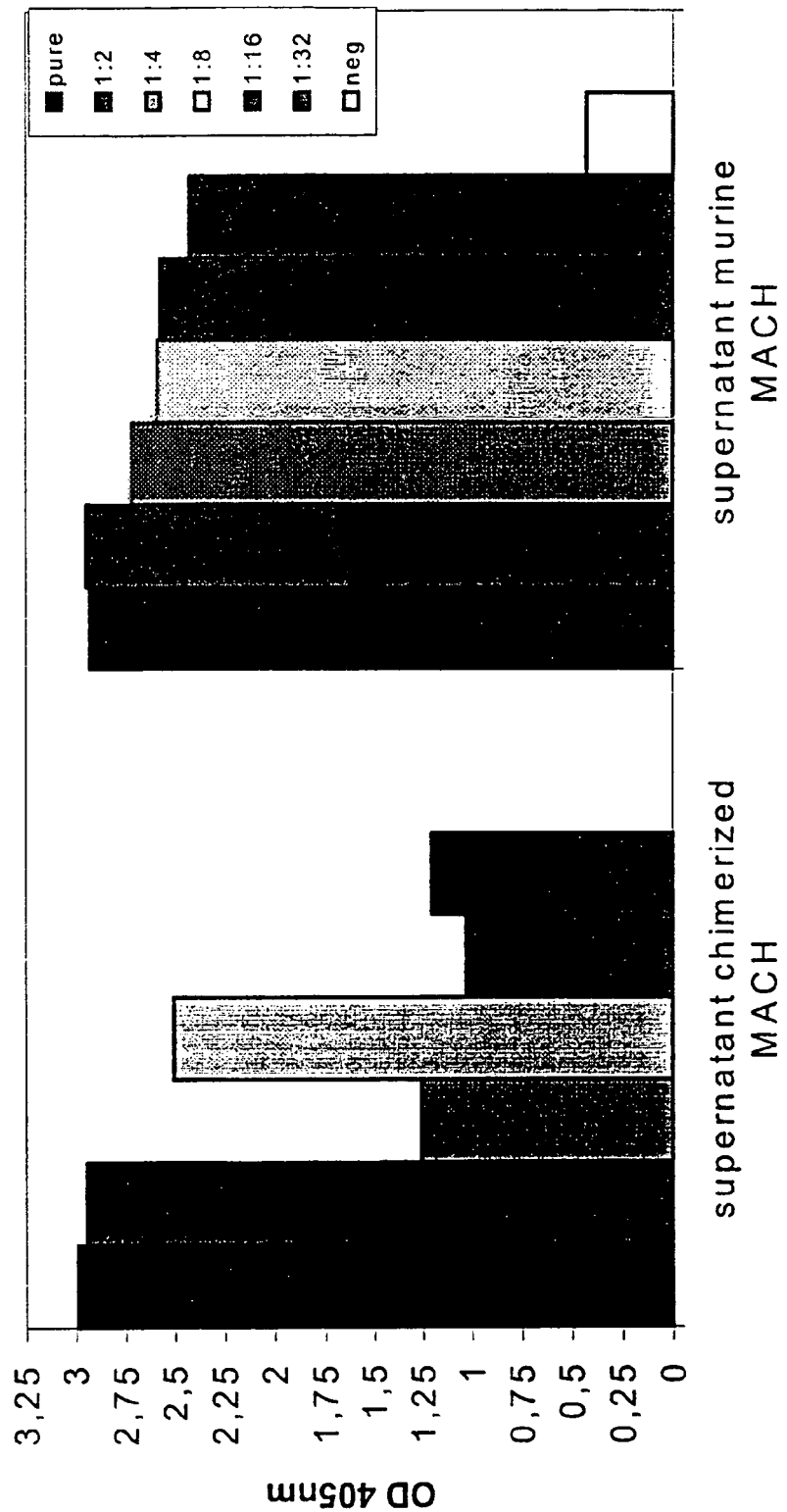

Figure 1.1
Recombinant bifunctional single-chain protein
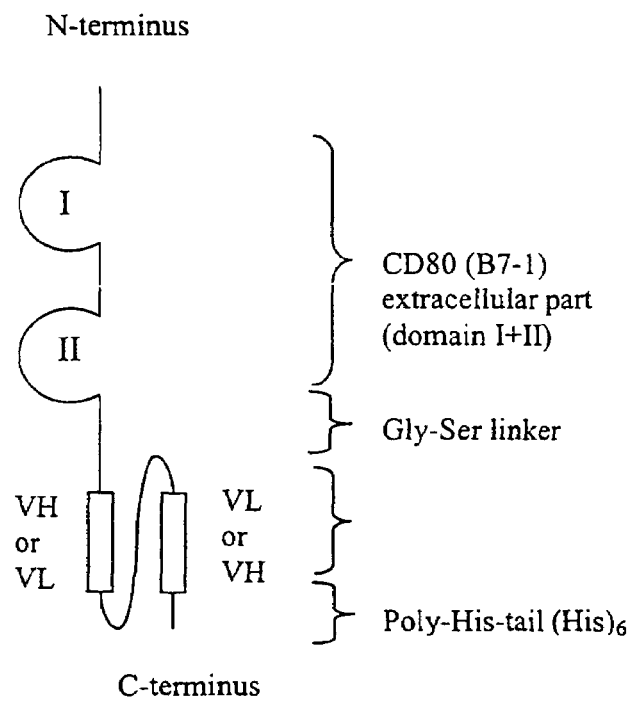
Figure 1.2 DNA-sequence designated CTI
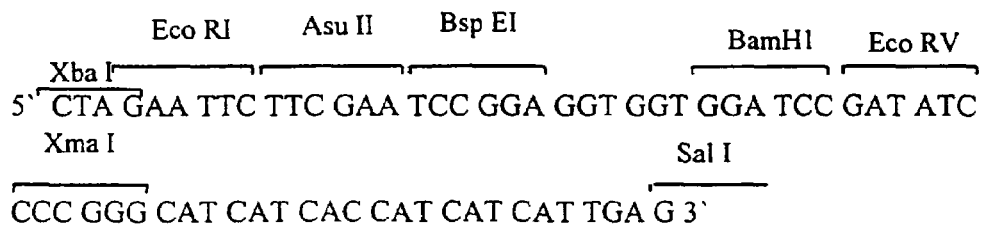

Figure 1.3 Design of various bifunctional CD80-scFv-constructs
Figure 1.3.1.
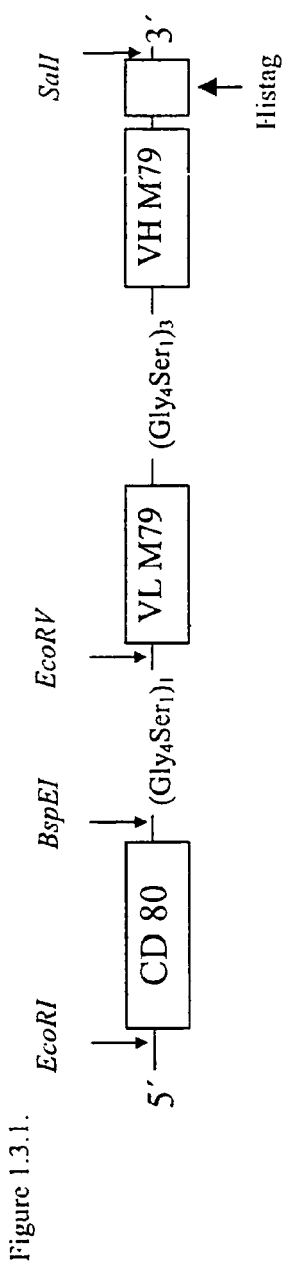
Figure 1.3.2.
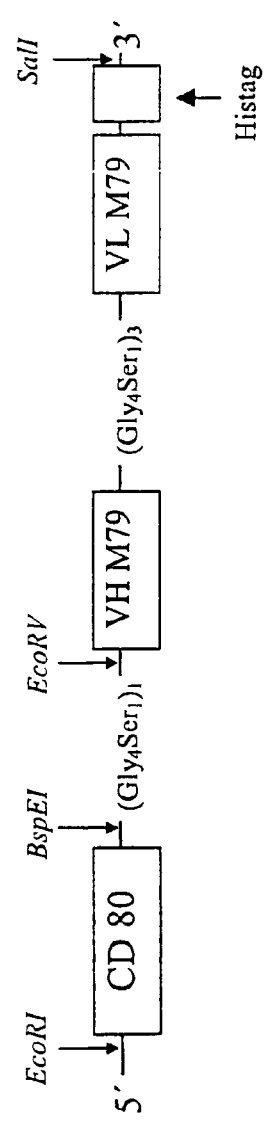
Figure 1.3.3.
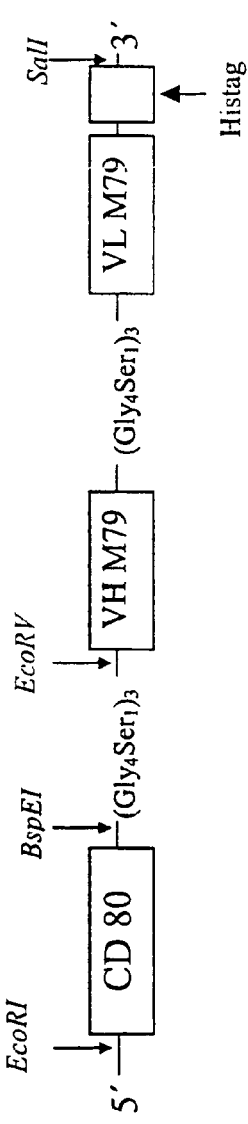

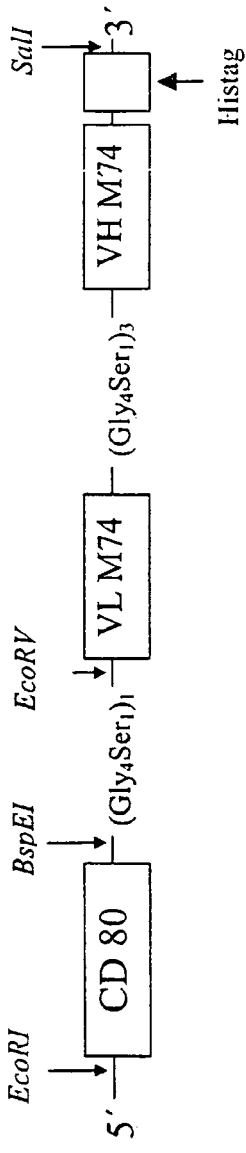
Figure 1.3.4.
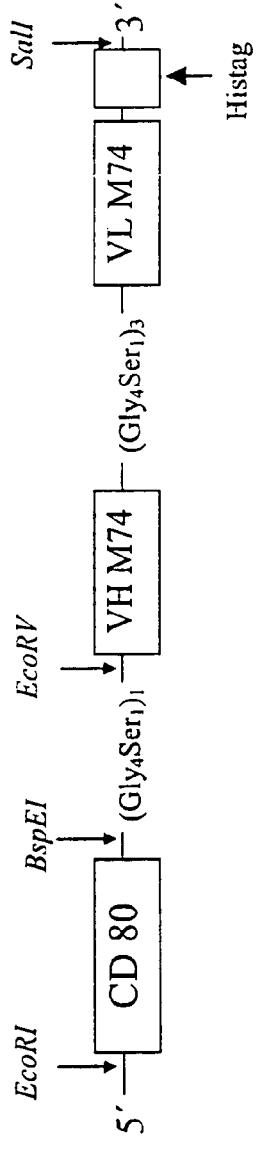
Figure 1.3.5.
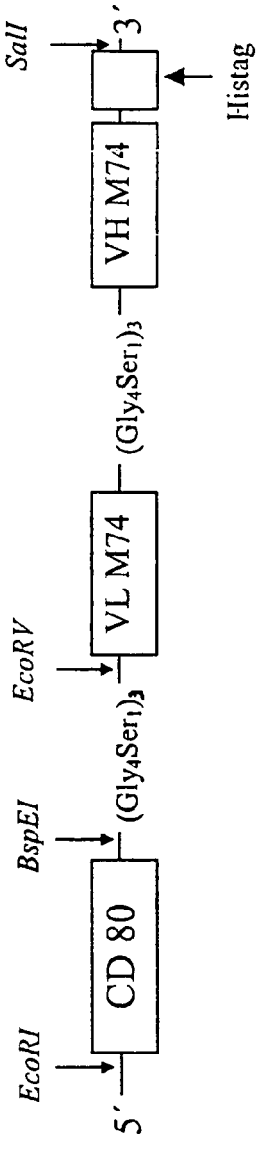
Figure 1.3.6.

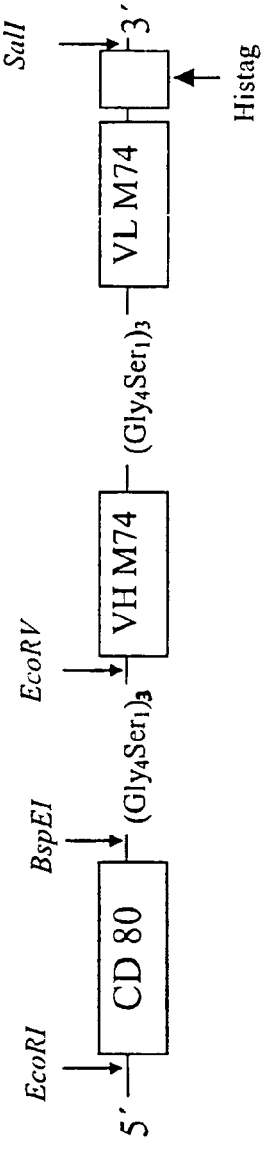
Figure 1.3.7
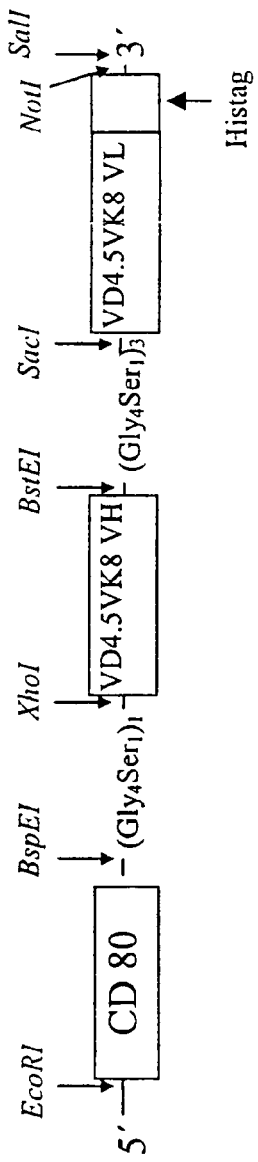
Figure 1.3.8.
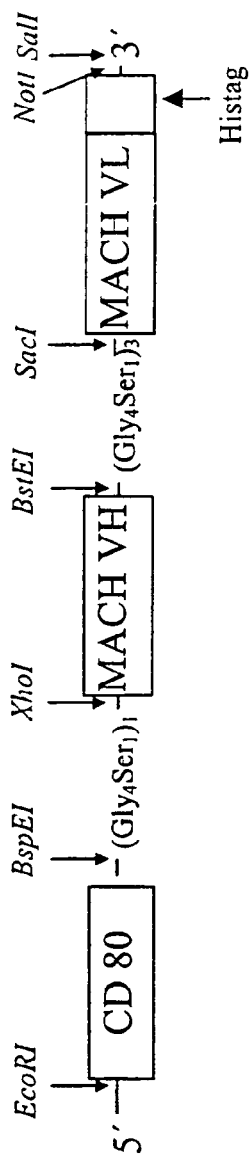
Figure 1.3.9.

Figure 1.4
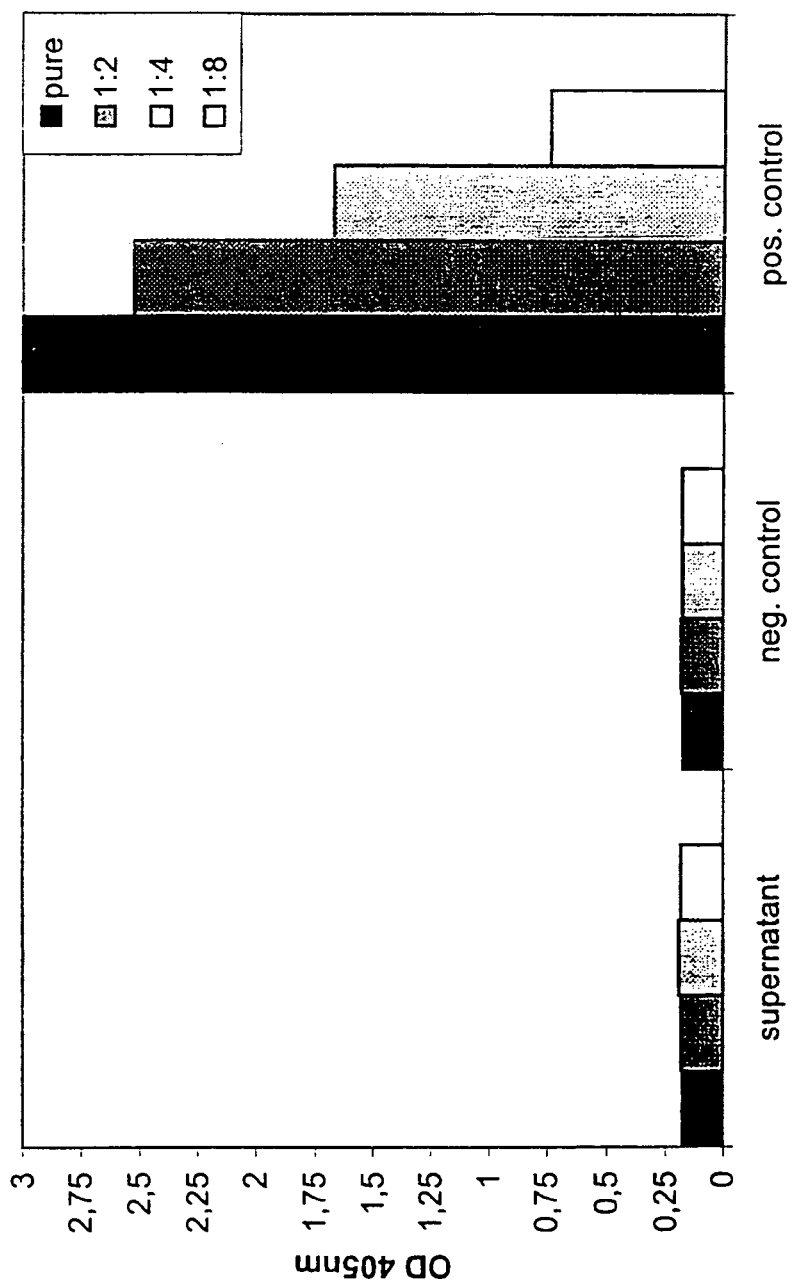

Figure 1.5
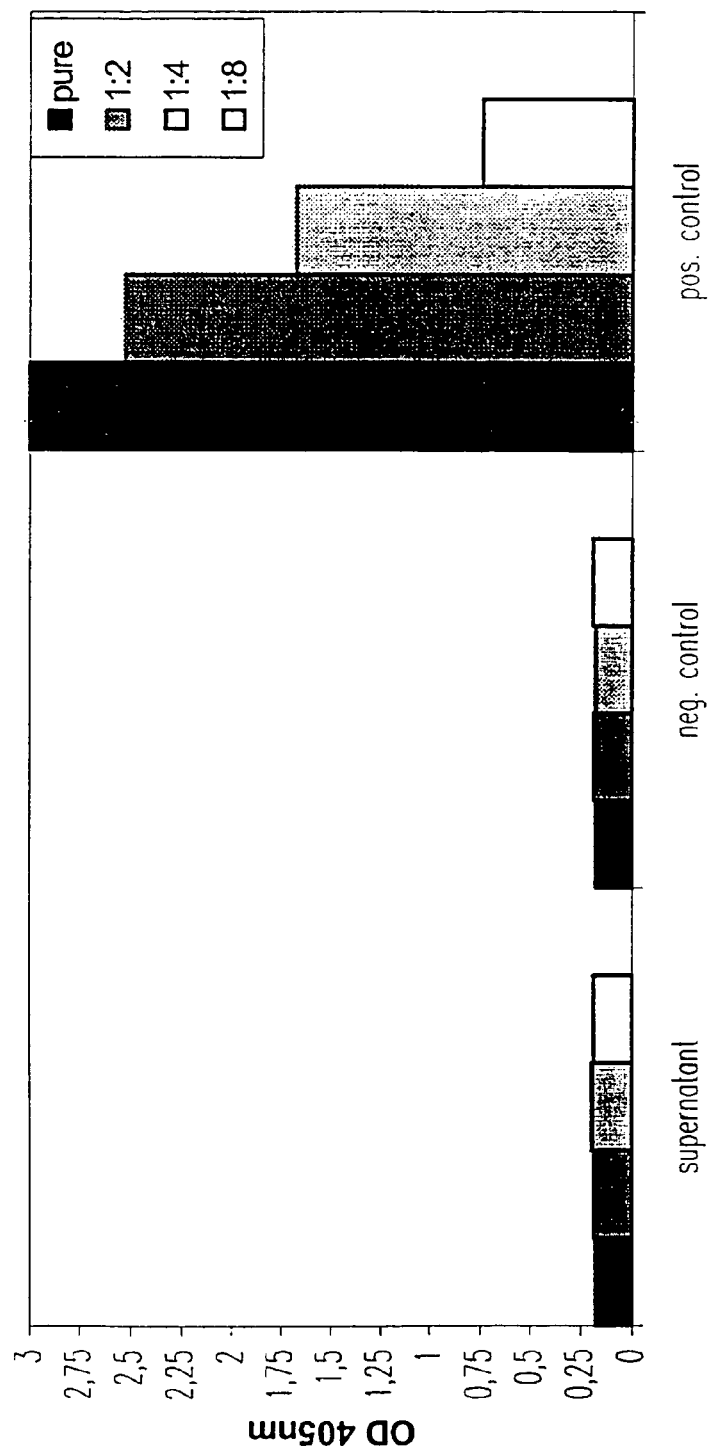

Figure 1.6
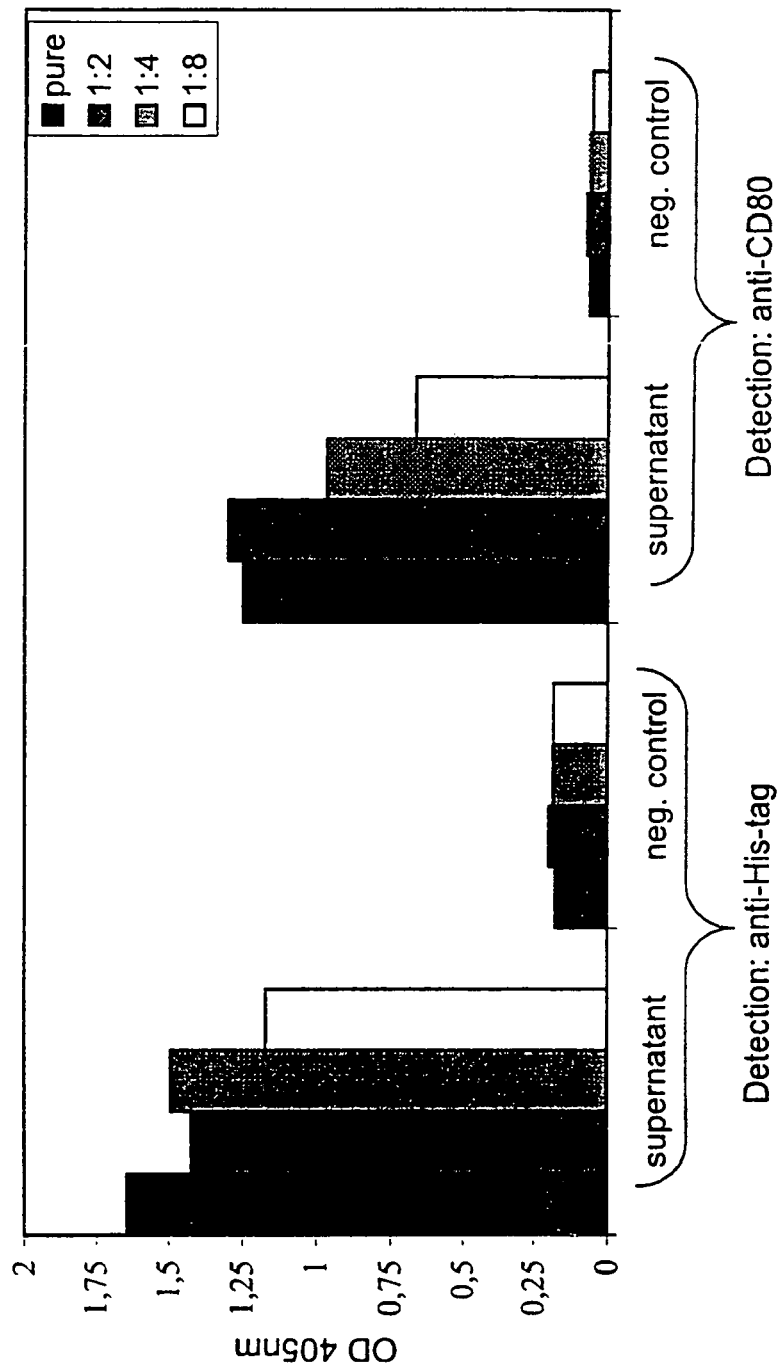

Figure 1.7
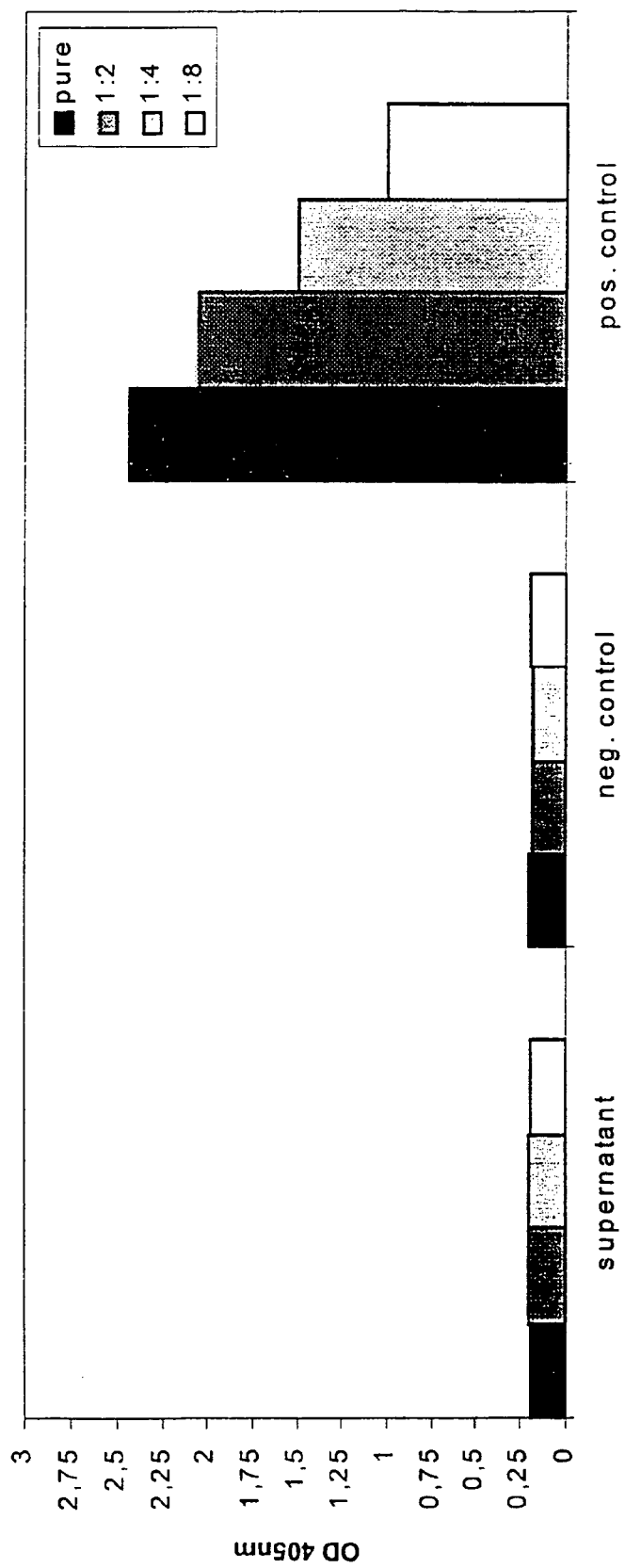

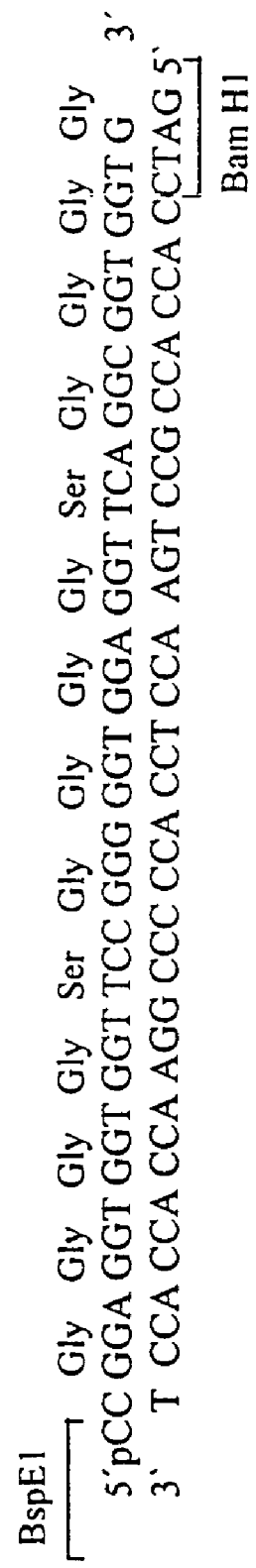
Figure 1.8 DNA-sequence of double-stranded oligonucleotide designated ACCGS15BAM Figure 1.9
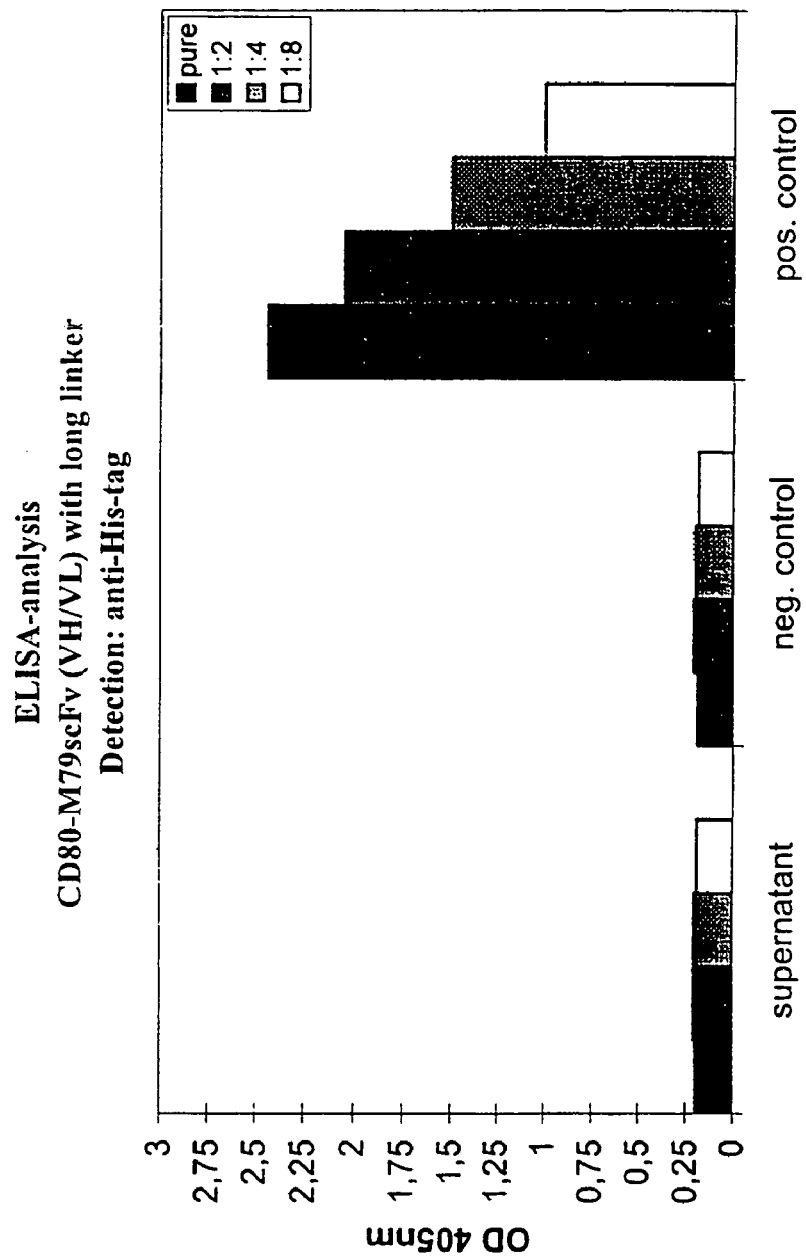

Figure 2.1
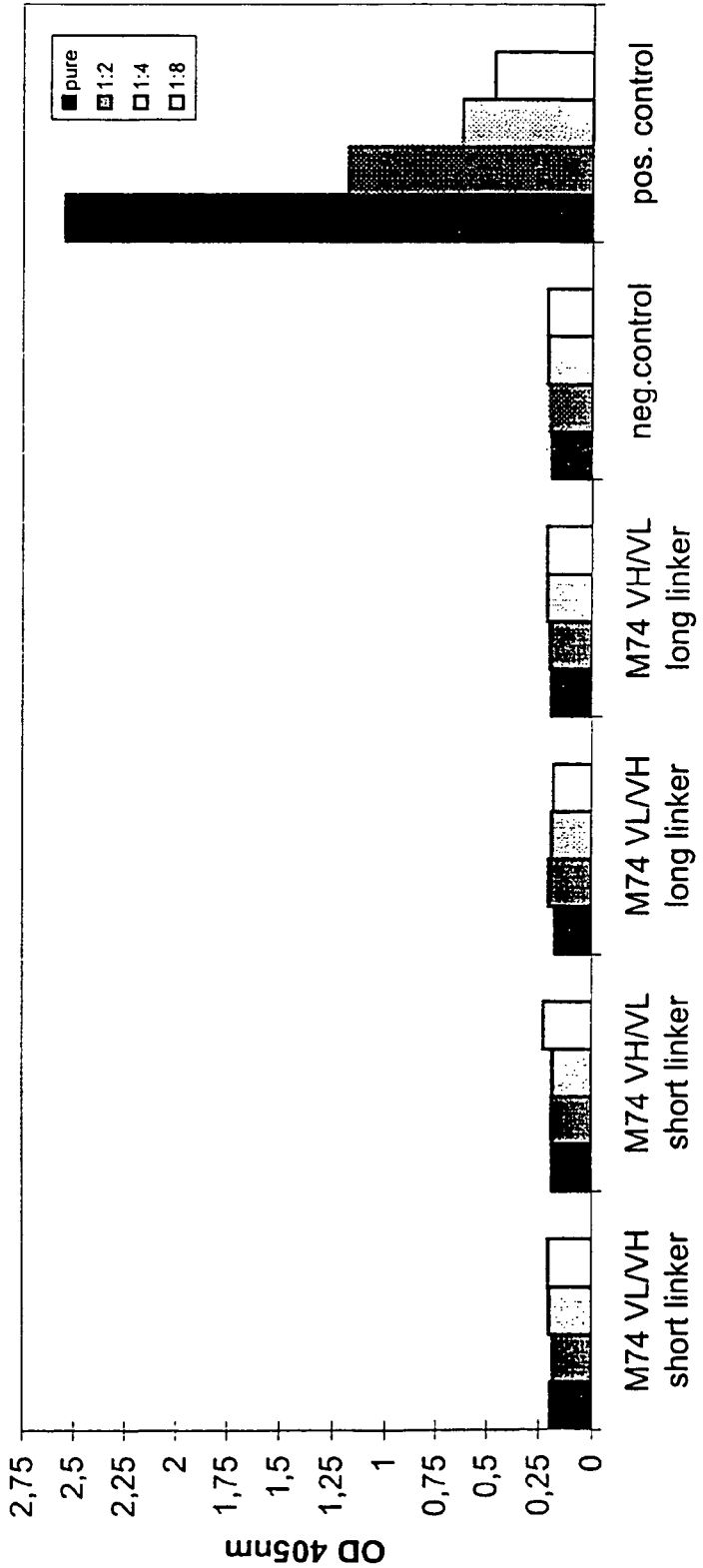

Figure 2.2
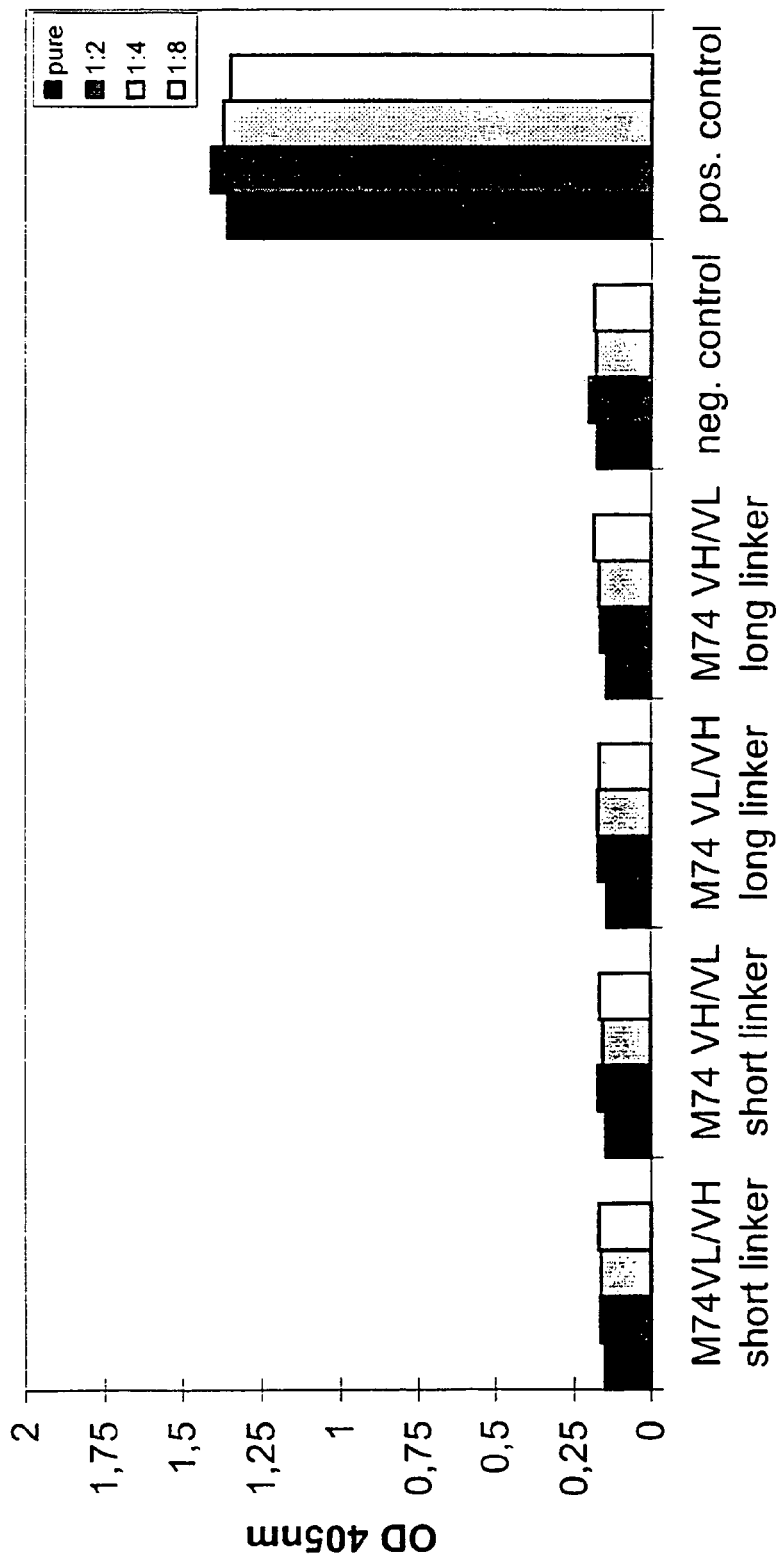

Figure 3.1

```
              9              18             27             36             45             54
5' GAG GTG CAG CTG CTC GAG TCT GGG GGA GGC GTG GTC CAG CCT GGG AGG TCC CTG
   --- --- --- --- --- --- --- --- --- --- --- --- --- --- --- --- --- ---
    E   V   Q   L   L   E   S   G   G   G   V   V   Q   P   G   R   S   L 63             72             81             90             99            108
   AGA CTC TCC TGT GCA GCC TCT GGA TTC ACC TTC AGT AGC TAT GGC ATG CAC TGG
   --- --- --- --- --- --- --- --- --- --- --- --- --- --- --- --- --- ---
    R   L   S   C   A   A   S   G   F   T   F   S   S   Y   G   M   H   W 117            126            135            144            153            162
   GTC CGC CAG GCT CCA GGC AAG GGG CTG GAG TGG GTG GCA GTT ATA TCA TAT GAT
   --- --- --- --- --- --- --- --- --- --- --- --- --- --- --- --- --- ---
    V   R   Q   A   P   G   K   G   L   E   W   V   A   V   I   S   Y   D 171            180            189            198            207            216
   GGA AGT AAT AAA TAC TAT GCA GAC TCC GTG AAG GGC CGA TTC ACC ATC TCC AGA
   --- --- --- --- --- --- --- --- --- --- --- --- --- --- --- --- --- ---
    G   S   N   K   Y   Y   A   D   S   V   K   G   R   F   T   I   S   R 225            234            243            252            261            270
   GAC AAT TCC AAG AAC ACG CTG TAT CTG CAA ATG AAC AGC CTG AGA GCT GAG GAC
   --- --- --- --- --- --- --- --- --- --- --- --- --- --- --- --- --- ---
    D   N   S   K   N   T   L   Y   L   Q   M   N   S   L   R   A   E   D 279            288            297            306            315            324
   ACG GCT GTG TAT TAC TGT GCG AAA GAT ATG GGG TGG GGC AGT GGC TGG AGA CCC
   --- --- --- --- --- --- --- --- --- --- --- --- --- --- --- --- --- ---
    T   A   V   Y   Y   C   A   K   D   M   G   W   G   S   G   W   R   P 333            342            351            360            369            378
   TAC TAC TAC TAC GGT ATG GAC GTC TGG GGC CAA GGG ACC ACG GTC ACC GTC TCC
   --- --- --- --- --- --- --- --- --- --- --- --- --- --- --- --- --- ---
    Y   Y   Y   Y   G   M   D   V   W   G   Q   G   T   T   V   T   V   S

TCA  3'
   ---
    S
```

Figure 3.2

```
             9              18             27             36             45             54
5' GAG CTC CAG ATG ACC CAG TCT CCA TCC TCC CTG TCT GCT TCT GTG GGA GAC AGA
   --- --- --- --- --- --- --- --- --- --- --- --- --- --- --- --- --- ---
    E   L   Q   M   T   Q   S   P   S   S   L   S   A   S   V   G   D   R 63             72             81             90             99            108
   GTC ACC ATC ACT TGT CGG ACA AGT CAG AGC ATT AGC AGC TAT TTA AAT TGG TAT
   --- --- --- --- --- --- --- --- --- --- --- --- --- --- --- --- --- ---
    V   T   I   T   C   R   T   S   Q   S   I   S   S   Y   L   N   W   Y 117            126            135            144            153            162
   CAG CAG AAA CCA GGA CAG CCT CCT AAG CTG CTC ATT TAC TGG GCA TCT ACC CGG
   --- --- --- --- --- --- --- --- --- --- --- --- --- --- --- --- --- ---
    Q   Q   K   P   G   Q   P   P   K   L   L   I   Y   W   A   S   T   R 171            180            189            198            207            216
   GAA TCC GGG GTC CCT GAC CGA TTC AGT GGC AGC GGG TCT GGG ACA GAT TTC ACT
   --- --- --- --- --- --- --- --- --- --- --- --- --- --- --- --- --- ---
    E   S   G   V   P   D   R   F   S   G   S   G   S   G   T   D   F   T 225            234            243            252            261            270
   CTC ACC ATC AGC AGT CTA CAA CCT GAA GAT TCT GCA ACT TAC TAC TGT CAG CAG
   --- --- --- --- --- --- --- --- --- --- --- --- --- --- --- --- --- ---
    L   T   I   S   S   L   Q   P   E   D   S   A   T   Y   Y   C   Q   Q 279            288            297            306            315
   AGT TAC GAC ATC CCG TAC ACT TTT GGC CAG GGG ACC AAG CTG GAG ATC AAA 3'
   --- --- --- --- --- --- --- --- --- --- --- --- --- --- --- --- ---
    S   Y   D   I   P   Y   T   F   G   Q   G   T   K   L   E   I   K
```

Figure 3.3
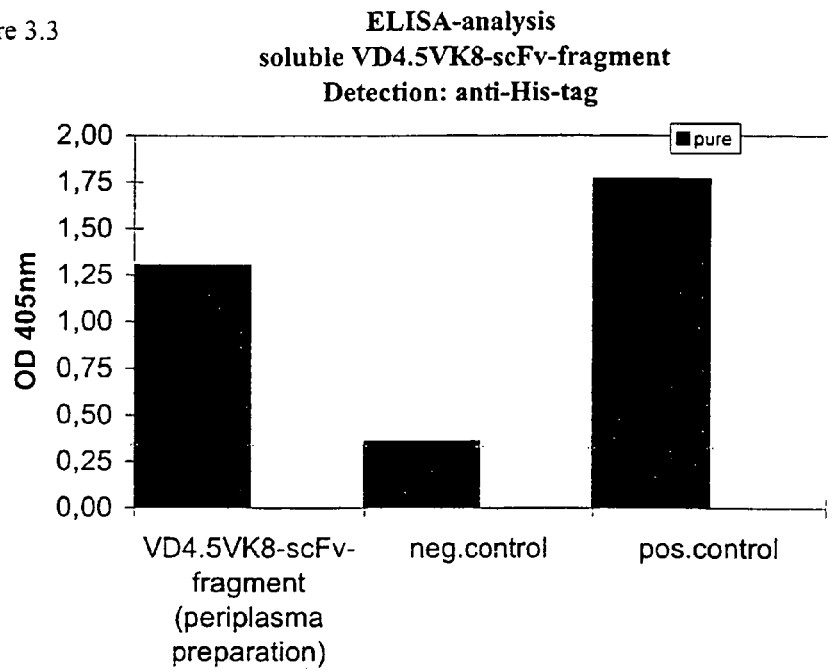
Figure 3.4 DNA-sequence designated L-F-NS3Frame
```
            EcoRI
5' CCG CTC TAG AAT TCC ACC ATG GGA TGG AGC TGT ATC ATC CTC TTC TTG
   GTA GCA ACA GCT ACA GGT GTC CAC TCC GAC TAC AAA GAT GAT GAC GAT
        Eco RV                    Eco 47III        NdeI
   AAG GAT ATC TCC GGA GGT GGT GGT AGC GCT ATT CCA TAT GGA CGT CCC
       XhoI                                    Not I       Xba I
   GCT CGA GGT CGT CCA TCA TCA CCA TCA TCA CTG AGC GGC CGC TCT AGA
       Sal I
   GTC GAC CTC 3'
```

Figure 5.1
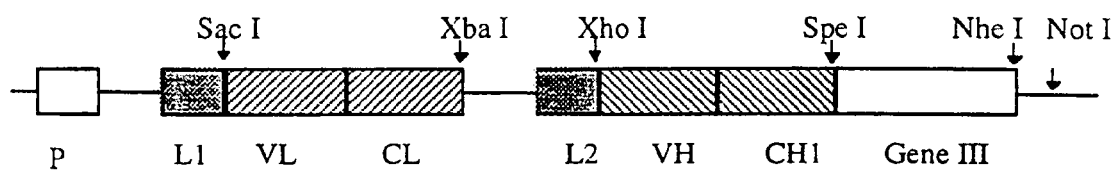

Figure 5.2

```
           destroyed
           SacI        9       SalI    18               27              36              45              54
       5'  GAG CTG    CAG CTG  GTC GAC  ACT AAA CCT CCT GAG TAC GGT GAT ACA CCT ATT CCG
           --- ---    --- ---  --- ---  --- --- --- --- --- --- --- --- --- --- --- ---
                                         T   K   P   P   E   Y   G   D   T   P   I   P 63              72              81              90              99             108
           GGC TAT    ACT TAT ATC AAC  CCT CTC GAC GGC ACT TAT CCG CCT GGT ACT GAG CAA
           --- ---    --- --- --- ---  --- --- --- --- --- --- --- --- --- --- --- ---
            G   Y      T   Y   I   N    P   L   D   G   T   Y   P   P   G   T   E   Q 117             126             135             144             153             162
           AAC CCC    GCT AAT CCT AAT  CCT TCT CTT GAG GAG TCT CAG CCT CTT AAT ACT TTC
           --- ---    --- --- --- ---  --- --- --- --- --- --- --- --- --- --- --- ---
            N   P      A   N   P   N    P   S   L   E   E   S   Q   P   L   N   T   F 171             180             189             198             207             216
           ATG TTT    CAG AAT AAT AGG  TTC CGA AAT AGG CAG GGG GCA TTA ACT GTT TAT ACG
           --- ---    --- --- --- ---  --- --- --- --- --- --- --- --- --- --- --- ---
            M   F      Q   N   N   R    F   R   N   R   Q   G   A   L   T   V   Y   T 225             234             243             252             261             270
           GGC ACT    GTT ACT CAA GGC  ACT GAC CCC GTT AAA ACT TAT TAC CAG TAC ACT CCT
           --- ---    --- --- --- ---  --- --- --- --- --- --- --- --- --- --- --- ---
            G   T      V   T   Q   G    T   D   P   V   K   T   Y   Y   Q   Y   T   P 279             288             297             306             315             324
           GTA TCA    TCA AAA GCC ATG  TAT GAC GCT TAC TGG AAC GGT AAA TTC AGA GAC TGC
           --- ---    --- --- --- ---  --- --- --- --- --- --- --- --- --- --- --- ---
            V   S      S   K   A   M    Y   D   A   Y   W   N   G   K   F   R   D   C 333             342             351             360             369             378
           GCT TTC    CAT TCT GGC TTT  AAT GAG GAT CCA TTC GTT TGT GAA TAT CAA GGC CAA
           --- ---    --- --- --- ---  --- --- --- --- --- --- --- --- --- --- --- ---
            A   F      H   S   G   F    N   E   D   P   F   V   C   E   Y   Q   G   Q 387             396             405    BspEI            423             432
           TCG TCT    GAC CTG CCT CAA  CCT CCT GTC AAT GCT TCC GGA GGT GGT GGA TCC GAG
           --- ---    --- --- --- ---  --- --- --- --- --- --- --- --- --- --- --- ---
            S   S      D   L   P   Q    P   P   V   N   A   S   G   G   G   G   S 441   XhoI   450  BstEII 459             468             477             486
           GTG CAG    CTG CTC GAG  CCC GGT CAC  CGT CTC CTC AGG TGG TGG TGG TTC TGG CGG 495             504              SacI           SpeI
           CGG CGG    CTC CGG TGG TGG  TGG TTC TGA GCT CGG GAC TAG T 3'
```

Figure 5.3
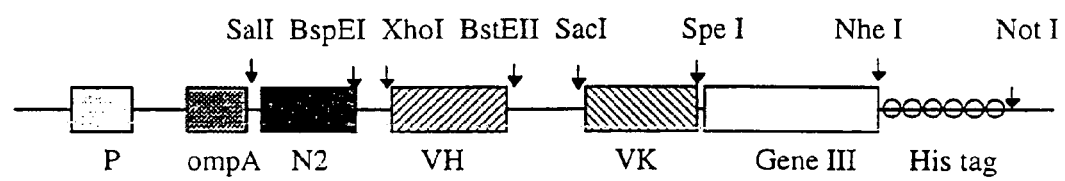

Figure 6.1
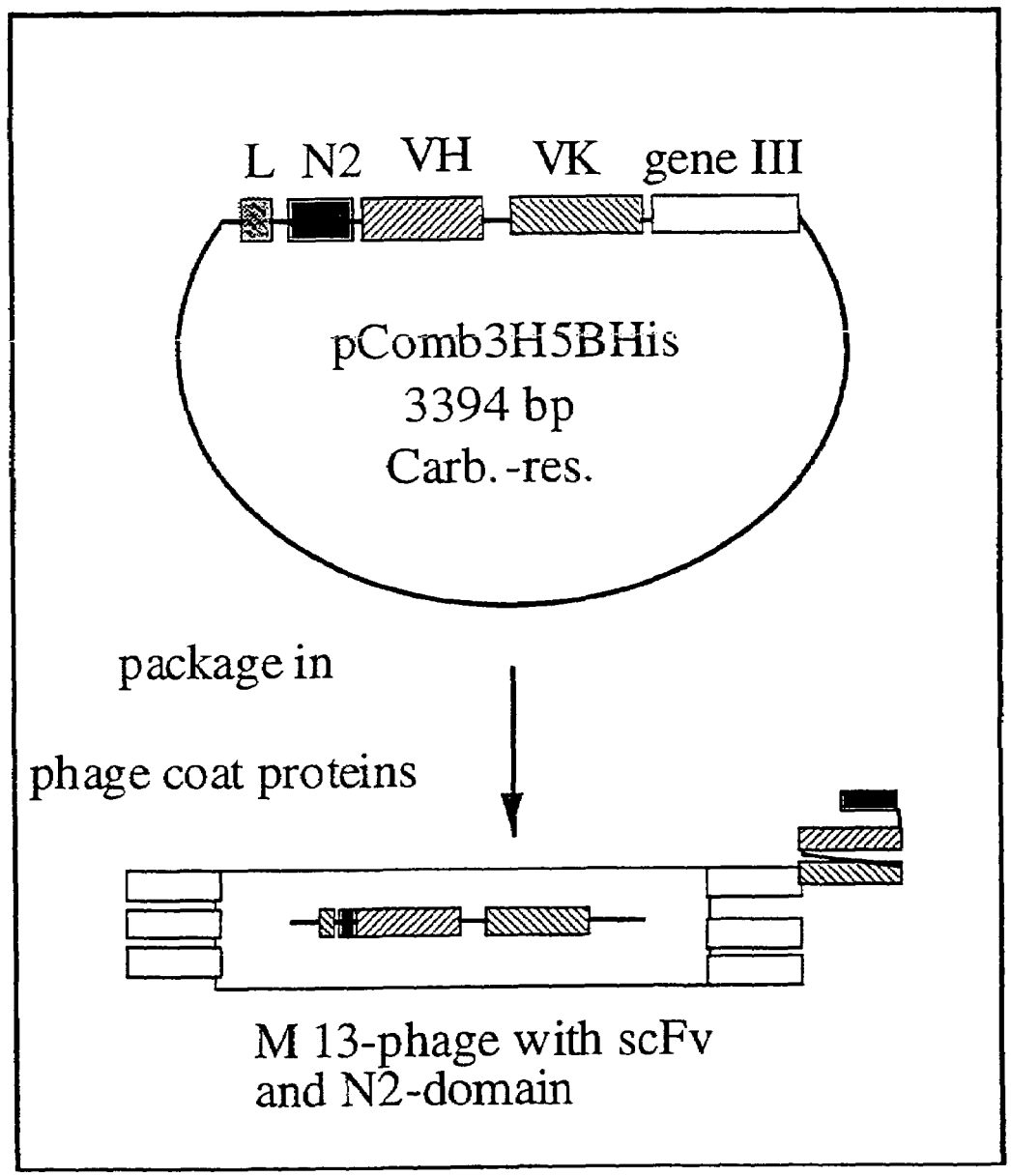

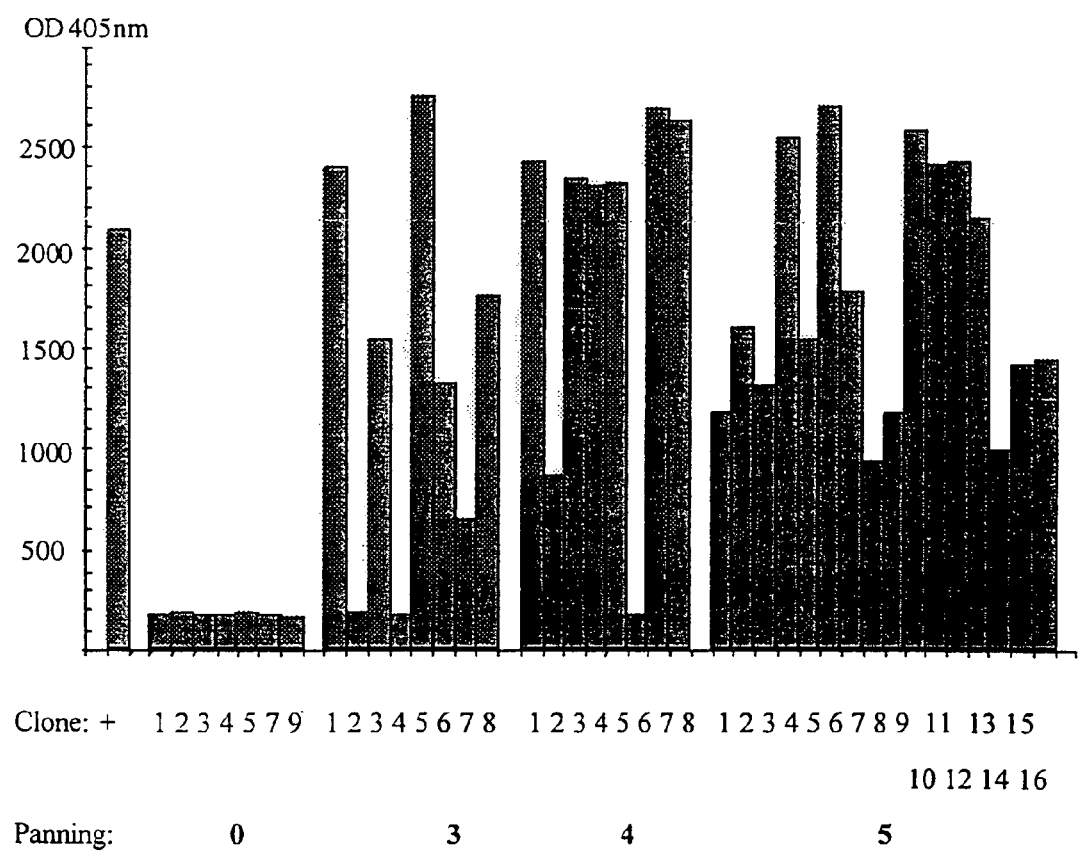
Figure 6.2

Figure 6.3

```
              9              18             27             36             45             54
5'  GAG GTG CAG CTG CTC GAG CAG TCT GGA GCT GAG CTG GTG AAA CCT GGG GCC TCA
    --- --- --- --- --- --- --- --- --- --- --- --- --- --- --- --- --- ---
     E   V   Q   L   L   E   Q   S   G   A   E   L   V   K   P   G   A   S
                 63             72             81             90             99            108
    GTG AAG ATA TCC TGC AAG GCT TCT GGA TAC GCC TTC ACT AAC TAC TGG CTA GGT
    --- --- --- --- --- --- --- --- --- --- --- --- --- --- --- --- --- ---
     V   K   I   S   C   K   A   S   G   Y   A   F   T   N   Y   W   L   G
                117            126            135            144            153            162
    TGG GTA AAG CAG AGG CCT GGA CAT GGA CTT GAG TGG ATT GGA GAT CTT TTC CCT
    --- --- --- --- --- --- --- --- --- --- --- --- --- --- --- --- --- ---
     W   V   K   Q   R   P   G   H   G   L   E   W   I   G   D   L   F   P
                171            180            189            198            207            216
    GGA AGT GGT AAT ACT CAC TAC AAT GAG AGG TTC AGG GGC AAA GCC ACA CTG ACT
    --- --- --- --- --- --- --- --- --- --- --- --- --- --- --- --- --- ---
     G   S   G   N   T   H   Y   N   E   R   F   R   G   K   A   T   L   T
                225            234            243            252            261            270
    GCA GAC AAA TCC TCG AGC ACA GCC TTT ATG CAG CTC AGT AGC CTG ACA TCT GAG
    --- --- --- --- --- --- --- --- --- --- --- --- --- --- --- --- --- ---
     A   D   K   S   S   S   T   A   F   M   Q   L   S   S   L   T   S   E
                279            288            297            306            315            324
    GAC TCT GCT GTC TAT TTC TGT GCA AGA TTG AGG AAC TGG GAC GAG GCT ATG GAC
    --- --- --- --- --- --- --- --- --- --- --- --- --- --- --- --- --- ---
     D   S   A   V   Y   F   C   A   R   L   R   N   W   D   E   A   M   D
                333            342            351            360            369            378
    TAC TGG GGC CAA GGG ACC ACG GTC ACC GTC TCC TCA GGT GGT GGT GGT TCT GGC
    --- --- --- --- --- --- --- --- --- --- --- --- --- --- --- --- --- ---
     Y   W   G   Q   G   T   T   V   T   V   S   S   G   G   G   G   S   G
                387            396            405            414            423            432
    GGC GGC GGC TCC GGT GGT GGT GGT TCT GAG CTC GTC ATG ACC CAG TCT CCA TCT
    --- --- --- --- --- --- --- --- --- --- --- --- --- --- --- --- --- ---
     G   G   G   S   G   G   G   G   S   E   L   V   M   T   Q   S   P   S
                441            450            459            468            477            486
    TAT CTT GCT GCA TCT CCT GGA GAA ACC ATT ACT ATT AAT TGC AGG GCA AGT AAG
    --- --- --- --- --- --- --- --- --- --- --- --- --- --- --- --- --- ---
     Y   L   A   A   S   P   G   E   T   I   T   I   N   C   R   A   S   K
                495            504            513            522            531            540
    AGC ATT AGC AAA TAT TTA GCC TGG TAT CAA GAG AAA CCT GGG AAA ACT AAT AAG
    --- --- --- --- --- --- --- --- --- --- --- --- --- --- --- --- --- ---
     S   I   S   K   Y   L   A   W   Y   Q   E   K   P   G   K   T   N   K
                549            558            567            576            585            594
    CTT CTT ATC TAC TCT GGA TCC ACT TTG CAA TCT GGA ATT CCA TCA AGG TTC AGT
    --- --- --- --- --- --- --- --- --- --- --- --- --- --- --- --- --- ---
     L   L   I   Y   S   G   S   T   L   Q   S   G   I   P   S   R   F   S
                603            612            621            630            639            648
    GGC AGT GGA TCT GGT ACA GAT TTC ACT CTC ACC ATC AGT AGC CTG GAG CCT GAA
    --- --- --- --- --- --- --- --- --- --- --- --- --- --- --- --- --- ---
     G   S   G   S   G   T   D   F   T   L   T   I   S   S   L   E   P   E
                657            666            675            684            693            702
    GAT TTT GCA ATG TAT TAC TGT CAA CAG CAT AAT GAA TAT CCG TAC ACG TTC GGA
    --- --- --- --- --- --- --- --- --- --- --- --- --- --- --- --- --- ---
     D   F   A   M   Y   Y   C   Q   Q   H   N   E   Y   P   Y   T   F   G
                711            720
    GGG GGG ACC AAG CTT GAG ATC AAA 3'
    --- --- --- --- --- --- --- ---
     G   G   T   K   L   E   I   K
```

Figure 6.4

```
                  9              18              27              36              45              54
5' GAG GTG CAG CTG CTC GAG CAG TCT GGA GCT GAG CTG GTA AGG CCT GGG ACT TCA
   --- --- --- --- --- --- --- --- --- --- --- --- --- --- --- --- --- ---
    E   V   Q   L   L   E   Q   S   G   A   E   L   V   R   P   G   T   S
                 63              72              81              90              99             108
   GTG AAG CTG TCC TGC AAG GCT TCT GGC TAC ACC TTC ACA AGC TAT GGT TTA AGC
   --- --- --- --- --- --- --- --- --- --- --- --- --- --- --- --- --- ---
    V   K   L   S   C   K   A   S   G   Y   T   F   T   S   Y   G   L   S
                117             126             135             144             153             162
   TGG GTG AAG CAG AGA ACT GGA CAG GGC CTT GAG TGG ATT GGA GAG GTT TAT CCT
   --- --- --- --- --- --- --- --- --- --- --- --- --- --- --- --- --- ---
    W   V   K   Q   R   T   G   Q   G   L   E   W   I   G   E   V   Y   P
                171             180             189             198             207             216
   AGA ATT GGT AAT GCT TAC TAC AAT GAG AAG TTC AAG GGC AAG GCC ACA CTG ACT
   --- --- --- --- --- --- --- --- --- --- --- --- --- --- --- --- --- ---
    R   I   G   N   A   Y   Y   N   E   K   F   K   G   K   A   T   L   T
                225             234             243             252             261             270
   GCA GAC AAA TCC TCC AGC ACA GCG TCC ATG GAG CTC CGC AGC CTG ACA TCT GAG
   --- --- --- --- --- --- --- --- --- --- --- --- --- --- --- --- --- ---
    A   D   K   S   S   S   T   A   S   M   E   L   R   S   L   T   S   E
                279             288             297             306             315             324
   GAC TCT GCG GTC TAT TTC TGT GCA AGA CGG GGA TCC TAC GGT AGT AAC TAC GAC
   --- --- --- --- --- --- --- --- --- --- --- --- --- --- --- --- --- ---
    D   S   A   V   Y   F   C   A   R   R   G   S   Y   G   S   N   Y   D
                333             342             351             360             369             378
   TGG TAC TTC GAT GTC TGG GGC CAA GGG ACC ACG GTC ACC GTC TCC TCA GGT GGT
   --- --- --- --- --- --- --- --- --- --- --- --- --- --- --- --- --- ---
    W   Y   F   D   V   W   G   Q   G   T   T   V   T   V   S   S   G   G
                387             396             405             414             423             432
   GGT GGT TCT GGC GGC GGC GGC TCC GGT GGT GGT GGT TCT GAG CTC GTG ATG ACC
   --- --- --- --- --- --- --- --- --- --- --- --- --- --- --- --- --- ---
    G   G   S   G   G   G   G   S   G   G   G   G   S   E   L   V   M   T
                441             450             459             468             477             486
   CAG ACT CCA CTC TCC CTG CCT GTC AGT CTT GGA GAT CAA GCC TCC ATC TCT TGC
   --- --- --- --- --- --- --- --- --- --- --- --- --- --- --- --- --- ---
    Q   T   P   L   S   L   P   V   S   L   G   D   Q   A   S   I   S   C
                495             504             513             522             531             540
   AGA TCT AGT CAG AGC CTT GTA CAC AGT AAT GGA AAC ACC TAT TTA CAT TGG TAC
   --- --- --- --- --- --- --- --- --- --- --- --- --- --- --- --- --- ---
    R   S   S   Q   S   L   V   H   S   N   G   N   T   Y   L   H   W   Y
                549             558             567             576             585             594
   CTG CAG AAG CCA GGC CAG TCT CCA AAG CTC CTG ATC TAC AAA GTT TCC AAC CGA
   --- --- --- --- --- --- --- --- --- --- --- --- --- --- --- --- --- ---
    L   Q   K   P   G   Q   S   P   K   L   L   I   Y   K   V   S   N   R
                603             612             621             630             639             648
   TTT TCT GGG GTC CCA GAC AGG TTC AGT GGC AGT GGA TCA GGG ACA GAT TTC ACA
   --- --- --- --- --- --- --- --- --- --- --- --- --- --- --- --- --- ---
    F   S   G   V   P   D   R   F   S   G   S   G   S   G   T   D   F   T
                657             666             675             684             693             702
   CTC AAG ATC AGC AGA GTG GAG GCT GAG GAT CTG GGA GTT TAT TTC TGC TCT CAA
   --- --- --- --- --- --- --- --- --- --- --- --- --- --- --- --- --- ---
    L   K   I   S   R   V   E   A   E   D   L   G   V   Y   F   C   S   Q
                711             720             729             738             747
   AGT ACA CAT GTT CCG TAC ACG TTC GGA GGG GGG ACC AAG CTT GAG ATC AAA 3'
   --- --- --- --- --- --- --- --- --- --- --- --- --- --- --- ---
    S   T   H   V   P   Y   T   F   G   G   G   T   K   L   E   I   K
```

Figure 6.5

```
                 9              18             27             36             45             54
5' GAG GTG CAG CTG CTC GAG CAG TCT GGA GCT GCG CTG GTA AGG CCT GGG ACT TCA
   --- --- --- --- --- --- --- --- --- --- --- --- --- --- --- --- --- ---
    E   V   Q   L   L   E   Q   S   G   A   A   L   V   R   P   G   T   S
                63             72             81             90             99            108
   GTG AAG ATA TCC TGC AAG GCT TCT GGA TAC GCC TTC ACT AAC TAC TGG CTA GGT
   --- --- --- --- --- --- --- --- --- --- --- --- --- --- --- --- --- ---
    V   K   I   S   C   K   A   S   G   Y   A   F   T   N   Y   W   L   G
               117            126            135            144            153            162
   TGG GTA AAG CAG AGG CCT GGA CAT GGA CTT GAG TGG ATT GGA GAT ATT TAC CCT
   --- --- --- --- --- --- --- --- --- --- --- --- --- --- --- --- --- ---
    W   V   K   Q   R   P   G   H   G   L   E   W   I   G   D   I   Y   P
               171            180            189            198            207            216
   GGA AGT GGT AAT ACT CAC TAC AAT GAG AGG TTC AGG GGC AAA GCC ACA CTG ACT
   --- --- --- --- --- --- --- --- --- --- --- --- --- --- --- --- --- ---
    G   S   G   N   T   H   Y   N   E   R   F   R   G   K   A   T   L   T
               225            234            243            252            261            270
   GCA GAC AAA TCC TCG AGC ACA GCC TTT ATG CAG CTC AGT AGC CTG ACA TCT GAG
   --- --- --- --- --- --- --- --- --- --- --- --- --- --- --- --- --- ---
    A   D   K   S   S   S   T   A   F   M   Q   L   S   S   L   T   S   E
               279            288            297            306            315            324
   GAC TCT GCT GTC TAT TTC TGT GCA AGA TTG AGG AAC TGG GAC GAG CCT ATG GAC
   --- --- --- --- --- --- --- --- --- --- --- --- --- --- --- --- --- ---
    D   S   A   V   Y   F   C   A   R   L   R   N   W   D   E   P   M   D
               333            342            351            360            369            378
   TAC TGG GGC CAA GGG ACC ACG GTC ACC GTC TCC TCA GGT GGT GGT GGT TCT GGC
   --- --- --- --- --- --- --- --- --- --- --- --- --- --- --- --- --- ---
    Y   W   G   Q   G   T   T   V   T   V   S   S   G   G   G   G   S   G
               387            396            405            414            423            432
   GGC GGC GGC TCC GGT GGT GGT GGT TCT GAG CTC CAG ATG ACC CAG TCT CCA TCT
   --- --- --- --- --- --- --- --- --- --- --- --- --- --- --- --- --- ---
    G   G   G   S   G   G   G   G   S   E   L   Q   M   T   Q   S   P   S
               441            450            459            468            477            486
   TAT CTT GCT GCA TCT CCT GGA GAA ACC ATT ACT ATT AAT TGC AGG GCA AGT AAG
   --- --- --- --- --- --- --- --- --- --- --- --- --- --- --- --- --- ---
    Y   L   A   A   S   P   G   E   T   I   T   I   N   C   R   A   S   K
               495            504            513            522            531            540
   AGC ATT AGC AAA TAT TTA GCC TGG TAT CAA GAG AAA CCT GGG AAA ACT AAT AAG
   --- --- --- --- --- --- --- --- --- --- --- --- --- --- --- --- --- ---
    S   I   S   K   Y   L   A   W   Y   Q   E   K   P   G   K   T   N   K
               549            558            567            576            585            594
   CTT CTT ATC TAC TCT GGA TCC ACT TTG CAA TCT GGA ATT CCA TCA AGG TTC AGT
   --- --- --- --- --- --- --- --- --- --- --- --- --- --- --- --- --- ---
    L   L   I   Y   S   G   S   T   L   Q   S   G   I   P   S   R   F   S
               603            612            621            630            639            648
   GGC AGT GGA TCT GGT ACA GAT TTC ACT CTC ACC ATC AGT AGC CTG GAG CCT GAA
   --- --- --- --- --- --- --- --- --- --- --- --- --- --- --- --- --- ---
    G   S   G   S   G   T   D   F   T   L   T   I   S   S   L   E   P   E
               657            666            675            684            693            702
   GAT TTT GCA ATG TAT TAC TGT CAA CAG CAT AAT GAA TAC CCG TAC ACG TTC GGA
   --- --- --- --- --- --- --- --- --- --- --- --- --- --- --- --- --- ---
    D   F   A   M   Y   Y   C   Q   Q   H   N   E   Y   P   Y   T   F   G
               711            720
   GGG GGG ACC AAG CTT GAG ATC AAA 3'
   --- --- --- --- --- --- --- ---
    G   G   T   K   L   E   I   K
```

Figure 6.6

```
              9              18              27              36              45              54
5' GAG GTG CAG CTG CTC GAG CAG TCT GGA GCT GAG CTG GTA AGG CCT GGG ACT TCA
   --- --- --- --- --- --- --- --- --- --- --- --- --- --- --- --- --- ---
    E   V   Q   L   L   E   Q   S   G   A   E   L   V   R   P   G   T   S
             63              72              81              90              99             108
   GTG AAG ATA TCC TGC AAG GCT TCT GGA TAC GCC TTC ACT AAC TAC TGG CTA GGT
   --- --- --- --- --- --- --- --- --- --- --- --- --- --- --- --- --- ---
    V   K   I   S   C   K   A   S   G   Y   A   F   T   N   Y   W   L   G
            117             126             135             144             153             162
   TGG GTT AAG CAG AGG CCT GGA CAT GGA CTT GAA TGG GTT GGA GAT ATT TTC CCT
   --- --- --- --- --- --- --- --- --- --- --- --- --- --- --- --- --- ---
    W   V   K   Q   R   P   G   H   G   L   E   W   V   G   D   I   F   P
            171             180             189             198             207             216
   GGA AGT GGT AAT GCT CAC TAC AAT GAG AAG TTC AAG GGC AAA GCC ACA CTG ACT
   --- --- --- --- --- --- --- --- --- --- --- --- --- --- --- --- --- ---
    G   S   G   N   A   H   Y   N   E   K   F   K   G   K   A   T   L   T
            225             234             243             252             261             270
   GCA GAC AAG TCC TCG TAC ACA GCC TAT ATG CAG CTC AGT AGC CTG ACA TCT GAG
   --- --- --- --- --- --- --- --- --- --- --- --- --- --- --- --- --- ---
    A   D   K   S   S   Y   T   A   Y   M   Q   L   S   S   L   T   S   E
            279             288             297             306             315             324
   GAC TCT GCT GTC TAT TTC TGT GCA AGA TTG CGG AAC TGG GAC GAG GCT ATG GAC
   --- --- --- --- --- --- --- --- --- --- --- --- --- --- --- --- --- ---
    D   S   A   V   Y   F   C   A   R   L   R   N   W   D   E   A   M   D
            333             342             351             360             369             378
   TAC TGG GGC CAA GGG ACC ACG GTC ACC GTC TCC TCA GGT GGT GGT GGT TCT GGC
   --- --- --- --- --- --- --- --- --- --- --- --- --- --- --- --- --- ---
    Y   W   G   Q   G   T   T   V   T   V   S   S   G   G   G   G   S   G
            387             396             405             414             423             432
   GGC GGC GGC TCC GGT GGT GGT GGT TCT GAG CTC GTG ATG ACA CAG TCT CCA TCC
   --- --- --- --- --- --- --- --- --- --- --- --- --- --- --- --- --- ---
    G   G   G   S   G   G   G   G   S   E   L   V   M   T   Q   S   P   S
            441             450             459             468             477             486
   TCC CTG AGT GTG TCA GCA GGA GAG AAG GTC ACT ATG AGC TGC AAG TCC AGT CAG
   --- --- --- --- --- --- --- --- --- --- --- --- --- --- --- --- --- ---
    S   L   S   V   S   A   G   E   K   V   T   M   S   C   K   S   S   Q
            495             504             513             522             531             540
   AGT CTG TTA AAC AGT GGA AAT CAA AAG AAC TAC TTG GCC TGG TAC CAG CAG AAA
   --- --- --- --- --- --- --- --- --- --- --- --- --- --- --- --- --- ---
    S   L   L   N   S   G   N   Q   K   N   Y   L   A   W   Y   Q   Q   K
            549             558             567             576             585             594
   CCA GGG CAG CCT CCT AAA CTG TTG ATC TAC GGG GCA TCC ACT AGG GAA TCT GGG
   --- --- --- --- --- --- --- --- --- --- --- --- --- --- --- --- --- ---
    P   G   Q   P   P   K   L   L   I   Y   G   A   S   T   R   E   S   G
            603             612             621             630             639             648
   GTC CCT GAT CGC TTC ACA GGC AGT GGA TCT GGA ACA GAT TTC ACT CTC ACC ATC
   --- --- --- --- --- --- --- --- --- --- --- --- --- --- --- --- --- ---
    V   P   D   R   F   T   G   S   G   S   G   T   D   F   T   L   T   I
            657             666             675             684             693             702
   AGC AGT GTG CAG GCT GAA GAC CTG GCA GTT TAT TAC TGT CAG AAT GAT TAT AGT
   --- --- --- --- --- --- --- --- --- --- --- --- --- --- --- --- --- ---
    S   S   V   Q   A   E   D   L   A   V   Y   Y   C   Q   N   D   Y   S
            711             720             729             738
   TAT CCG TAC ACG TTC GGA GGG GGG ACC AAG CTT GAG ATC AAA -3'
   --- --- --- --- --- --- --- --- --- --- --- --- ---
    Y   P   Y   T   F   G   G   G   T   K   L   E   I   K
```

Figure 6.7

```
                9              18              27              36              45              54
5' GAG GTG CAG CTG CTC GAG CAG TCT GGA GCT GAG CTG GTG AGG CCT GGG GCT TCA
   --- --- --- --- --- --- --- --- --- --- --- --- --- --- --- --- --- ---
    E   V   Q   L   L   E   Q   S   G   A   E   L   V   R   P   G   A   S
               63              72              81              90              99             108
   GTG AAG ATA TCC TGC AAG GCT TCT GGA TAC GCC TTC AAT AAC TAC TGG CTA GGT
   --- --- --- --- --- --- --- --- --- --- --- --- --- --- --- --- --- ---
    V   K   I   S   C   K   A   S   G   Y   A   F   N   N   Y   W   L   G
              117             126             135             144             153             162
   TGG GTA AAG CAG AGG CCT GGA CAT GGA CTT GAG TGG ATT GGA GAC ATT TAC CCT
   --- --- --- --- --- --- --- --- --- --- --- --- --- --- --- --- --- ---
    W   V   K   Q   R   P   G   H   G   L   E   W   I   G   D   I   Y   P
              171             180             189             198             207             216
   GGA AGT GGA AAT ACT CAC TAC AAT GAG AGG TTC AGG GGC AAA GCC ACA CTG ACT
   --- --- --- --- --- --- --- --- --- --- --- --- --- --- --- --- --- ---
    G   S   G   N   T   H   Y   N   E   R   F   R   G   K   A   T   L   T
              225             234             243             252             261             270
   GCA GAC AAA TCC TCG AGC ACA GCC TTT ATG CAG TTA AGT AGC CTG ACA TCT GAG
   --- --- --- --- --- --- --- --- --- --- --- --- --- --- --- --- --- ---
    A   D   K   S   S   S   T   A   F   M   Q   L   S   S   L   T   S   E
              279             288             297             306             315             324
   GAC TCT GCT GTC TAT TTC TGT GCA AGA TTG AGG AAC TGG GAC GAG GCT ATG GAC
   --- --- --- --- --- --- --- --- --- --- --- --- --- --- --- --- --- ---
    D   S   A   V   Y   F   C   A   R   L   R   N   W   D   E   A   M   D
              333             342             351             360             369             378
   TAC TGG GGC CAA GGG ACC ACG GTC ACC GTC TCC TCA GGT GGT GGT GGT TCT GGC
   --- --- --- --- --- --- --- --- --- --- --- --- --- --- --- --- --- ---
    Y   W   G   Q   G   T   T   V   T   V   S   S   G   G   G   G   S   G
              387             396             405             414             423             432
   GGC GGC GGC TCC GGT GGT GGT GGT TCT GAG CTC GTC ATG ACC CAG TCT CCA TCT
   --- --- --- --- --- --- --- --- --- --- --- --- --- --- --- --- --- ---
    G   G   G   S   G   G   G   G   S   E   L   V   M   T   Q   S   P   S
              441             450             459             468             477             486
   TAT CTT GCT GCA TCT CCT GGA GAA ACC ATT ACT ATT AAT TGC AGG GCA AGT AAG
   --- --- --- --- --- --- --- --- --- --- --- --- --- --- --- --- --- ---
    Y   L   A   A   S   P   G   E   T   I   T   I   N   C   R   A   S   K
              495             504             513             522             531             540
   AGC ATT AGC AAA TAT TTA GCC TGG TAT CAA GAG AAA CCT GGG AAA ACT AAT AAG
   --- --- --- --- --- --- --- --- --- --- --- --- --- --- --- --- --- ---
    S   I   S   K   Y   L   A   W   Y   Q   E   K   P   G   K   T   N   K
              549             558             567             576             585             594
   CTT CTT ATC TAC TCT GGA TCC ACT TTG CAA TCT GGA ATT CCA TCA AGG TTC AGT
   --- --- --- --- --- --- --- --- --- --- --- --- --- --- --- --- --- ---
    L   L   I   Y   S   G   S   T   L   Q   S   G   I   P   S   R   F   S
              603             612             621             630             639             648
   GGC AGT GGA TCT GGT ACA GAT TTC ACT CTC ACC ATC AGT AGC CTG GAG CCT GAA
   --- --- --- --- --- --- --- --- --- --- --- --- --- --- --- --- --- ---
    G   S   G   S   G   T   D   F   T   L   T   I   S   S   L   E   P   E
              657             666             675             684             693             702
   GAT TTT GCA ATG TAT TAC TGT CAA CAG CAT AAT GAA TAC CCG TAC ACG TTC GGA
   --- --- --- --- --- --- --- --- --- --- --- --- --- --- --- --- --- ---
    D   F   A   M   Y   Y   C   Q   Q   H   N   E   Y   P   Y   T   F   G
              711             720
   GGG GGG ACC AAG CTT GAG ATC AAA 3'
   --- --- --- --- --- --- --- ---
    G   G   T   K   L   E   I   K
```

Figure 6.8

```
              9          18            27            36            45            54
5' GAG GTG CAG CTG CTC GAG CAG TCT GGA GCT GAG CTG GCG AGG CCT GGG GCT TCA
   --- --- --- --- --- --- --- --- --- --- --- --- --- --- --- --- --- ---
    E   V   Q   L   L   E   Q   S   G   A   E   L   A   R   P   G   A   S
              63           72            81            90            99           108
   GTG AAG CTG TCC TGC AAG GCT TCT GGC TAC ACC TTC ACA AAC TAT GGT TTA AGC
   --- --- --- --- --- --- --- --- --- --- --- --- --- --- --- --- --- ---
    V   K   L   S   C   K   A   S   G   Y   T   F   T   N   Y   G   L   S
             117          126           135           144           153           162
   TGG GTG AAG CAG AGG CCT GGA CAG GTC CTT GAG TGG ATT GGA GAG GTT TAT CCT
   --- --- --- --- --- --- --- --- --- --- --- --- --- --- --- --- --- ---
    W   V   K   Q   R   P   G   Q   V   L   E   W   I   G   E   V   Y   P
             171          180           189           198           207           216
   AGA ATT GGT AAT GCT TAC TAC AAT GAG AAG TTC AAG GGC AAG GCC ACA CTG ACT
   --- --- --- --- --- --- --- --- --- --- --- --- --- --- --- --- --- ---
    R   I   G   N   A   Y   Y   N   E   K   F   K   G   K   A   T   L   T
             225          234           243           252           261           270
   GCA GAC AAA TCC TCC AGC ACA GCG TCC ATG GAG CTC CGC AGC CTG ACC TCT GAG
   --- --- --- --- --- --- --- --- --- --- --- --- --- --- --- --- --- ---
    A   D   K   S   S   S   T   A   S   M   E   L   R   S   L   T   S   E
             279          288           297           306           315           324
   GAC TCT GCG GTC TAT TTC TGT GCA AGA CGG GGA TCC TAC GAT ACT AAC TAC GAC
   --- --- --- --- --- --- --- --- --- --- --- --- --- --- --- --- --- ---
    D   S   A   V   Y   F   C   A   R   R   G   S   Y   D   T   N   Y   D
             333          342           351           360           369           378
   TGG TAC TTC GAT GTC TGG GGC CAA GGG ACC ACG GTC ACC GTC TCC TCA GGT GGT
   --- --- --- --- --- --- --- --- --- --- --- --- --- --- --- --- --- ---
    W   Y   F   D   V   W   G   Q   G   T   T   V   T   V   S   S   G   G
             387          396           405           414           423           432
   GGT GGT TCT GGC GGC GGC GGC TCC GGT GGT GGT GGT TCT GAG CTC GTG ATG ACC
   --- --- --- --- --- --- --- --- --- --- --- --- --- --- --- --- --- ---
    G   G   S   G   G   G   G   S   G   G   G   G   S   E   L   V   M   T
             441          450           459           468           477           486
   CAG ACT CCA CTC TCC CTG CCT GTC AGT CTT GGA GAT CAA GCC TCC ATC TCT TGC
   --- --- --- --- --- --- --- --- --- --- --- --- --- --- --- --- --- ---
    Q   T   P   L   S   L   P   V   S   L   G   D   Q   A   S   I   S   C
             495          504           513           522           531           540
   AGA TCT AGT CAG AGC CTT GTA CAC AGT AAT GGA AAC ACC TAT TTA CAT TGG TAC
   --- --- --- --- --- --- --- --- --- --- --- --- --- --- --- --- --- ---
    R   S   S   Q   S   L   V   H   S   N   G   N   T   Y   L   H   W   Y
             549          558           567           576           585           594
   CTG CAG AAG CCA GGC CAG TCT CCA AAG CTC CTG ATC TAC AAA GTT TCC AAC CGA
   --- --- --- --- --- --- --- --- --- --- --- --- --- --- --- --- --- ---
    L   Q   K   P   G   Q   S   P   K   L   L   I   Y   K   V   S   N   R
             603          612           621           630           639           648
   TTT TCT GGG GTC CCA GAC AGG TTC AGT GGC AGT GGA TCA GGG ACA GAT TTC ACA
   --- --- --- --- --- --- --- --- --- --- --- --- --- --- --- --- --- ---
    F   S   G   V   P   D   R   F   S   G   S   G   S   G   T   D   F   T
             657          666           675           684           693           702
   CTC AAG ATC AGC AGA GTG GAG GCT GAG GAT CTG GGA GTT TAT TTC TGC TCT CAA
   --- --- --- --- --- --- --- --- --- --- --- --- --- --- --- --- --- ---
    L   K   I   S   R   V   E   A   E   D   L   G   V   Y   F   C   S   Q
             711          720           729           738           747
   AGT ACA CAT GTT CCG TAC ACG TTC GGA GGG GGG ACC AAG CTT GAG ATC AAA 3'
   --- --- --- --- --- --- --- --- --- --- --- --- --- --- --- --- ---
    S   T   H   V   P   Y   T   F   G   G   G   T   K   L   E   I   K
```

Figure 6.9

```
                  9              18              27              36              45              54
5' GAG GTG CAG CTG CTC GAG TCT GGA GGT GGC CTG GTG CAG CCT GGA GGA TCC CTG
   --- --- --- --- --- --- --- --- --- --- --- --- --- --- --- --- ---
    E   V   Q   L   L   E   S   G   G   G   L   V   Q   P   G   G   S   L
                 63              72              81              90              99             108
   AAA CTC TCC TGT GCA GCC TCA GGA TTC GAT TTT AGT AGA TAC TGG ATG AGT TGG
   --- --- --- --- --- --- --- --- --- --- --- --- --- --- --- --- ---
    K   L   S   C   A   A   S   G   F   D   F   S   R   Y   W   M   S   W
                117             126             135             144             153             162
   GTC CGG CAG GCT CCA GGG AAA GGG CTA GAA TGG ATT GGA GAA ATT AAT CCA GAT
   --- --- --- --- --- --- --- --- --- --- --- --- --- --- --- --- ---
    V   R   Q   A   P   G   K   G   L   E   W   I   G   E   I   N   P   D
                171             180             189             198             207             216
   AGC AGT ACG ATA AAC TAT ACG CCA TCT CTG AAG GAT AAA TTC ATC ATC TCC AGA
   --- --- --- --- --- --- --- --- --- --- --- --- --- --- --- --- ---
    S   S   T   I   N   Y   T   P   S   L   K   D   K   F   I   I   S   R
                225             234             243             252             261             270
   GAC AAC GCC AAA AAT ACG CTG TAC CTG CAA ATG GGC AAA GTG AGA TCT GAG GAC
   --- --- --- --- --- --- --- --- --- --- --- --- --- --- --- --- ---
    D   N   A   K   N   T   L   Y   L   Q   M   G   K   V   R   S   E   D
                279             288             297             306             315             324
   ACA GCC CTT TAT TAC TGT GCA AGA GGA GCC TTC CTT TTT GAC TAC TGG GGC CAA
   --- --- --- --- --- --- --- --- --- --- --- --- --- --- --- --- ---
    T   A   L   Y   Y   C   A   R   G   A   F   L   F   D   Y   W   G   Q
                333             342             351             360             369             378
   GGG ACC ACG GTC ACC GTC TCC TCA GGT GGT GGT GGT TCT GGC GGC GGC GGC TCC
   --- --- --- --- --- --- --- --- --- --- --- --- --- --- --- --- ---
    G   T   T   V   T   V   S   S   G   G   G   G   S   G   G   G   G   S
                387             396             405             414             423             432
   GGT GGT GGT GGT TCT GAG CTC GTG CTC ACC CAG TCT CCA ACC ACC ATG GCT GCA
   --- --- --- --- --- --- --- --- --- --- --- --- --- --- --- --- ---
    G   G   G   G   S   E   L   V   L   T   Q   S   P   T   T   M   A   A
                441             450             459             468             477             486
   TCT CCC GGG GAG AAG ATC ACT ATC ACC TGC AGT GCC AGC TCA AGT ATA AGT TCC
   --- --- --- --- --- --- --- --- --- --- --- --- --- --- --- --- ---
    S   P   G   E   K   I   T   I   T   C   S   A   S   S   S   I   S   S
                495             504             513             522             531             540
   AAT TAC TTG CAT TGG TAT CAG CAG AAG CCA GGA TTC TCC CCT AAA CTC TTG ATT
   --- --- --- --- --- --- --- --- --- --- --- --- --- --- --- --- ---
    N   Y   L   H   W   Y   Q   Q   K   P   G   F   S   P   K   L   L   I
                549             558             567             576             585             594
   TAT AGG ACA TCC AAT CTG GCT TCT GGA GTC CCA GCT CGC TTC AGT GGC AGT GGG
   --- --- --- --- --- --- --- --- --- --- --- --- --- --- --- --- ---
    Y   R   T   S   N   L   A   S   G   V   P   A   R   F   S   G   S   G
                603             612             621             630             639             648
   TCT GGG ACC TCT TAC TCT CTC ACA ATT GGC ACC ATG GAG GCT GAA GAT GTT GCC
   --- --- --- --- --- --- --- --- --- --- --- --- --- --- --- --- ---
    S   G   T   S   Y   S   L   T   I   G   T   M   E   A   E   D   V   A
                657             666             675             684             693             702
   ACT TAC TAC TGC CAG CAG GGT AGT AGT ATA CCA CTC ACG TTC GGT GCT GGG ACC
   --- --- --- --- --- --- --- --- --- --- --- --- --- --- --- --- ---
    T   Y   Y   C   Q   Q   G   S   S   I   P   L   T   F   G   A   G   T
                711
   AAG CTT GAG ATC AAA 3'
   --- --- --- --- ---
    K   L   E   I   K
```

Figure 6.10

```
              9             18            27            36            45            54
5' GAG GTG CAG CTG CTC GAG CAG TCT GGA GCT GAG CTG GTA AGG CCT GGG ACT TCA
   --- --- --- --- --- --- --- --- --- --- --- --- --- --- --- --- --- ---
    E   V   Q   L   L   E   Q   S   G   A   E   L   V   R   P   G   T   S
              63            72            81            90            99           108
   GTG AAG ATA TCC TGC AAG GCT TCT GGA TAC GCC TTC ACT AAC TAC TGG CTA GGT
   --- --- --- --- --- --- --- --- --- --- --- --- --- --- --- --- --- ---
    V   K   I   S   C   K   A   S   G   Y   A   F   T   N   Y   W   L   G
             117           126           135           144           153           162
   TGG GTA AAG CAG AGG CCT GGA CAT GGA CTT GAG TGG ATT GGA GAT ATT TTC CCT
   --- --- --- --- --- --- --- --- --- --- --- --- --- --- --- --- --- ---
    W   V   K   Q   R   P   G   H   G   L   E   W   I   G   D   I   F   P
             171           180           189           198           207           216
   GGA AGT GGT AAT ATC CAC TAC AAT GAG AAG TTC AAG GGC AAA GCC ACA CTG ACT
   --- --- --- --- --- --- --- --- --- --- --- --- --- --- --- --- --- ---
    G   S   G   N   I   H   Y   N   E   K   F   K   G   K   A   T   L   T
             225           234           243           252           261           270
   GCA GAC AAA TCT TCG AGC ACA GCC TAT ATG CAG CTC AGT AGC CTG ACA TTT GAG
   --- --- --- --- --- --- --- --- --- --- --- --- --- --- --- --- --- ---
    A   D   K   S   S   S   T   A   Y   M   Q   L   S   S   L   T   F   E
             279           288           297           306           315           324
   GAC TCT GCT GTC TAT TTC TGT GCA AGA CTG AGG AAC TGG GAC GAG CCT ATG GAC
   --- --- --- --- --- --- --- --- --- --- --- --- --- --- --- --- --- ---
    D   S   A   V   Y   F   C   A   R   L   R   N   W   D   E   P   M   D
             333           342           351           360           369           378
   TAC TGG GGC CAA GGG ACC ACG GTC ACC GTC TCC TCA GGT GGT GGT GGT TCT GGC
   --- --- --- --- --- --- --- --- --- --- --- --- --- --- --- --- --- ---
    Y   W   G   Q   G   T   T   V   T   V   S   S   G   G   G   G   S   G
             387           396           405           414           423           432
   GGC GGC GGC TCC GGT GGT GGT GGT TCT GAG CTC GTG ATG ACA CAG TCT CCA TCC
   --- --- --- --- --- --- --- --- --- --- --- --- --- --- --- --- --- ---
    G   G   G   S   G   G   G   G   S   E   L   V   M   T   Q   S   P   S
             441           450           459           468           477           486
   TCC CTG ACT GTG ACA GCA GGA GAG AAG GTC ACT ATG AGC TGC AAG TCC AGT CAG
   --- --- --- --- --- --- --- --- --- --- --- --- --- --- --- --- --- ---
    S   L   T   V   T   A   G   E   K   V   T   M   S   C   K   S   S   Q
             495           504           513           522           531           540
   AGT CTG TTA AAC AGT GGA AAT CAA AAG AAC TAC TTG ACC TGG TAC CAG CAG AAA
   --- --- --- --- --- --- --- --- --- --- --- --- --- --- --- --- --- ---
    S   L   L   N   S   G   N   Q   K   N   Y   L   T   W   Y   Q   Q   K
             549           558           567           576           585           594
   CCA GGG CAG CCT CCT AAA CTG TTG ATC TAC TGG GCA TCC ACT AGG GAA TCT GGG
   --- --- --- --- --- --- --- --- --- --- --- --- --- --- --- --- --- ---
    P   G   Q   P   P   K   L   L   I   Y   W   A   S   T   R   E   S   G
             603           612           621           630           639           648
   GTC CCT GAT CGC TTC ACA GGC AGT GGA TCT GGA ACA GAT TTC ACT CTC ACC ATC
   --- --- --- --- --- --- --- --- --- --- --- --- --- --- --- --- --- ---
    V   P   D   R   F   T   G   S   G   S   G   T   D   F   T   L   T   I
             657           666           675           684           693           702
   AGC AGT GTG CAG GCT GAA GAC CTG GCA GTT TAT TAC TGT CAG AAT GAT TAT AGT
   --- --- --- --- --- --- --- --- --- --- --- --- --- --- --- --- --- ---
    S   S   V   Q   A   E   D   L   A   V   Y   Y   C   Q   N   D   Y   S
             711           720           729           738
   TAT CCG CTC ACG TTC GGT GCT GGG ACC AAG CTT GAG ATC AAA 3'
   --- --- --- --- --- --- --- --- --- --- --- --- --- ---
    Y   P   L   T   F   G   A   G   T   K   L   E   I   K
```

Figure 7

```
                9              18              27              36              45              54
5' GAG GTG CAG CTG CTC GAG CAG TCT GGA GCT GAG CTG GTA AGG CCT GGG ACT TCA
   --- --- --- --- --- --- --- --- --- --- --- --- --- --- --- --- --- ---
    E   V   Q   L   L   E   Q   S   G   A   E   L   V   R   P   G   T   S
                63              72              81              90              99             108
   GTG AAG ATA TCC TGC AAG GCT TCT GGA TAC GCC TTC ACT AAC TAC TGG CTA GGT
   --- --- --- --- --- --- --- --- --- --- --- --- --- --- --- --- --- ---
    V   K   I   S   C   K   A   S   G   Y   A   F   T   N   Y   W   L   G
               117             126             135             144             153             162
   TGG GTT AAG CAG AGG CCT GGA CAT GGA CTT GAA TGG GTT GGA GAT ATT TTC CCT
   --- --- --- --- --- --- --- --- --- --- --- --- --- --- --- --- --- ---
    W   V   K   Q   R   P   G   H   G   L   E   W   V   G   D   I   F   P
               171             180             189             198             207             216
   GGA AGT GGT AAT GCT CAC TAC AAT GAG AAG TTC AAG GGC AAA GCC ACA CTG ACT
   --- --- --- --- --- --- --- --- --- --- --- --- --- --- --- --- --- ---
    G   S   G   N   A   H   Y   N   E   K   F   K   G   K   A   T   L   T
               225             234             243             252             261             270
   GCA GAC AAG TCC TCG TAC ACA GCC TAT ATG CAG CTC AGT AGC CTG ACA TCT GAG
   --- --- --- --- --- --- --- --- --- --- --- --- --- --- --- --- --- ---
    A   D   K   S   S   Y   T   A   Y   M   Q   L   S   S   L   T   S   E
               279             288             297             306             315             324
   GAC TCT GCT GTC TAT TTC TGT GCA AGA TTG CGG AAC TGG GAC GAG GCT ATG GAC
   --- --- --- --- --- --- --- --- --- --- --- --- --- --- --- --- --- ---
    D   S   A   V   Y   F   C   A   R   L   R   N   W   D   E   A   M   D
               333             342             351             360             369             378
   TAC TGG GGC CAA GGG ACC ACG GTC ACC GTC TCC TCA GGT GGT GGT GGT TCT GGC
   --- --- --- --- --- --- --- --- --- --- --- --- --- --- --- --- --- ---
    Y   W   G   Q   G   T   T   V   T   V   S   S   G   G   G   G   S   G
               387             396             405             414             423             432
   GGC GGC GGC TCC GGT GGT GGT GGT TCT GAG CTC GTG ATG ACA CAG TCT CCA TCC
   --- --- --- --- --- --- --- --- --- --- --- --- --- --- --- --- --- ---
    G   G   G   S   G   G   G   G   S   E   L   V   M   T   Q   S   P   S
               441             450             459             468             477             486
   TCC CTG GCT ATG TCA GTA GGA CAG AAG GTC ACT ATG AGC TGC AAG TCC AGT CAG
   --- --- --- --- --- --- --- --- --- --- --- --- --- --- --- --- --- ---
    S   L   A   M   S   V   G   Q   K   V   T   M   S   C   K   S   S   Q
               495             504             513             522             531             540
   AGC CTT TTA AAT AGT AGC AAT CAA AAG AAC TAT TTG GCC TGG TAC CAG CAG AAA
   --- --- --- --- --- --- --- --- --- --- --- --- --- --- --- --- --- ---
    S   L   L   N   S   S   N   Q   K   N   Y   L   A   W   Y   Q   Q   K
               549             558             567             576             585             594
   CAA GGG CAG CCT CCT AAA CTG CTT ATC TAT GGG GCA TCC ATT AGA GAA TCT TGG
   --- --- --- --- --- --- --- --- --- --- --- --- --- --- --- --- --- ---
    Q   G   Q   P   P   K   L   L   I   Y   G   A   S   I   R   E   S   W
               603             612             621             630             639             648
   GTC CCT GAT CGA TTC ACA GGA AGT GGA TCT GGG ACA GAC TTC ACT CTC ACC ATC
   --- --- --- --- --- --- --- --- --- --- --- --- --- --- --- --- --- ---
    V   P   D   R   F   T   G   S   G   S   G   T   D   F   T   L   T   I
               657             666             675             684             693             702
   AGC AGT GTG AAG GCT GAA GAC CTG GCA GTT TAT TAC TGT CAG CAA TAT TAT AGC
   --- --- --- --- --- --- --- --- --- --- --- --- --- --- --- --- --- ---
    S   S   V   K   A   E   D   L   A   V   Y   Y   C   Q   Q   Y   Y   S
               711             720             729             738
   TAT CCG TAC ACG TTC GGA GGG GGG ACC AAG CTT GAG ATC AAA 3'
   --- --- --- --- --- --- --- --- --- --- --- --- --- ---
    Y   P   Y   T   F   G   G   G   T   K   L   E   I   K
```

Figure 8.1
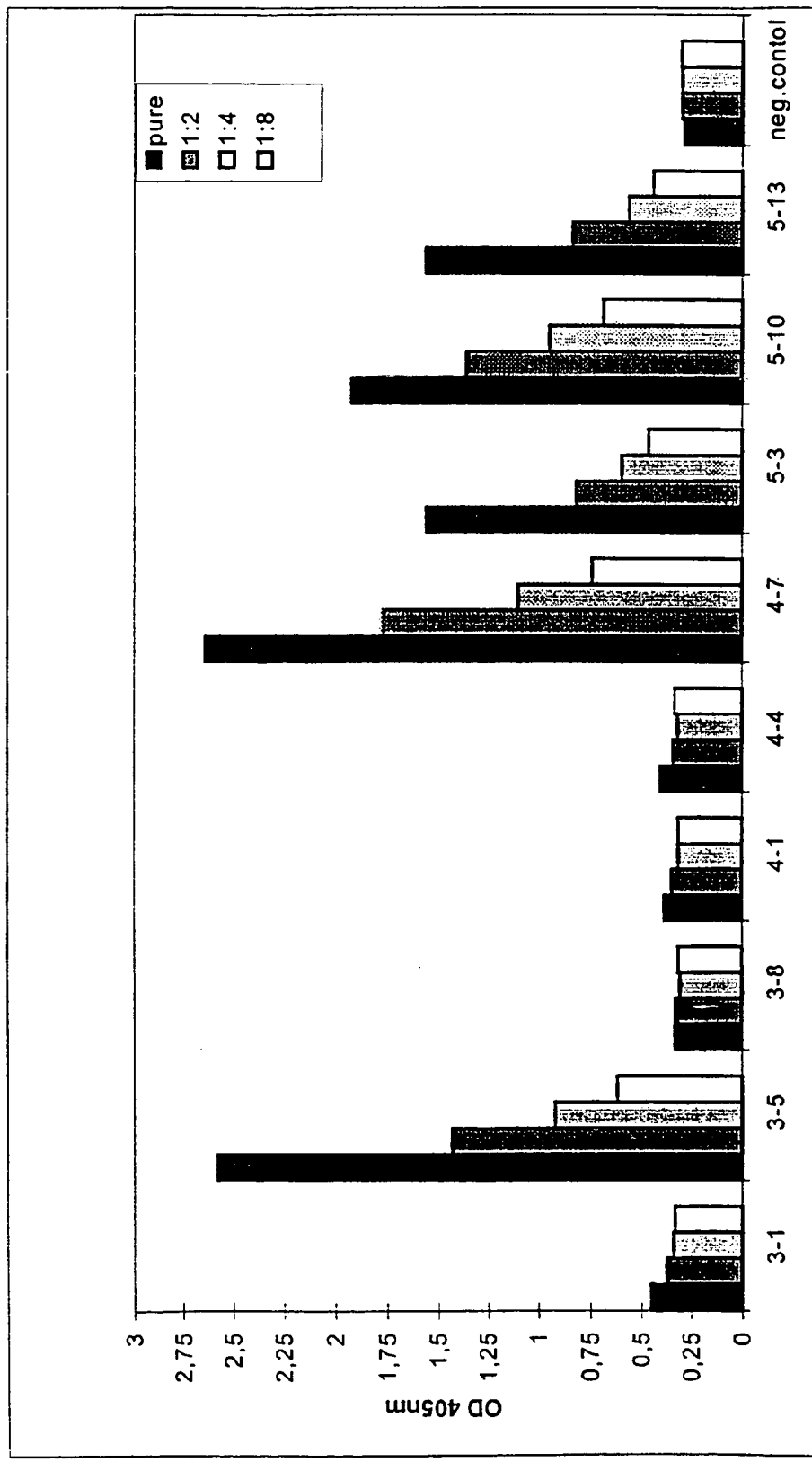

Figure 8.2

Figure 8.3
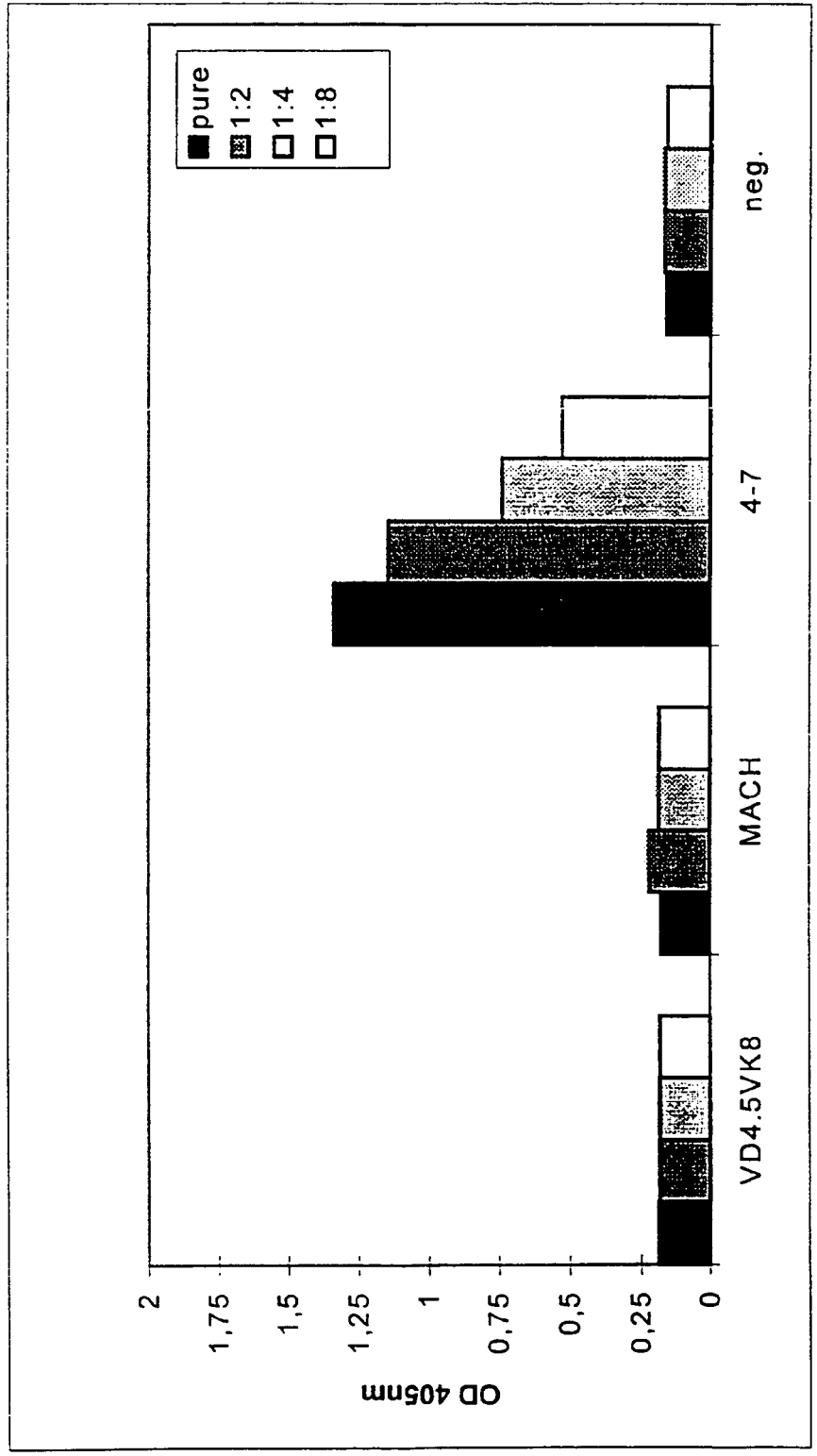

Figure 8.4
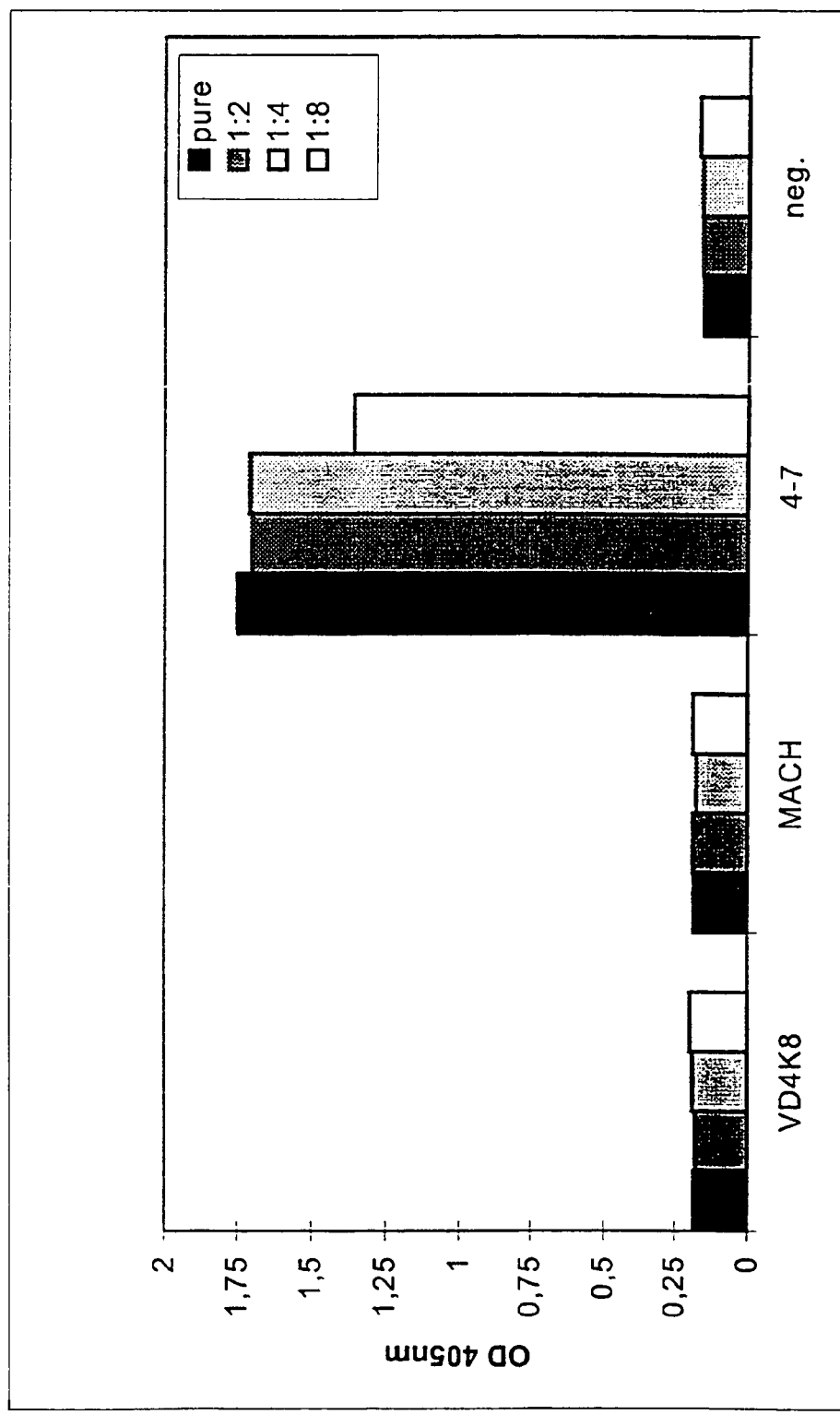

Figure 9.1
Part 1
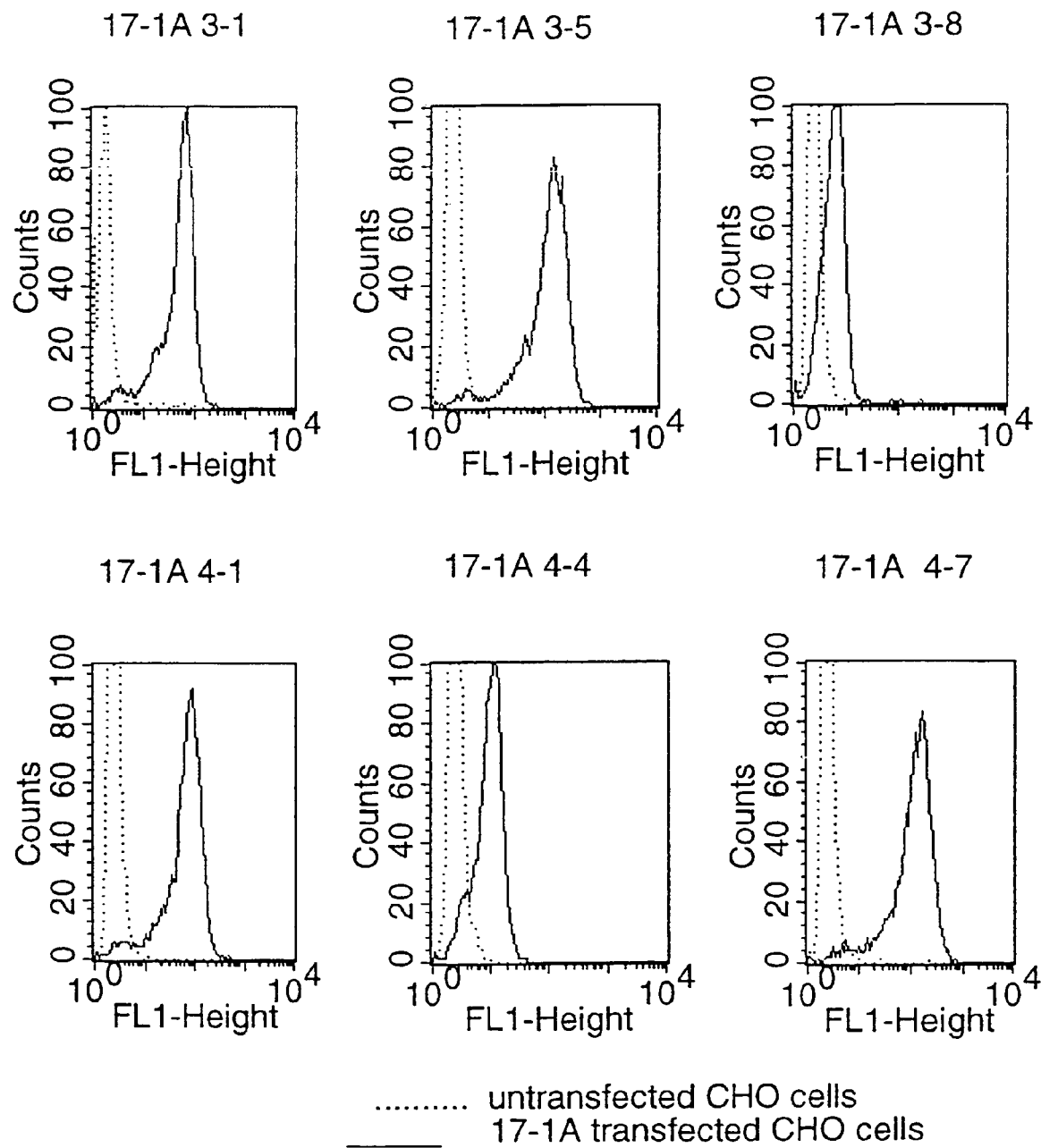

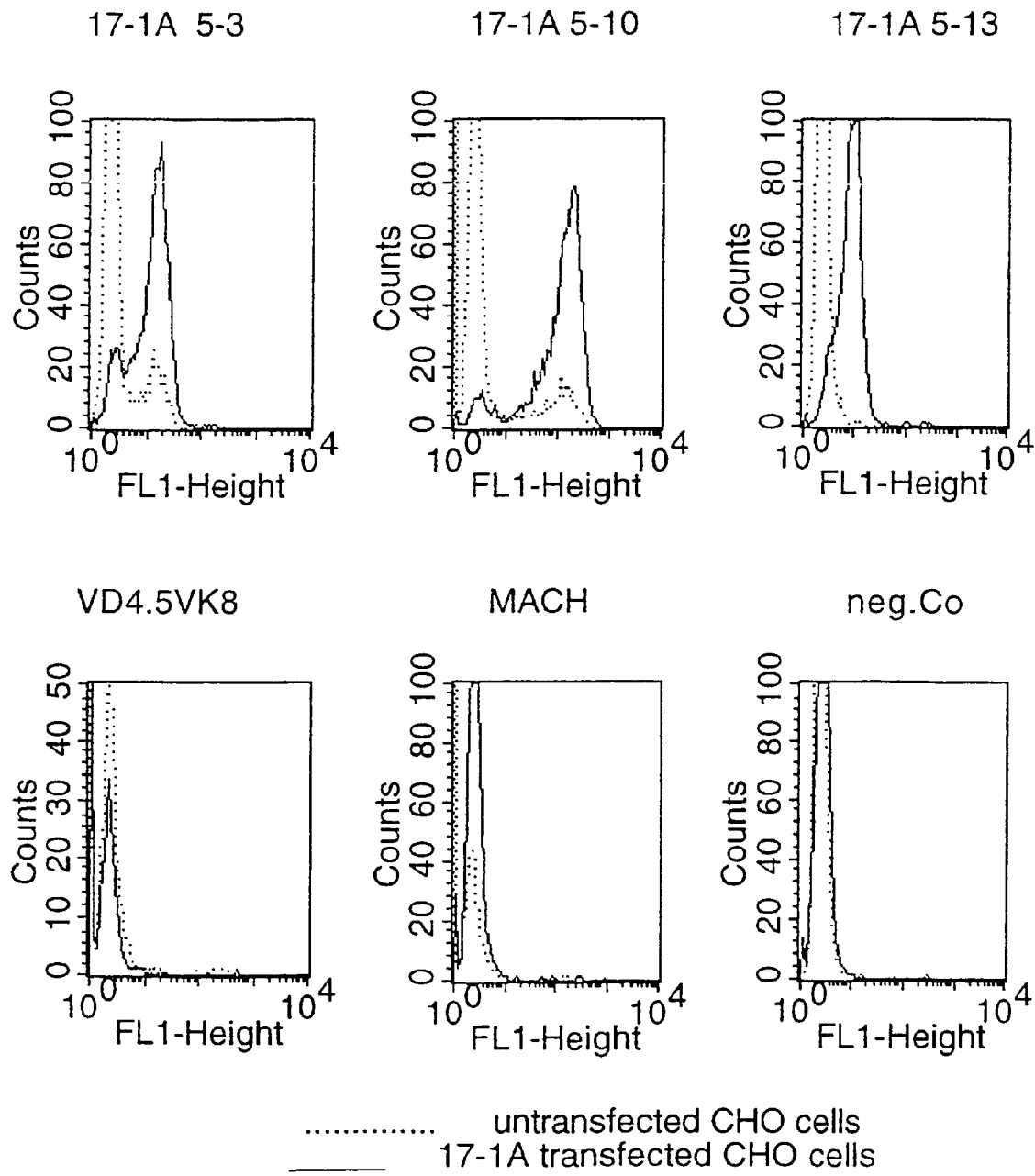

Figure 9.2
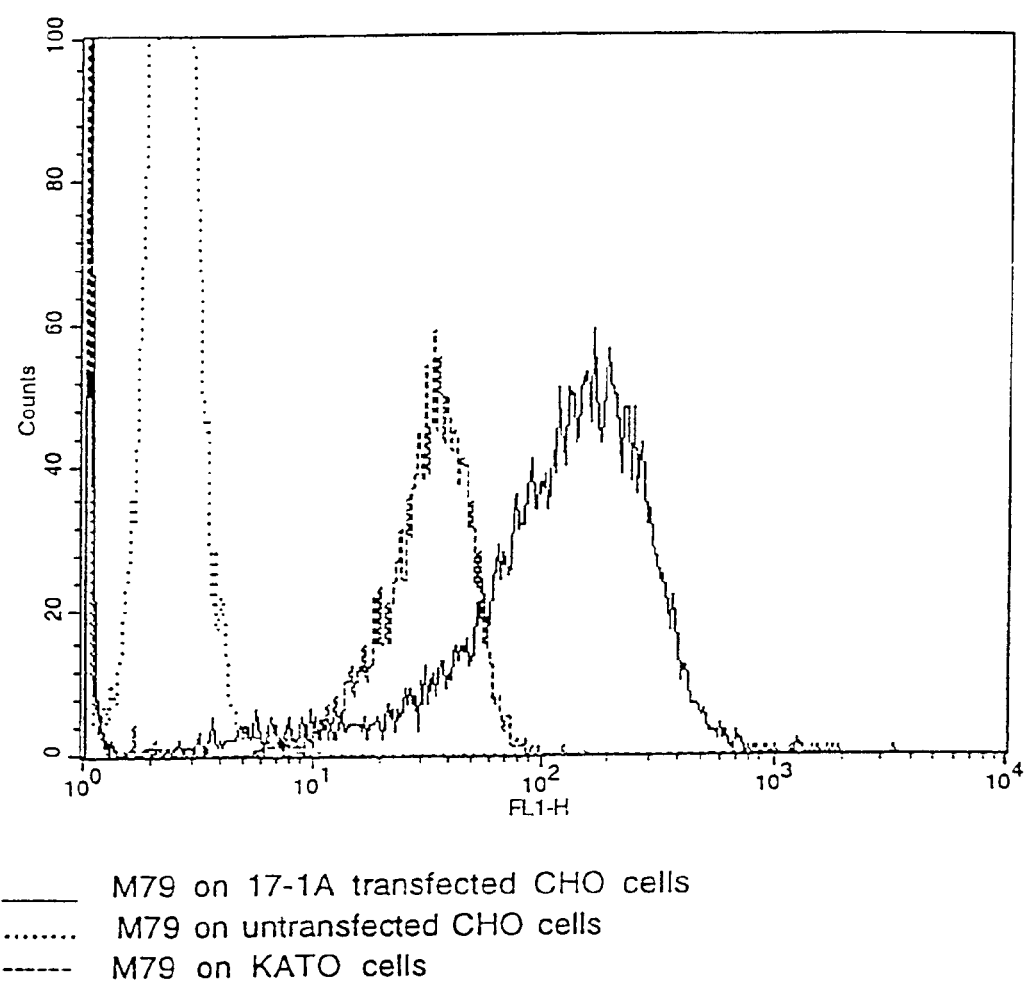
———— M79 on 17-1A transfected CHO cells
········ M79 on untransfected CHO cells
------ M79 on KATO cells

Figure 10

1) The Conventional approach

Randomly selected antigen-specific VH/VL-pairs that bind to their antigen as free or N-terminally located scFv-fragments or as whole antibody molecules Frequent loss of antigen binding after fusion of another protein domain to the N-terminus of the scFv-fragment

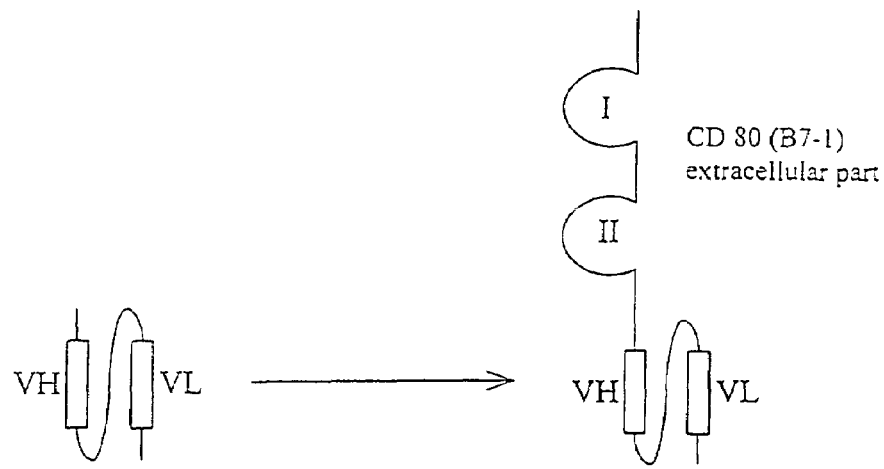

2) The method of invention

VH/VL-pairs selected by the method of the invention

High frequency of antigen binding after fusion of another protein domain to the N-terminus of the scFv-fragment

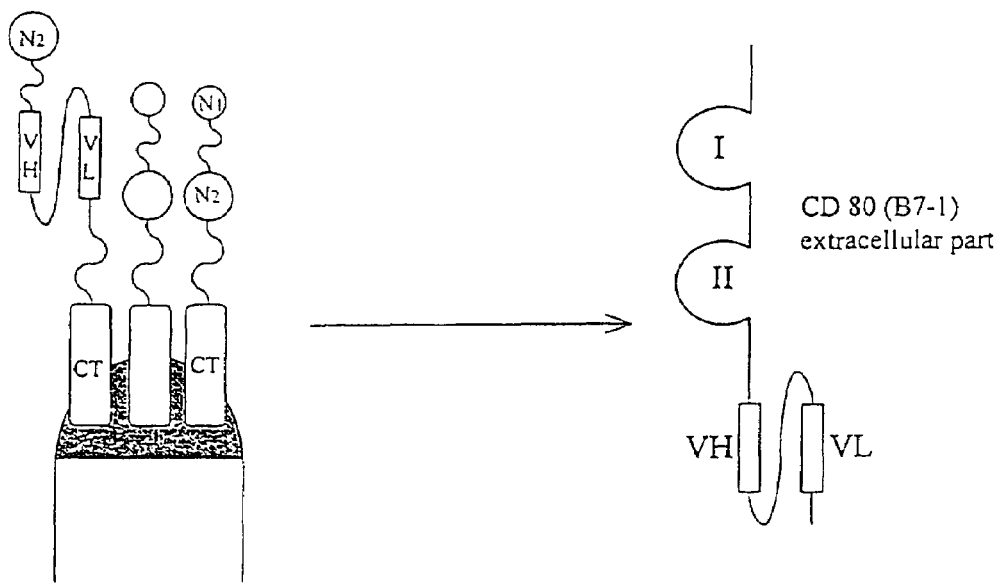

SEQUENCE LISTING

<160> NUMBER OF SEQ ID NOS: 77

<210> SEQ ID NO 1
<211> LENGTH: 33
<212> TYPE: DNA
<213> ORGANISM: Artificial Sequence

```
<220> FEATURE:
<223> OTHER INFORMATION: primer for human costimulatory protein CD80

<400> SEQUENCE: 1
gcagaattca ccatgggcca cacacggagg cag                                    33

<210> SEQ ID NO 2
<211> LENGTH: 34
<212> TYPE: DNA
<213> ORGANISM: Artificial Sequence
<220> FEATURE:
<223> OTHER INFORMATION: primer for human costimulatory protein CD80

<400> SEQUENCE: 2
tggtccggag ttatcaggaa aatgctcttg cttg                                   34

<210> SEQ ID NO 3
<211> LENGTH: 36
<212> TYPE: DNA
<213> ORGANISM: Artificial Sequence
<220> FEATURE:
<223> OTHER INFORMATION: primer for human CD80-M79scFv

<400> SEQUENCE: 3
aggtgtacac tccgatatcm arctgcagsa gtcwgg                                 36

<210> SEQ ID NO 4
<211> LENGTH: 37
<212> TYPE: DNA
<213> ORGANISM: Artificial Sequence
<220> FEATURE:
<223> OTHER INFORMATION: primer for single-chain Fv fragment (scFv) of
      the murine anti 17-1A antibody M74 V(L)

<400> SEQUENCE: 4
aggtgtacac tccgatatcc agctgaccca gtctcca                                37

<210> SEQ ID NO 5
<211> LENGTH: 51
<212> TYPE: DNA
<213> ORGANISM: Artificial Sequence
<220> FEATURE:
<223> OTHER INFORMATION: primer for single-chain Fv fragment (scFv) of
      the murine anti 17-1A antibody M74 V(L)

<400> SEQUENCE: 5
ggagccgccg ccgccagaac caccaccacc tttgatctcg agcttggtcc c                 51

<210> SEQ ID NO 6
<211> LENGTH: 96
<212> TYPE: DNA
<213> ORGANISM: Artificial Sequence
<220> FEATURE:
<223> OTHER INFORMATION: primer for single-chain Fv fragment (scFv) of
      the murine anti 17-1A antibody M74 V(H)

<400> SEQUENCE: 6
ggcggcggcg gctccggtgg tggtggttct caggtsmarc tgcagsagtc wggacctgag       60
ctggtgaagc ctggggcttc agtgaagatt cctgc                                  96

<210> SEQ ID NO 7
<211> LENGTH: 39
<212> TYPE: DNA
<213> ORGANISM: Artificial Sequence
```

-continued

```
<220> FEATURE:
<223> OTHER INFORMATION: primer for single-chain Fv fragment (scFv) of
      the murine anti 17-1A antibody M74 V(H)BspEI

<400> SEQUENCE: 7
aatccggagg agacggtgac cgtggtccct tggccccag                              39

<210> SEQ ID NO 8
<211> LENGTH: 69
<212> TYPE: DNA
<213> ORGANISM: Artificial Sequence
<220> FEATURE:
<223> OTHER INFORMATION: primer for single-chain Fv fragment (scFv) of
      the murine anti 17-1A antibody M74 V(H)

<400> SEQUENCE: 8
tccgatatcm arctgcagsa gtcwggacct gagctggtga agcctggggc ttcagtgaag      60
atttcctgc                                                              69

<210> SEQ ID NO 9
<211> LENGTH: 64
<212> TYPE: DNA
<213> ORGANISM: Artificial Sequence
<220> FEATURE:
<223> OTHER INFORMATION: primer for single-chain Fv fragment (scFv) of
      the murine anti 17-1A antibody M74 V(H)

<400> SEQUENCE: 9
ggagccgccg ccgccagaac caccaccacc tgaggagacg gtgaccgtgg tcccttggcc      60
ccag                                                                   64

<210> SEQ ID NO 10
<211> LENGTH: 54
<212> TYPE: DNA
<213> ORGANISM: Artificial Sequence
<220> FEATURE:
<223> OTHER INFORMATION: primer for single-chain Fv fragment (scFv) of
      the murine anti 17-1A antibody M74 V(L)

<400> SEQUENCE: 10
ggcggcggcg gctccggtgg tggtggttct gacattcagc tgacccagtc tcca           54

<210> SEQ ID NO 11
<211> LENGTH: 29
<212> TYPE: DNA
<213> ORGANISM: Artificial Sequence
<220> FEATURE:
<223> OTHER INFORMATION: primer for single-chain Fv fragment (scFv) of
      the murine anti 17-1A antibody M74 V(L)

<400> SEQUENCE: 11
aatccggatt tgatctcgag cttggtccc                                        29

<210> SEQ ID NO 12
<211> LENGTH: 22
<212> TYPE: DNA
<213> ORGANISM: Artificial Sequence
<220> FEATURE:
<223> OTHER INFORMATION: primer for V(H) chain of human anti-17-1A
      antibody

<400> SEQUENCE: 12
aggtgcagct gctcgagtct gg                                               22
```

```
<210> SEQ ID NO 13
<211> LENGTH: 17
<212> TYPE: DNA
<213> ORGANISM: Artificial Sequence
<220> FEATURE:
<223> OTHER INFORMATION: primer for V(H) chain of human anti-17-1A
      antibody

<400> SEQUENCE: 13
ctgaggagac ggtgacc                                                    17

<210> SEQ ID NO 14
<211> LENGTH: 38
<212> TYPE: DNA
<213> ORGANISM: Artificial Sequence
<220> FEATURE:
<223> OTHER INFORMATION: primer for V(L) chain of human anti-17-1A
      antibody

<400> SEQUENCE: 14
gagccgcacg agcccgagct cgtgwtgacr cagtctcc                             38

<210> SEQ ID NO 15
<211> LENGTH: 33
<212> TYPE: DNA
<213> ORGANISM: Artificial Sequence
<220> FEATURE:
<223> OTHER INFORMATION: primer for V(L) chain of human anti-17-1A
      antibody

<400> SEQUENCE: 15
gaagacacta gttgcagcca ccgtacgttt rat                                  33

<210> SEQ ID NO 16
<211> LENGTH: 24
<212> TYPE: DNA
<213> ORGANISM: Artificial Sequence
<220> FEATURE:
<223> OTHER INFORMATION: oligomer encoding six HIS residues

<400> SEQUENCE: 16
ctagccatca ccatcaccat caca                                            24

<210> SEQ ID NO 17
<211> LENGTH: 24
<212> TYPE: DNA
<213> ORGANISM: Artificial Sequence
<220> FEATURE:
<223> OTHER INFORMATION: oligomer encoding six HIS residues

<400> SEQUENCE: 17
ctagtgtgat ggtgatggtg atgg                                            24

<210> SEQ ID NO 18
<211> LENGTH: 47
<212> TYPE: DNA
<213> ORGANISM: Artificial Sequence
<220> FEATURE:
<223> OTHER INFORMATION: oligonucleotide for multiple cloning site
      containing SacI and XhoI overhang

<400> SEQUENCE: 18
gcagctggtc gacaaatccg gaggtggtgg atccgaggtg cagctgc                   47
```

<210> SEQ ID NO 19
<211> LENGTH: 55
<212> TYPE: DNA
<213> ORGANISM: Artificial Sequence
<220> FEATURE:
<223> OTHER INFORMATION: oligonucleotide for multiple cloning site
      containing SacI and XhoI overhang

<400> SEQUENCE: 19
tcgagcagct gcacctcgga tccaccacct ccggatttgt cgaccagctg cagct      55

<210> SEQ ID NO 20
<211> LENGTH: 79
<212> TYPE: DNA
<213> ORGANISM: Artificial Sequence
<220> FEATURE:
<223> OTHER INFORMATION: oligonucleotide containing multiple cloning
      sites

<400> SEQUENCE: 20
tcgagcccgg tcaccgtctc ctcaggtggt ggtggttctg gcggcggcgg ctccggtggt      60
ggtggttctg agctcggga      79

<210> SEQ ID NO 21
<211> LENGTH: 79
<212> TYPE: DNA
<213> ORGANISM: Artificial Sequence
<220> FEATURE:
<223> OTHER INFORMATION: oligonucleotide containing multiple cloning
      sites

<400> SEQUENCE: 21
ctagtcccga gctcagaacc accaccaccg gagccgccgc cgccagaacc accaccacct      60
gaggagacgg tgaccgggc      79

<210> SEQ ID NO 22
<211> LENGTH: 29
<212> TYPE: DNA
<213> ORGANISM: Artificial Sequence
<220> FEATURE:
<223> OTHER INFORMATION: primer for M13 gene III domain N2

<400> SEQUENCE: 22
ggtgtcgaca ctaaacctcc tgagtacgg      29

<210> SEQ ID NO 23
<211> LENGTH: 30
<212> TYPE: DNA
<213> ORGANISM: Artificial Sequence
<220> FEATURE:
<223> OTHER INFORMATION: primer for the M13 gene III domain N2

<400> SEQUENCE: 23
gcctccggaa gcattgacag gaggttgagg      30

<210> SEQ ID NO 24
<211> LENGTH: 33
<212> TYPE: DNA
<213> ORGANISM: Artificial Sequence
<220> FEATURE:
<223> OTHER INFORMATION: primer for detection of positive clones

<400> SEQUENCE: 24
gcagaattca ccatgggcca cacacggagg cag      33

```
<210> SEQ ID NO 25
<211> LENGTH: 39
<212> TYPE: DNA
<213> ORGANISM: Artificial Sequence
<220> FEATURE:
<223> OTHER INFORMATION: primer for detection of positive clones

<400> SEQUENCE: 25
tggtgcacta gtcgtacgtt tgatctcaag cttggtccc                    39

<210> SEQ ID NO 26
<211> LENGTH: 32
<212> TYPE: DNA
<213> ORGANISM: Artificial Sequence
<220> FEATURE:
<223> OTHER INFORMATION: primer for the extracellular region of the
      human CD54 antigen known as ICAM-1

<400> SEQUENCE: 26
ctcgaattca ctatggctcc cagcagcccc cg                           32

<210> SEQ ID NO 27
<211> LENGTH: 30
<212> TYPE: DNA
<213> ORGANISM: Artificial Sequence
<220> FEATURE:
<223> OTHER INFORMATION: primer for the extracellular region of the
      human CD54 antigen known as ICAM-1

<400> SEQUENCE: 27
gattccggac tcataccggg gggagagcac                              30

<210> SEQ ID NO 28
<211> LENGTH: 30
<212> TYPE: DNA
<213> ORGANISM: Artificial Sequence
<220> FEATURE:
<223> OTHER INFORMATION: primer for the extracellular region of human
      CD58

<400> SEQUENCE: 28
aatctagaac catggttgct gggagcgacg                              30

<210> SEQ ID NO 29
<211> LENGTH: 32
<212> TYPE: DNA
<213> ORGANISM: Artificial Sequence
<220> FEATURE:
<223> OTHER INFORMATION: primer for the extracellular region of human
      CD58

<400> SEQUENCE: 29
aagtccggat ctgtgtcttg aatgaccgct gc                           32

<210> SEQ ID NO 30
<211> LENGTH: 32
<212> TYPE: DNA
<213> ORGANISM: Artificial Sequence
<220> FEATURE:
<223> OTHER INFORMATION: primer for the extracellular region of human
      CD86 costimulatory protein

<400> SEQUENCE: 30
aagtctagaa aatggatccc cagtgcacta tg                           32
```

<210> SEQ ID NO 31
<211> LENGTH: 34
<212> TYPE: DNA
<213> ORGANISM: Artificial Sequence
<220> FEATURE:
<223> OTHER INFORMATION: primer for the extracellular region of human
      CD86 costimulatory protein

<400> SEQUENCE: 31
aattccggat gggggaggct gagggtcctc aagc                              34

<210> SEQ ID NO 32
<211> LENGTH: 27
<212> TYPE: DNA
<213> ORGANISM: Artificial Sequence
<220> FEATURE:
<223> OTHER INFORMATION: primers for murine V heavy chain

<400> SEQUENCE: 32
saggtgcagc tcgaggagtc aggacct                                     27

<210> SEQ ID NO 33
<211> LENGTH: 27
<212> TYPE: DNA
<213> ORGANISM: Artificial Sequence
<220> FEATURE:
<223> OTHER INFORMATION: primers for murine V heavy chain

<400> SEQUENCE: 33
gaggtccagc tcgagcagtc tggacct                                     27

<210> SEQ ID NO 34
<211> LENGTH: 27
<212> TYPE: DNA
<213> ORGANISM: Artificial Sequence
<220> FEATURE:
<223> OTHER INFORMATION: primers for murine V heavy chain

<400> SEQUENCE: 34
caggtccaac tcgagcagcc tggggct                                     27

<210> SEQ ID NO 35
<211> LENGTH: 27
<212> TYPE: DNA
<213> ORGANISM: Artificial Sequence
<220> FEATURE:
<223> OTHER INFORMATION: primers for murine V heavy chain

<400> SEQUENCE: 35
gaggttcagc tcgagcagtc tggggca                                     27

<210> SEQ ID NO 36
<211> LENGTH: 27
<212> TYPE: DNA
<213> ORGANISM: Artificial Sequence
<220> FEATURE:
<223> OTHER INFORMATION: primers for murine V heavy chain

<400> SEQUENCE: 36
gargtgaagc tcgaggagtc tggagga                                     27

<210> SEQ ID NO 37
<211> LENGTH: 27
<212> TYPE: DNA
<213> ORGANISM: Artificial Sequence
<220> FEATURE:
<223> OTHER INFORMATION: primers for murine V heavy chain

```
<400> SEQUENCE: 37
gaggtgaagc ttctcgagtc tggaggt                                    27

<210> SEQ ID NO 38
<211> LENGTH: 27
<212> TYPE: DNA
<213> ORGANISM: Artificial Sequence
<220> FEATURE:
<223> OTHER INFORMATION: primers for murine V heavy chain

<400> SEQUENCE: 38
gaagtgaagc tcgaggagtc tggggga                                    27

<210> SEQ ID NO 39
<211> LENGTH: 27
<212> TYPE: DNA
<213> ORGANISM: Artificial Sequence
<220> FEATURE:
<223> OTHER INFORMATION: primers for murine V heavy chain

<400> SEQUENCE: 39
gaggttcagc tcgagcagtc tggagct                                    27

<210> SEQ ID NO 40
<211> LENGTH: 34
<212> TYPE: DNA
<213> ORGANISM: Artificial Sequence
<220> FEATURE:
<223> OTHER INFORMATION: primers for murine V heavy chain

<400> SEQUENCE: 40
tgaggagacg gtgaccgtgg tcccttggcc ccag                            34

<210> SEQ ID NO 41
<211> LENGTH: 32
<212> TYPE: DNA
<213> ORGANISM: Artificial Sequence
<220> FEATURE:
<223> OTHER INFORMATION: primer for murine V kappa chain

<400> SEQUENCE: 41
ccagttccga gctcgttgtg actcaggaat ct                              32

<210> SEQ ID NO 42
<211> LENGTH: 32
<212> TYPE: DNA
<213> ORGANISM: Artificial Sequence
<220> FEATURE:
<223> OTHER INFORMATION: primer for murine V kappa chain

<400> SEQUENCE: 42
ccagttccga gctcgtgttg acgcagccgc cc                              32

<210> SEQ ID NO 43
<211> LENGTH: 32
<212> TYPE: DNA
<213> ORGANISM: Artificial Sequence
<220> FEATURE:
<223> OTHER INFORMATION: primer for murine V kappa chain

<400> SEQUENCE: 43
ccagttccga gctcgtgctc acccagtctc ca                              32
```

<210> SEQ ID NO 44
<211> LENGTH: 32
<212> TYPE: DNA
<213> ORGANISM: Artificial Sequence
<220> FEATURE:
<223> OTHER INFORMATION: primer for murine V kappa chain

<400> SEQUENCE: 44
ccagttccga gctccagatg acccagtctc ca          32

<210> SEQ ID NO 45
<211> LENGTH: 32
<212> TYPE: DNA
<213> ORGANISM: Artificial Sequence
<220> FEATURE:
<223> OTHER INFORMATION: primer for murine V kappa chain

<400> SEQUENCE: 45
ccagatgtga gctcgtgatg acccagactc ca          32

<210> SEQ ID NO 46
<211> LENGTH: 32
<212> TYPE: DNA
<213> ORGANISM: Artificial Sequence
<220> FEATURE:
<223> OTHER INFORMATION: primer for murine V kappa chain

<400> SEQUENCE: 46
ccagatgtga gctcgtcatg acccagtctc ca          32

<210> SEQ ID NO 47
<211> LENGTH: 32
<212> TYPE: DNA
<213> ORGANISM: Artificial Sequence
<220> FEATURE:
<223> OTHER INFORMATION: primer for murine V kappa chain

<400> SEQUENCE: 47
ccagttccga gctcgtgatg acacagtctc ca          32

<210> SEQ ID NO 48
<211> LENGTH: 39
<212> TYPE: DNA
<213> ORGANISM: Artificial Sequence
<220> FEATURE:
<223> OTHER INFORMATION: primer for murine V kappa chain

<400> SEQUENCE: 48
tggtgcacta gtcgtacgtt tgatctcaag cttggtccc          39

<210> SEQ ID NO 49
<211> LENGTH: 67
<212> TYPE: DNA
<213> ORGANISM: Artificial Sequence
<220> FEATURE:
<223> OTHER INFORMATION: oligonucleotide for the multiple cloning site

<400> SEQUENCE: 49
ctagaattct tcgaatccgg aggtggtgga tccgatatcc ccgggcatca tcaccatcat          60
cattgag          67

<210> SEQ ID NO 50
<211> LENGTH: 42
<212> TYPE: DNA
<213> ORGANISM: Artificial Sequence

```
<220> FEATURE:
<223> OTHER INFORMATION: sequence of double-stranded oligonucleotide
      designated ACCGS1BAM

<400> SEQUENCE: 50
ccggaggtgg tggttccggg ggtggaggtt caggcggtgg tg                          42

<210> SEQ ID NO 51
<211> LENGTH: 42
<212> TYPE: DNA
<213> ORGANISM: Artificial Sequence
<220> FEATURE:
<223> OTHER INFORMATION: sequence of double-stranded oligonucleotide
      designated ACCGS15BAM

<400> SEQUENCE: 51
gatccaccac cgcctgaacc tccacccccg gaaccaccac ct                          42

<210> SEQ ID NO 52
<211> LENGTH: 14
<212> TYPE: PRT
<213> ORGANISM: Artificial Sequence
<220> FEATURE:
<223> OTHER INFORMATION: peptide encoded by synthetic oligonucleotide

<400> SEQUENCE: 52

Gly Gly Gly Gly Ser Gly Gly Gly Gly Ser Gly Gly Gly Gly
1               5                   10

<210> SEQ ID NO 53
<211> LENGTH: 381
<212> TYPE: DNA
<213> ORGANISM: Homo sapiens
<220> FEATURE:
<221> NAME/KEY: CDS
<222> LOCATION: (1)..(381)
<223> OTHER INFORMATION:

<400> SEQUENCE: 53 gag gtg cag ctg ctc gag tct ggg gga ggc gtg gtc cag cct ggg agg        48
Glu Val Gln Leu Leu Glu Ser Gly Gly Gly Val Val Gln Pro Gly Arg
1               5                   10                  15 tcc ctg aga ctc tcc tgt gca gcc tct gga ttc acc ttc agt agc tat        96
Ser Leu Arg Leu Ser Cys Ala Ala Ser Gly Phe Thr Phe Ser Ser Tyr
            20                  25                  30 ggc atg cac tgg gtc cgc cag gct cca ggc aag ggg ctg gag tgg gtg        144
Gly Met His Trp Val Arg Gln Ala Pro Gly Lys Gly Leu Glu Trp Val
        35                  40                  45 gca gtt ata tca tat gat gga agt aat aaa tac tat gca gac tcc gtg        192
Ala Val Ile Ser Tyr Asp Gly Ser Asn Lys Tyr Tyr Ala Asp Ser Val
    50                  55                  60 aag ggc cga ttc acc atc tcc aga gac aat tcc aag aac acg ctg tat        240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tac tgt        288
Leu Gln Met Asn Ser Leu Arg Ala Glu Asp Thr Ala Val Tyr Tyr Cys
                85                  90                  95 gcg aaa gat atg ggg tgg ggc agt ggc tgg aga ccc tac tac tac tac        336
Ala Lys Asp Met Gly Trp Gly Ser Gly Trp Arg Pro Tyr Tyr Tyr Tyr
            100                 105                 110 ggt atg gac gtc tgg ggc caa ggg acc acg gtc acc gtc tcc tca            381
Gly Met Asp Val Trp Gly Gln Gly Thr Thr Val Thr Val Ser Ser
        115                 120                 125
```

```
<210> SEQ ID NO 54
<211> LENGTH: 127
<212> TYPE: PRT
<213> ORGANISM: Homo sapiens

<400> SEQUENCE: 54

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Met Gly Trp Gly Ser Gly Trp Arg Pro Tyr Tyr Tyr Tyr
            100                 105                 110

Gly Met Asp Val Trp Gly Gln Gly Thr Thr Val Thr Val Ser Ser
        115                 120                 125

<210> SEQ ID NO 55
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION:

<400> SEQUENCE: 55 gag ctc cag atg acc cag tct cca tcc tcc ctg tct gct tct gtg gga      48
Glu Leu Gln Met Thr Gln Ser Pro Ser Ser Leu Ser Ala Ser Val Gly
1               5                   10                  15 gac aga gtc acc atc act tgt cgg aca agt cag agc att agc agc tat      96
Asp Arg Val Thr Ile Thr Cys Arg Thr Ser Gln Ser Ile Ser Ser Tyr
            20                  25                  30 tta aat tgg tat cag cag aaa cca gga cag cct cct aag ctg ctc att     144
Leu Asn Trp Tyr Gln Gln Lys Pro Gly Gln Pro Pro Lys Leu Leu Ile
        35                  40                  45 tac tgg gca tct acc cgg gaa tcc ggg gtc cct gac cga ttc agt ggc     192
Tyr Trp Ala Ser Thr Arg Glu Ser Gly Val Pro Asp Arg Phe Ser Gly
    50                  55                  60 agc ggg tct ggg aca gat ttc act ctc acc atc agc agt cta caa cct     240
Ser Gly Ser Gly Thr Asp Phe Thr Leu Thr Ile Ser Ser Leu Gln Pro
65                  70                  75                  80 gaa gat tct gca act tac tac tgt cag cag agt tac gac atc ccg tac     288
Glu Asp Ser Ala Thr Tyr Tyr Cys Gln Gln Ser Tyr Asp Ile Pro Tyr
                85                  90                  95 act ttt ggc cag ggg acc aag ctg gag atc aaa                         321
Thr Phe Gly Gln Gly Thr Lys Leu Glu Ile Lys
            100                 105

<210> SEQ ID NO 56
<211> LENGTH: 107
<212> TYPE: PRT
<213> ORGANISM: Homo sapiens
```

```
<400> SEQUENCE: 56

Glu Leu Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Ser Tyr
            20                  25                  30

Leu Asn Trp Tyr Gln Gln Lys Pro Gly Gln Pro Pro Lys Leu Leu Ile
        35                  40                  45

Tyr Trp Ala Ser Thr Arg Glu Ser Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ser Tyr Asp Ile Pro Tyr
                85                  90                  95

Thr Phe Gly Gln Gly Thr Lys Leu Glu Ile Lys
            100                 105

<210> SEQ ID NO 57
<211> LENGTH: 201
<212> TYPE: DNA
<213> ORGANISM: Artificial Sequence
<220> FEATURE:
<223> OTHER INFORMATION: sequence designated L-F-NS3Frame (Figure 3.4)

<400> SEQUENCE: 57
ccgctctaga attccaccat gggatggagc tgtatcatcc tcttcttggt agcaacagct      60
acaggtgtcc actccgacta caaagatgat gacgataagg atatcttcgg aggtggtggt    120
agcgctattc catatggacg tcccgctcga ggtcgtccat catcaccatc atcactgagc    180
ggccgctcta gagtcgacct c                                              201

<210> SEQ ID NO 58
<211> LENGTH: 526
<212> TYPE: DNA
<213> ORGANISM: Artificial Sequence
<220> FEATURE:
<223> OTHER INFORMATION: M13-Phage and artificial sequence of the MCS
<221> NAME/KEY: CDS
<222> LOCATION: (19)..(429)
<223> OTHER INFORMATION:

<400> SEQUENCE: 58
gagctgcagc tggtcgac act aaa cct cct gag tac ggt gat aca cct att       51
              Thr Lys Pro Pro Glu Tyr Gly Asp Thr Pro Ile
                1               5                   10 ccg ggc tat act tat atc aac cct ctc gac ggc act tat ccg cct ggt       99
Pro Gly Tyr Thr Tyr Ile Asn Pro Leu Asp Gly Thr Tyr Pro Pro Gly
            15                  20                  25 act gag caa aac ccc gct aat cct aat cct tct ctt gag gag tct cag      147
Thr Glu Gln Asn Pro Ala Asn Pro Asn Pro Ser Leu Glu Glu Ser Gln
        30                  35                  40 cct ctt aat act ttc atg ttt cag aat aat agg ttc cga aat agg cag      195
Pro Leu Asn Thr Phe Met Phe Gln Asn Asn Arg Phe Arg Asn Arg Gln
    45                  50                  55 ggg gca tta act gtt tat acg ggc act gtt act caa ggc act gac ccc      243
Gly Ala Leu Thr Val Tyr Thr Gly Thr Val Thr Gln Gly Thr Asp Pro
60                  65                  70                  75 gtt aaa act tat tac cag tac act cct gta tca tca aaa gcc atg tat      291
Val Lys Thr Tyr Tyr Gln Tyr Thr Pro Val Ser Ser Lys Ala Met Tyr
                80                  85                  90
```

```
gac gct tac tgg aac ggt aaa ttc aga gac tgc gct ttc cat tct ggc      339
Asp Ala Tyr Trp Asn Gly Lys Phe Arg Asp Cys Ala Phe His Ser Gly
            95                  100                 105 ttt aat gag gat cca ttc gtt tgt gaa tat caa ggc caa tcg tct gac      387
Phe Asn Glu Asp Pro Phe Val Cys Glu Tyr Gln Gly Gln Ser Ser Asp
        110                 115                 120 ctg cct caa cct cct gtc aat gct tcc gga ggt ggt gga tcc              429
Leu Pro Gln Pro Pro Val Asn Ala Ser Gly Gly Gly Gly Ser
    125                 130                 135 gaggtgcagc tgctcgagcc cggtcaccgt ctcctcaggt ggtggtggtt ctggcggcgg    489
cggctccggt ggtggtggtt ctgagctcgg gactagt                             526

<210> SEQ ID NO 59
<211> LENGTH: 137
<212> TYPE: PRT
<213> ORGANISM: Artificial Sequence
<220> FEATURE:
<223> OTHER INFORMATION: M13-Phage and artificial sequence of the MCS

<400> SEQUENCE: 59

Thr Lys Pro Pro Glu Tyr Gly Asp Thr Pro Ile Pro Gly Tyr Thr Tyr
1               5                   10                  15

Ile Asn Pro Leu Asp Gly Thr Tyr Pro Pro Gly Thr Glu Gln Asn Pro
            20                  25                  30

Ala Asn Pro Asn Pro Ser Leu Glu Glu Ser Gln Pro Leu Asn Thr Phe
        35                  40                  45

Met Phe Gln Asn Asn Arg Phe Arg Asn Arg Gln Gly Ala Leu Thr Val
    50                  55                  60

Tyr Thr Gly Thr Val Thr Gln Gly Thr Asp Pro Val Lys Thr Tyr Tyr
65                  70                  75                  80

Gln Tyr Thr Pro Val Ser Ser Lys Ala Met Tyr Asp Ala Tyr Trp Asn
                85                  90                  95

Gly Lys Phe Arg Asp Cys Ala Phe His Ser Gly Phe Asn Glu Asp Pro
            100                 105                 110

Phe Val Cys Glu Tyr Gln Gly Gln Ser Ser Asp Leu Pro Gln Pro Pro
        115                 120                 125

Val Asn Ala Ser Gly Gly Gly Gly Ser
    130                 135

<210> SEQ ID NO 60
<211> LENGTH: 726
<212> TYPE: DNA
<213> ORGANISM: Mus sp.
<220> FEATURE:
<221> NAME/KEY: CDS
<222> LOCATION: (1)..(726)
<223> OTHER INFORMATION:

<400> SEQUENCE: 60 gag gtg cag ctg ctc gag cag tct gga gct gag ctg gtg aaa cct ggg      48
Glu Val Gln Leu Leu Glu Gln Ser Gly Ala Glu Leu Val Lys Pro Gly
1               5                   10                  15 gcc tca gtg aag ata tcc tgc aag gct tct gga tac gcc ttc act aac      96
Ala Ser Val Lys Ile Ser Cys Lys Ala Ser Gly Tyr Ala Phe Thr Asn
            20                  25                  30 tac tgg cta ggt tgg gta aag cag agg cct gga cat gga ctt gag tgg     144
Tyr Trp Leu Gly Trp Val Lys Gln Arg Pro Gly His Gly Leu Glu Trp
        35                  40                  45
```

```
att gga gat ctt ttc cct gga agt ggt aat act cac tac aat gag agg      192
Ile Gly Asp Leu Phe Pro Gly Ser Gly Asn Thr His Tyr Asn Glu Arg
     50                  55                  60 ttc agg ggc aaa gcc aca ctg act gca gac aaa tcc tcg agc aca gcc      240
Phe Arg Gly Lys Ala Thr Leu Thr Ala Asp Lys Ser Ser Ser Thr Ala
 65                  70                  75                  80 ttt atg cag ctc agt agc ctg aca tct gag gac tct gct gtc tat ttc      288
Phe Met Gln Leu Ser Ser Leu Thr Ser Glu Asp Ser Ala Val Tyr Phe
                 85                  90                  95 tgt gca aga ttg agg aac tgg gac gag gct atg gac tac tgg ggc caa      336
Cys Ala Arg Leu Arg Asn Trp Asp Glu Ala Met Asp Tyr Trp Gly Gln
            100                 105                 110 ggg acc acg gtc acc gtc tcc tca ggt ggt ggt ggt tct ggc ggc ggc      384
Gly Thr Thr Val Thr Val Ser Ser Gly Gly Gly Gly Ser Gly Gly Gly
        115                 120                 125 ggc tcc ggt ggt ggt ggt tct gag ctc gtc atg acc cag tct cca tct      432
Gly Ser Gly Gly Gly Gly Ser Glu Leu Val Met Thr Gln Ser Pro Ser
    130                 135                 140 tat ctt gct gca tct cct gga gaa acc att act att aat tgc agg gca      480
Tyr Leu Ala Ala Ser Pro Gly Glu Thr Ile Thr Ile Asn Cys Arg Ala
145                 150                 155                 160 agt aag agc att agc aaa tat tta gcc tgg tat caa gag aaa cct ggg      528
Ser Lys Ser Ile Ser Lys Tyr Leu Ala Trp Tyr Gln Glu Lys Pro Gly
                165                 170                 175 aaa act aat aag ctt ctt atc tac tct gga tcc act ttg caa tct gga      576
Lys Thr Asn Lys Leu Leu Ile Tyr Ser Gly Ser Thr Leu Gln Ser Gly
            180                 185                 190 att cca tca agg ttc agt ggc agt gga tct ggt aca gat ttc act ctc      624
Ile Pro Ser Arg Phe Ser Gly Ser Gly Ser Gly Thr Asp Phe Thr Leu
        195                 200                 205 acc atc agt agc ctg gag cct gaa gat ttt gca atg tat tac tgt caa      672
Thr Ile Ser Ser Leu Glu Pro Glu Asp Phe Ala Met Tyr Tyr Cys Gln
    210                 215                 220 cag cat aat gaa tat ccg tac acg ttc gga ggg ggg acc aag ctt gag      720
Gln His Asn Glu Tyr Pro Tyr Thr Phe Gly Gly Gly Thr Lys Leu Glu
225                 230                 235                 240 atc aaa                                                              726
Ile Lys
```

```
<210> SEQ ID NO 61
<211> LENGTH: 242
<212> TYPE: PRT
<213> ORGANISM: Mus sp.

<400> SEQUENCE: 61
```

```
Glu Val Gln Leu Leu Glu Gln Ser Gly Ala Glu Leu Val Lys Pro Gly
 1               5                  10                  15

Ala Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Ile Gly Asp Leu Phe Pro Gly Ser Gly Asn Thr His Tyr Asn Glu Arg
     50                  55                  60

Phe Arg Gly Lys Ala Thr Leu Thr Ala Asp Lys Ser Ser Ser Thr Ala
 65                  70                  75                  80

Phe Met Gln Leu Ser Ser Leu Thr Ser Glu Asp Ser Ala Val Tyr Phe
                 85                  90                  95

Cys Ala Arg Leu Arg Asn Trp Asp Glu Ala Met Asp Tyr Trp Gly Gln
            100                 105                 110
```

```
Gly Thr Thr Val Thr Val Ser Ser Gly Gly Gly Ser Gly Gly Gly
            115                 120                 125

Gly Ser Gly Gly Gly Ser Glu Leu Val Met Thr Gln Ser Pro Ser
130                 135                 140

Tyr Leu Ala Ala Ser Pro Gly Glu Thr Ile Thr Ile Asn Cys Arg Ala
145                 150                 155                 160

Ser Lys Ser Ile Ser Lys Tyr Leu Ala Trp Tyr Gln Glu Lys Pro Gly
                165                 170                 175

Lys Thr Asn Lys Leu Leu Ile Tyr Ser Gly Ser Thr Leu Gln Ser Gly
            180                 185                 190

Ile Pro Ser Arg Phe Ser Gly Ser Gly Ser Gly Thr Asp Phe Thr Leu
        195                 200                 205

Thr Ile Ser Ser Leu Glu Pro Glu Asp Phe Ala Met Tyr Tyr Cys Gln
210                 215                 220

Gln His Asn Glu Tyr Pro Tyr Thr Phe Gly Gly Gly Thr Lys Leu Glu
225                 230                 235                 240

Ile Lys

<210> SEQ ID NO 62
<211> LENGTH: 753
<212> TYPE: DNA
<213> ORGANISM: Mus sp.
<220> FEATURE:
<221> NAME/KEY: CDS
<222> LOCATION: (1)..(753)
<223> OTHER INFORMATION:

<400> SEQUENCE: 62 gag gtg cag ctg ctc gag cag tct gga gct gag ctg gta agg cct ggg      48
Glu Val Gln Leu Leu Glu Gln Ser Gly Ala Glu Leu Val Arg Pro Gly
1               5                   10                  15 act tca gtg aag ctg tcc tgc aag gct tct ggc tac acc ttc aca agc      96
Thr Ser Val Lys Leu Ser Cys Lys Ala Ser Gly Tyr Thr Phe Thr Ser
            20                  25                  30 tat ggt tta agc tgg gtg aag cag aga act gga cag ggc ctt gag tgg     144
Tyr Gly Leu Ser Trp Val Lys Gln Arg Thr Gly Gln Gly Leu Glu Trp
        35                  40                  45 att gga gag gtt tat cct aga att ggt aat gct tac tac aat gag aag     192
Ile Gly Glu Val Tyr Pro Arg Ile Gly Asn Ala Tyr Tyr Asn Glu Lys
    50                  55                  60 ttc aag ggc aag gcc aca ctg act gca gac aaa tcc tcc agc aca gcg     240
Phe Lys Gly Lys Ala Thr Leu Thr Ala Asp Lys Ser Ser Ser Thr Ala
65                  70                  75                  80 tcc atg gag ctc cgc agc ctg aca tct gag gac tct gcg gtc tat ttc     288
Ser Met Glu Leu Arg Ser Leu Thr Ser Glu Asp Ser Ala Val Tyr Phe
                85                  90                  95 tgt gca aga cgg gga tcc tac ggt agt aac tac gac tgg tac ttc gat     336
Cys Ala Arg Arg Gly Ser Tyr Gly Ser Asn Tyr Asp Trp Tyr Phe Asp
            100                 105                 110 gtc tgg ggc caa ggg acc acg gtc acc gtc tcc tca ggt ggt ggt ggt     384
Val Trp Gly Gln Gly Thr Thr Val Thr Val Ser Ser Gly Gly Gly Gly
        115                 120                 125 tct ggc ggc ggc ggc tcc ggt ggt ggt ggt tct gag ctc gtg atg acc     432
Ser Gly Gly Gly Gly Ser Gly Gly Gly Gly Ser Glu Leu Val Met Thr
    130                 135                 140 cag act cca ctc tcc ctg cct gtc agt ctt gga gat caa gcc tcc atc     480
Gln Thr Pro Leu Ser Leu Pro Val Ser Leu Gly Asp Gln Ala Ser Ile
145                 150                 155                 160
```

```
tct tgc aga tct agt cag agc ctt gta cac agt aat gga aac acc tat    528
Ser Cys Arg Ser Ser Gln Ser Leu Val His Ser Asn Gly Asn Thr Tyr
            165                 170                 175 tta cat tgg tac ctg cag aag cca ggc cag tct cca aag ctc ctg atc    576
Leu His Trp Tyr Leu Gln Lys Pro Gly Gln Ser Pro Lys Leu Leu Ile
        180                 185                 190 tac aaa gtt tcc aac cga ttt tct ggg gtc cca gac agg ttc agt ggc    624
Tyr Lys Val Ser Asn Arg Phe Ser Gly Val Pro Asp Arg Phe Ser Gly
    195                 200                 205 agt gga tca ggg aca gat ttc aca ctc aag atc agc aga gtg gag gct    672
Ser Gly Ser Gly Thr Asp Phe Thr Leu Lys Ile Ser Arg Val Glu Ala
210                 215                 220 gag gat ctg gga gtt tat ttc tgc tct caa agt aca cat gtt ccg tac    720
Glu Asp Leu Gly Val Tyr Phe Cys Ser Gln Ser Thr His Val Pro Tyr
225                 230                 235                 240 acg ttc gga ggg ggg acc aag ctt gag atc aaa                        753
Thr Phe Gly Gly Gly Thr Lys Leu Glu Ile Lys
                245                 250

<210> SEQ ID NO 63
<211> LENGTH: 251
<212> TYPE: PRT
<213> ORGANISM: Mus sp.

<400> SEQUENCE: 63

Glu Val Gln Leu Leu Glu Gln Ser Gly Ala Glu Leu Val Arg Pro Gly
1               5                   10                  15

Thr Ser Val Lys Leu Ser Cys Lys Ala Ser Gly Tyr Thr Phe Thr Ser
            20                  25                  30

Tyr Gly Leu Ser Trp Val Lys Gln Arg Thr Gly Gln Gly Leu Glu Trp
        35                  40                  45

Ile Gly Glu Val Tyr Pro Arg Ile Gly Asn Ala Tyr Tyr Asn Glu Lys
    50                  55                  60

Phe Lys Gly Lys Ala Thr Leu Thr Ala Asp Lys Ser Ser Ser Thr Ala
65                  70                  75                  80

Ser Met Glu Leu Arg Ser Leu Thr Ser Glu Asp Ser Ala Val Tyr Phe
                85                  90                  95

Cys Ala Arg Arg Gly Ser Tyr Gly Ser Asn Tyr Asp Trp Tyr Phe Asp
            100                 105                 110

Val Trp Gly Gln Gly Thr Thr Val Thr Val Ser Ser Gly Gly Gly Gly
        115                 120                 125

Ser Gly Gly Gly Gly Ser Gly Gly Gly Gly Ser Glu Leu Val Met Thr
    130                 135                 140

Gln Thr Pro Leu Ser Leu Pro Val Ser Leu Gly Asp Gln Ala Ser Ile
145                 150                 155                 160

Ser Cys Arg Ser Ser Gln Ser Leu Val His Ser Asn Gly Asn Thr Tyr
                165                 170                 175

Leu His Trp Tyr Leu Gln Lys Pro Gly Gln Ser Pro Lys Leu Leu Ile
            180                 185                 190

Tyr Lys Val Ser Asn Arg Phe Ser Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Leu Gly Val Tyr Phe Cys Ser Gln Ser Thr His Val Pro Tyr
225                 230                 235                 240

Thr Phe Gly Gly Gly Thr Lys Leu Glu Ile Lys
                245                 250
```

<210> SEQ ID NO 64
<211> LENGTH: 726
<212> TYPE: DNA
<213> ORGANISM: Mus sp.
<220> FEATURE:
<221> NAME/KEY: CDS
<222> LOCATION: (1)..(726)
<223> OTHER INFORMATION:

<400> SEQUENCE: 64

| | | | | | | | | | | | | | | | | |
|---|---|---|---|---|---|---|---|---|---|---|---|---|---|---|---|---|
| gag | gtg | cag | ctg | ctc | gag | cag | tct | gga | gct | gcg | ctg | gta | agg | cct | ggg | 48 |
| Glu | Val | Gln | Leu | Leu | Glu | Gln | Ser | Gly | Ala | Ala | Leu | Val | Arg | Pro | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| act | tca | gtg | aag | ata | tcc | tgc | aag | gct | tct | gga | tac | gcc | ttc | act | aac | 96 |
| Thr | Ser | Val | Lys | Ile | Ser | Cys | Lys | Ala | Ser | Gly | Tyr | Ala | Phe | Thr | Asn | |
| | | | 20 | | | | | 25 | | | | | 30 | | | |

| | | | | | | | | | | | | | | | | |
|---|---|---|---|---|---|---|---|---|---|---|---|---|---|---|---|---|
| tac | tgg | cta | ggt | tgg | gta | aag | cag | agg | cct | gga | cat | gga | ctt | gag | tgg | 144 |
| Tyr | Trp | Leu | Gly | Trp | Val | Lys | Gln | Arg | Pro | Gly | His | Gly | Leu | Glu | Trp | |
| | | 35 | | | | | 40 | | | | | 45 | | | | |

| | | | | | | | | | | | | | | | | |
|---|---|---|---|---|---|---|---|---|---|---|---|---|---|---|---|---|
| att | gga | gat | att | tac | cct | gga | agt | ggt | aat | act | cac | tac | aat | gag | agg | 192 |
| Ile | Gly | Asp | Ile | Tyr | Pro | Gly | Ser | Gly | Asn | Thr | His | Tyr | Asn | Glu | Arg | |
| | 50 | | | | | 55 | | | | | 60 | | | | | |

| | | | | | | | | | | | | | | | | |
|---|---|---|---|---|---|---|---|---|---|---|---|---|---|---|---|---|
| ttc | agg | ggc | aaa | gcc | aca | ctg | act | gca | gac | aaa | tcc | tcg | agc | aca | gcc | 240 |
| Phe | Arg | Gly | Lys | Ala | Thr | Leu | Thr | Ala | Asp | Lys | Ser | Ser | Ser | Thr | Ala | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ttt | atg | cag | ctc | agt | agc | ctg | aca | tct | gag | gac | tct | gct | gtc | tat | ttc | 288 |
| Phe | Met | Gln | Leu | Ser | Ser | Leu | Thr | Ser | Glu | Asp | Ser | Ala | Val | Tyr | Phe | |
| | | | | 85 | | | | | 90 | | | | | 95 | | |

| | | | | | | | | | | | | | | | | |
|---|---|---|---|---|---|---|---|---|---|---|---|---|---|---|---|---|
| tgt | gca | aga | ttg | agg | aac | tgg | gac | gag | cct | atg | gac | tac | tgg | ggc | caa | 336 |
| Cys | Ala | Arg | Leu | Arg | Asn | Trp | Asp | Glu | Pro | Met | Asp | Tyr | Trp | Gly | Gln | |
| | | | 100 | | | | | 105 | | | | | 110 | | | |

| | | | | | | | | | | | | | | | | |
|---|---|---|---|---|---|---|---|---|---|---|---|---|---|---|---|---|
| ggg | acc | acg | gtc | acc | gtc | tcc | tca | ggt | ggt | ggt | ggt | tct | ggc | ggc | ggc | 384 |
| Gly | Thr | Thr | Val | Thr | Val | Ser | Ser | Gly | Gly | Gly | Gly | Ser | Gly | Gly | Gly | |
| | | 115 | | | | | 120 | | | | | 125 | | | | |

| | | | | | | | | | | | | | | | | |
|---|---|---|---|---|---|---|---|---|---|---|---|---|---|---|---|---|
| ggc | tcc | ggt | ggt | ggt | ggt | tct | gag | ctc | cag | atg | acc | cag | tct | cca | tct | 432 |
| Gly | Ser | Gly | Gly | Gly | Gly | Ser | Glu | Leu | Gln | Met | Thr | Gln | Ser | Pro | Ser | |
| | 130 | | | | | 135 | | | | | 140 | | | | | |

| | | | | | | | | | | | | | | | | |
|---|---|---|---|---|---|---|---|---|---|---|---|---|---|---|---|---|
| tat | ctt | gct | gca | tct | cct | gga | gaa | acc | att | act | att | aat | tgc | agg | gca | 480 |
| Tyr | Leu | Ala | Ala | Ser | Pro | Gly | Glu | Thr | Ile | Thr | Ile | Asn | Cys | Arg | Ala | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| agt | aag | agc | att | agc | aaa | tat | tta | gcc | tgg | tat | caa | gag | aaa | cct | ggg | 528 |
| Ser | Lys | Ser | Ile | Ser | Lys | Tyr | Leu | Ala | Trp | Tyr | Gln | Glu | Lys | Pro | Gly | |
| | | | | 165 | | | | | 170 | | | | | 175 | | |

| | | | | | | | | | | | | | | | | |
|---|---|---|---|---|---|---|---|---|---|---|---|---|---|---|---|---|
| aaa | act | aat | aag | ctt | ctt | atc | tac | tct | gga | tcc | act | ttg | caa | tct | gga | 576 |
| Lys | Thr | Asn | Lys | Leu | Leu | Ile | Tyr | Ser | Gly | Ser | Thr | Leu | Gln | Ser | Gly | |
| | | | 180 | | | | | 185 | | | | | 190 | | | |

| | | | | | | | | | | | | | | | | |
|---|---|---|---|---|---|---|---|---|---|---|---|---|---|---|---|---|
| att | cca | tca | agg | ttc | agt | ggc | agt | gga | tct | ggt | aca | gat | ttc | act | ctc | 624 |
| Ile | Pro | Ser | Arg | Phe | Ser | Gly | Ser | Gly | Ser | Gly | Thr | Asp | Phe | Thr | Leu | |
| | | 195 | | | | | 200 | | | | | 205 | | | | |

| | | | | | | | | | | | | | | | | |
|---|---|---|---|---|---|---|---|---|---|---|---|---|---|---|---|---|
| acc | atc | agt | agc | ctg | gag | cct | gaa | gat | ttt | gca | atg | tat | tac | tgt | caa | 672 |
| Thr | Ile | Ser | Ser | Leu | Glu | Pro | Glu | Asp | Phe | Ala | Met | Tyr | Tyr | Cys | Gln | |
| | 210 | | | | | 215 | | | | | 220 | | | | | |

| | | | | | | | | | | | | | | | | |
|---|---|---|---|---|---|---|---|---|---|---|---|---|---|---|---|---|
| cag | cat | aat | gaa | tac | ccg | tac | acg | ttc | gga | ggg | ggg | acc | aag | ctt | gag | 720 |
| Gln | His | Asn | Glu | Tyr | Pro | Tyr | Thr | Phe | Gly | Gly | Gly | Thr | Lys | Leu | Glu | |
| 225 | | | | | 230 | | | | | 235 | | | | | 240 | |

| | | |
|---|---|---|
| atc | aaa | 726 |
| Ile | Lys | |

<210> SEQ ID NO 65
<211> LENGTH: 242
<212> TYPE: PRT
<213> ORGANISM: Mus sp.

<400> SEQUENCE: 65

```
Glu Val Gln Leu Leu Glu Gln Ser Gly Ala Ala Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Ile Gly Asp Ile Tyr Pro Gly Ser Gly Asn Thr His Tyr Asn Glu Arg
    50                  55                  60

Phe Arg Gly Lys Ala Thr Leu Thr Ala Asp Lys Ser Ser Ser Thr Ala
65                  70                  75                  80

Phe Met Gln Leu Ser Ser Leu Thr Ser Glu Asp Ser Ala Val Tyr Phe
                85                  90                  95

Cys Ala Arg Leu Arg Asn Trp Asp Glu Pro Met Asp Tyr Trp Gly Gln
            100                 105                 110

Gly Thr Thr Val Thr Val Ser Ser Gly Gly Gly Ser Gly Gly Gly
            115                 120                 125

Gly Ser Gly Gly Gly Ser Glu Leu Gln Met Thr Gln Ser Pro Ser
130                 135                 140

Tyr Leu Ala Ala Ser Pro Gly Glu Thr Ile Thr Ile Asn Cys Arg Ala
145                 150                 155                 160

Ser Lys Ser Ile Ser Lys Tyr Leu Ala Trp Tyr Gln Glu Lys Pro Gly
                165                 170                 175

Lys Thr Asn Lys Leu Leu Ile Tyr Ser Gly Ser Thr Leu Gln Ser Gly
            180                 185                 190

Ile Pro Ser Arg Phe Ser Gly Ser Gly Ser Gly Thr Asp Phe Thr Leu
        195                 200                 205

Thr Ile Ser Ser Leu Glu Pro Glu Asp Phe Ala Met Tyr Tyr Cys Gln
    210                 215                 220

Gln His Asn Glu Tyr Pro Tyr Thr Phe Gly Gly Gly Thr Lys Leu Glu
225                 230                 235                 240

Ile Lys
```

<210> SEQ ID NO 66
<211> LENGTH: 744
<212> TYPE: DNA
<213> ORGANISM: Mus sp.
<220> FEATURE:
<221> NAME/KEY: CDS
<222> LOCATION: (1)..(744)
<223> OTHER INFORMATION:

<400> SEQUENCE: 66

```
gag gtg cag ctg ctc gag cag tct gga gct gag ctg gta agg cct ggg      48
Glu Val Gln Leu Leu Glu Gln Ser Gly Ala Glu Leu Val Arg Pro Gly
1               5                   10                  15 act tca gtg aag ata tcc tgc aag gct tct gga tac gcc ttc act aac      96
Thr Ser Val Lys Ile Ser Cys Lys Ala Ser Gly Tyr Ala Phe Thr Asn
            20                  25                  30 tac tgg cta ggt tgg gtt aag cag agg cct gga cat gga ctt gaa tgg     144
Tyr Trp Leu Gly Trp Val Lys Gln Arg Pro Gly His Gly Leu Glu Trp
        35                  40                  45 gtt gga gat att ttc cct gga agt ggt aat gct cac tac aat gag aag     192
Val Gly Asp Ile Phe Pro Gly Ser Gly Asn Ala His Tyr Asn Glu Lys
    50                  55                  60
```

-continued

```
ttc aag ggc aaa gcc aca ctg act gca gac aag tcc tcg tac aca gcc    240
Phe Lys Gly Lys Ala Thr Leu Thr Ala Asp Lys Ser Ser Tyr Thr Ala
 65                  70                  75                  80 tat atg cag ctc agt agc ctg aca tct gag gac tct gct gtc tat ttc    288
Tyr Met Gln Leu Ser Ser Leu Thr Ser Glu Asp Ser Ala Val Tyr Phe
                 85                  90                  95 tgt gca aga ttg cgg aac tgg gac gag gct atg gac tac tgg ggc caa    336
Cys Ala Arg Leu Arg Asn Trp Asp Glu Ala Met Asp Tyr Trp Gly Gln
            100                 105                 110 ggg acc acg gtc acc gtc tcc tca ggt ggt ggt ggt tct ggc ggc ggc    384
Gly Thr Thr Val Thr Val Ser Ser Gly Gly Gly Gly Ser Gly Gly Gly
        115                 120                 125 ggc tcc ggt ggt ggt ggt tct gag ctc gtg atg aca cag tct cca tcc    432
Gly Ser Gly Gly Gly Gly Ser Glu Leu Val Met Thr Gln Ser Pro Ser
    130                 135                 140 tcc ctg agt gtg tca gca gga gag aag gtc act atg agc tgc aag tcc    480
Ser Leu Ser Val Ser Ala Gly Glu Lys Val Thr Met Ser Cys Lys Ser
145                 150                 155                 160 agt cag agt ctg tta aac agt gga aat caa aag aac tac ttg gcc tgg    528
Ser Gln Ser Leu Leu Asn Ser Gly Asn Gln Lys Asn Tyr Leu Ala Trp
                165                 170                 175 tac cag cag aaa cca ggg cag cct cct aaa ctg ttg atc tac ggg gca    576
Tyr Gln Gln Lys Pro Gly Gln Pro Pro Lys Leu Leu Ile Tyr Gly Ala
            180                 185                 190 tcc act agg gaa tct ggg gtc cct gat cgc ttc aca ggc agt gga tct    624
Ser Thr Arg Glu Ser Gly Val Pro Asp Arg Phe Thr Gly Ser Gly Ser
        195                 200                 205 gga aca gat ttc act ctc acc atc agc agt gtg cag gct gaa gac ctg    672
Gly Thr Asp Phe Thr Leu Thr Ile Ser Ser Val Gln Ala Glu Asp Leu
    210                 215                 220 gca gtt tat tac tgt cag aat gat tat agt tat ccg tac acg ttc gga    720
Ala Val Tyr Tyr Cys Gln Asn Asp Tyr Ser Tyr Pro Tyr Thr Phe Gly
225                 230                 235                 240 ggg ggg acc aag ctt gag atc aaa                                    744
Gly Gly Thr Lys Leu Glu Ile Lys
                245
```

<210> SEQ ID NO 67
<211> LENGTH: 248
<212> TYPE: PRT
<213> ORGANISM: Mus sp.

<400> SEQUENCE: 67

```
Glu Val Gln Leu Leu Glu Gln Ser Gly Ala Glu Leu Val Arg Pro Gly
 1               5                  10                  15

Thr Ser Val Lys Ile Ser Cys Lys Ala Ser Gly Tyr Ala Phe Thr Asn
             20                  25                  30

Tyr Trp Leu Gly Trp Val Lys Gln Arg Pro Gly His Gly Leu Glu Trp
         35                  40                  45

Val Gly Asp Ile Phe Pro Gly Ser Gly Asn Ala His Tyr Asn Glu Lys
     50                  55                  60

Phe Lys Gly Lys Ala Thr Leu Thr Ala Asp Lys Ser Ser Tyr Thr Ala
 65                  70                  75                  80

Tyr Met Gln Leu Ser Ser Leu Thr Ser Glu Asp Ser Ala Val Tyr Phe
                 85                  90                  95

Cys Ala Arg Leu Arg Asn Trp Asp Glu Ala Met Asp Tyr Trp Gly Gln
            100                 105                 110

Gly Thr Thr Val Thr Val Ser Ser Gly Gly Gly Gly Ser Gly Gly Gly
        115                 120                 125
```

-continued

```
Gly Ser Gly Gly Gly Ser Glu Leu Val Met Thr Gln Ser Pro Ser
        130                 135                 140

Ser Leu Ser Val Ser Ala Gly Glu Lys Val Thr Met Ser Cys Lys Ser
145                 150                 155                 160

Ser Gln Ser Leu Leu Asn Ser Gly Asn Gln Lys Asn Tyr Leu Ala Trp
                165                 170                 175

Tyr Gln Gln Lys Pro Gly Gln Pro Pro Lys Leu Leu Ile Tyr Gly Ala
            180                 185                 190

Ser Thr Arg Glu Ser Gly Val Pro Asp Arg Phe Thr Gly Ser Gly Ser
        195                 200                 205

Gly Thr Asp Phe Thr Leu Thr Ile Ser Ser Val Gln Ala Glu Asp Leu
    210                 215                 220

Ala Val Tyr Tyr Cys Gln Asn Asp Tyr Ser Tyr Pro Tyr Thr Phe Gly
225                 230                 235                 240

Gly Gly Thr Lys Leu Glu Ile Lys
                245
```

<210> SEQ ID NO 68
<211> LENGTH: 726
<212> TYPE: DNA
<213> ORGANISM: Mus sp.
<220> FEATURE:
<221> NAME/KEY: CDS
<222> LOCATION: (1)..(726)
<223> OTHER INFORMATION:

<400> SEQUENCE: 68

```
gag gtg cag ctg ctc gag cag tct gga gct gag ctg gtg agg cct ggg    48
Glu Val Gln Leu Leu Glu Gln Ser Gly Ala Glu Leu Val Arg Pro Gly
1               5                   10                  15 gct tca gtg aag ata tcc tgc aag gct tct gga tac gcc ttc aat aac    96
Ala Ser Val Lys Ile Ser Cys Lys Ala Ser Gly Tyr Ala Phe Asn Asn
                20                  25                  30 tac tgg cta ggt tgg gta aag cag agg cct gga cat gga ctt gag tgg   144
Tyr Trp Leu Gly Trp Val Lys Gln Arg Pro Gly His Gly Leu Glu Trp
            35                  40                  45 att gga gac att tac cct gga agt gga aat act cac tac aat gag agg   192
Ile Gly Asp Ile Tyr Pro Gly Ser Gly Asn Thr His Tyr Asn Glu Arg
        50                  55                  60 ttc agg ggc aaa gcc aca ctg act gca gac aaa tcc tcg agc aca gcc   240
Phe Arg Gly Lys Ala Thr Leu Thr Ala Asp Lys Ser Ser Ser Thr Ala
65                  70                  75                  80 ttt atg cag tta agt agc ctg aca tct gag gac tct gct gtc tat ttc   288
Phe Met Gln Leu Ser Ser Leu Thr Ser Glu Asp Ser Ala Val Tyr Phe
                85                  90                  95 tgt gca aga ttg agg aac tgg gac gag gct atg gac tac tgg ggc caa   336
Cys Ala Arg Leu Arg Asn Trp Asp Glu Ala Met Asp Tyr Trp Gly Gln
            100                 105                 110 ggg acc acg gtc acc gtc tcc tca ggt ggt ggt ggt tct ggc ggc ggc   384
Gly Thr Thr Val Thr Val Ser Ser Gly Gly Gly Gly Ser Gly Gly Gly
        115                 120                 125 ggc tcc ggt ggt ggt ggt tct gag ctc gtc atg acc cag tct cca tct   432
Gly Ser Gly Gly Gly Gly Ser Glu Leu Val Met Thr Gln Ser Pro Ser
130                 135                 140 tat ctt gct gca tct cct gga gaa acc att act att aat tgc agg gca   480
Tyr Leu Ala Ala Ser Pro Gly Glu Thr Ile Thr Ile Asn Cys Arg Ala
145                 150                 155                 160 agt aag agc att agc aaa tat tta gcc tgg tat caa gag aaa cct ggg   528
Ser Lys Ser Ile Ser Lys Tyr Leu Ala Trp Tyr Gln Glu Lys Pro Gly
                165                 170                 175
```

-continued

```
aaa act aat aag ctt ctt atc tac tct gga tcc act ttg caa tct gga      576
Lys Thr Asn Lys Leu Leu Ile Tyr Ser Gly Ser Thr Leu Gln Ser Gly
            180                 185                 190 att cca tca agg ttc agt ggc agt gga tct ggt aca gat ttc act ctc      624
Ile Pro Ser Arg Phe Ser Gly Ser Gly Ser Gly Thr Asp Phe Thr Leu
        195                 200                 205 acc atc agt agc ctg gag cct gaa gat ttt gca atg tat tac tgt caa      672
Thr Ile Ser Ser Leu Glu Pro Glu Asp Phe Ala Met Tyr Tyr Cys Gln
    210                 215                 220 cag cat aat gaa tac ccg tac acg ttc gga ggg ggg acc aag ctt gag      720
Gln His Asn Glu Tyr Pro Tyr Thr Phe Gly Gly Gly Thr Lys Leu Glu
225                 230                 235                 240 atc aaa                                                              726
Ile Lys
```

<210> SEQ ID NO 69
<211> LENGTH: 242
<212> TYPE: PRT
<213> ORGANISM: Mus sp.

<400> SEQUENCE: 69

```
Glu Val Gln Leu Leu Glu Gln Ser Gly Ala Glu Leu Val Arg Pro Gly
1               5                   10                  15

Ala Ser Val Lys Ile Ser Cys Lys Ala Ser Gly Tyr Ala Phe Asn Asn
            20                  25                  30

Tyr Trp Leu Gly Trp Val Lys Gln Arg Pro Gly His Gly Leu Glu Trp
        35                  40                  45

Ile Gly Asp Ile Tyr Pro Gly Ser Gly Asn Thr His Tyr Asn Glu Arg
    50                  55                  60

Phe Arg Gly Lys Ala Thr Leu Thr Ala Asp Lys Ser Ser Ser Thr Ala
65                  70                  75                  80

Phe Met Gln Leu Ser Ser Leu Thr Ser Glu Asp Ser Ala Val Tyr Phe
                85                  90                  95

Cys Ala Arg Leu Arg Asn Trp Asp Glu Ala Met Asp Tyr Trp Gly Gln
            100                 105                 110

Gly Thr Thr Val Thr Val Ser Ser Gly Gly Gly Ser Gly Gly Gly
        115                 120                 125

Gly Ser Gly Gly Gly Ser Glu Leu Val Met Thr Gln Ser Pro Ser
    130                 135                 140

Tyr Leu Ala Ala Ser Pro Gly Glu Thr Ile Thr Ile Asn Cys Arg Ala
145                 150                 155                 160

Ser Lys Ser Ile Ser Lys Tyr Leu Ala Trp Tyr Gln Glu Lys Pro Gly
                165                 170                 175

Lys Thr Asn Lys Leu Leu Ile Tyr Ser Gly Ser Thr Leu Gln Ser Gly
            180                 185                 190

Ile Pro Ser Arg Phe Ser Gly Ser Gly Ser Gly Thr Asp Phe Thr Leu
        195                 200                 205

Thr Ile Ser Ser Leu Glu Pro Glu Asp Phe Ala Met Tyr Tyr Cys Gln
    210                 215                 220

Gln His Asn Glu Tyr Pro Tyr Thr Phe Gly Gly Gly Thr Lys Leu Glu
225                 230                 235                 240

Ile Lys
```

<210> SEQ ID NO 70
<211> LENGTH: 753
<212> TYPE: DNA
<213> ORGANISM: Mus sp.

```
<220> FEATURE:
<221> NAME/KEY: CDS
<222> LOCATION: (1)..(753)
<223> OTHER INFORMATION:

<400> SEQUENCE: 70 gag gtg cag ctg ctc gag cag tct gga gct gag ctg gcg agg cct ggg      48
Glu Val Gln Leu Leu Glu Gln Ser Gly Ala Glu Leu Ala Arg Pro Gly
1               5                   10                  15 gct tca gtg aag ctg tcc tgc aag gct tct ggc tac acc ttc aca aac      96
Ala Ser Val Lys Leu Ser Cys Lys Ala Ser Gly Tyr Thr Phe Thr Asn
            20                  25                  30 tat ggt tta agc tgg gtg aag cag agg cct gga cag gtc ctt gag tgg     144
Tyr Gly Leu Ser Trp Val Lys Gln Arg Pro Gly Gln Val Leu Glu Trp
        35                  40                  45 att gga gag gtt tat cct aga att ggt aat gct tac tac aat gag aag     192
Ile Gly Glu Val Tyr Pro Arg Ile Gly Asn Ala Tyr Tyr Asn Glu Lys
    50                  55                  60 ttc aag ggc aag gcc aca ctg act gca gac aaa tcc tcc agc aca gcg     240
Phe Lys Gly Lys Ala Thr Leu Thr Ala Asp Lys Ser Ser Ser Thr Ala
65                  70                  75                  80 tcc atg gag ctc cgc agc ctg acc tct gag gac tct gcg gtc tat ttc     288
Ser Met Glu Leu Arg Ser Leu Thr Ser Glu Asp Ser Ala Val Tyr Phe
                85                  90                  95 tgt gca aga cgg gga tcc tac gat act aac tac gac tgg tac ttc gat     336
Cys Ala Arg Arg Gly Ser Tyr Asp Thr Asn Tyr Asp Trp Tyr Phe Asp
            100                 105                 110 gtc tgg ggc caa ggg acc acg gtc acc gtc tcc tca ggt ggt ggt ggt     384
Val Trp Gly Gln Gly Thr Thr Val Thr Val Ser Ser Gly Gly Gly Gly
        115                 120                 125 tct ggc ggc ggc ggc tcc ggt ggt ggt ggt tct gag ctc gtg atg acc     432
Ser Gly Gly Gly Gly Ser Gly Gly Gly Gly Ser Glu Leu Val Met Thr
    130                 135                 140 cag act cca ctc tcc ctg cct gtc agt ctt gga gat caa gcc tcc atc     480
Gln Thr Pro Leu Ser Leu Pro Val Ser Leu Gly Asp Gln Ala Ser Ile
145                 150                 155                 160 tct tgc aga tct agt cag agc ctt gta cac agt aat gga aac acc tat     528
Ser Cys Arg Ser Ser Gln Ser Leu Val His Ser Asn Gly Asn Thr Tyr
                165                 170                 175 tta cat tgg tac ctg cag aag cca ggc cag tct cca aag ctc ctg atc     576
Leu His Trp Tyr Leu Gln Lys Pro Gly Gln Ser Pro Lys Leu Leu Ile
            180                 185                 190 tac aaa gtt tcc aac cga ttt tct ggg gtc cca gac agg ttc agt ggc     624
Tyr Lys Val Ser Asn Arg Phe Ser Gly Val Pro Asp Arg Phe Ser Gly
        195                 200                 205 agt gga tca ggg aca gat ttc aca ctc aag atc agc aga gtg gag gct     672
Ser Gly Ser Gly Thr Asp Phe Thr Leu Lys Ile Ser Arg Val Glu Ala
    210                 215                 220 gag gat ctg gga gtt tat ttc tgc tct caa agt aca cat gtt ccg tac     720
Glu Asp Leu Gly Val Tyr Phe Cys Ser Gln Ser Thr His Val Pro Tyr
225                 230                 235                 240 acg ttc gga ggg ggg acc aag ctt gag atc aaa                         753
Thr Phe Gly Gly Gly Thr Lys Leu Glu Ile Lys
                245                 250

<210> SEQ ID NO 71
<211> LENGTH: 251
<212> TYPE: PRT
<213> ORGANISM: Mus sp.
```

<400> SEQUENCE: 71

```
Glu Val Gln Leu Leu Glu Gln Ser Gly Ala Glu Leu Ala Arg Pro Gly
1               5                   10                  15

Ala Ser Val Lys Leu Ser Cys Lys Ala Ser Gly Tyr Thr Phe Thr Asn
            20                  25                  30

Tyr Gly Leu Ser Trp Val Lys Gln Arg Pro Gly Gln Val Leu Glu Trp
        35                  40                  45

Ile Gly Glu Val Tyr Pro Arg Ile Gly Asn Ala Tyr Asn Glu Lys
50                  55                  60

Phe Lys Gly Lys Ala Thr Leu Thr Ala Asp Lys Ser Ser Ser Thr Ala
65                  70                  75                  80

Ser Met Glu Leu Arg Ser Leu Thr Ser Glu Asp Ser Ala Val Tyr Phe
                85                  90                  95

Cys Ala Arg Arg Gly Ser Tyr Asp Thr Asn Tyr Asp Trp Tyr Phe Asp
            100                 105                 110

Val Trp Gly Gln Gly Thr Thr Val Thr Val Ser Ser Gly Gly Gly Gly
        115                 120                 125

Ser Gly Gly Gly Gly Ser Gly Gly Gly Ser Glu Leu Val Met Thr
130                 135                 140

Gln Thr Pro Leu Ser Leu Pro Val Ser Leu Gly Asp Gln Ala Ser Ile
145                 150                 155                 160

Ser Cys Arg Ser Ser Gln Ser Leu Val His Ser Asn Gly Asn Thr Tyr
                165                 170                 175

Leu His Trp Tyr Leu Gln Lys Pro Gly Gln Ser Pro Lys Leu Leu Ile
            180                 185                 190

Tyr Lys Val Ser Asn Arg Phe Ser Gly Val Pro Asp Arg Phe Ser Gly
        195                 200                 205

Ser Gly Ser Gly Thr Asp Phe Thr Leu Lys Ile Ser Arg Val Glu Ala
210                 215                 220

Glu Asp Leu Gly Val Tyr Phe Cys Ser Gln Ser Thr His Val Pro Tyr
225                 230                 235                 240

Thr Phe Gly Gly Gly Thr Lys Leu Glu Ile Lys
                245                 250
```

<210> SEQ ID NO 72
<211> LENGTH: 717
<212> TYPE: DNA
<213> ORGANISM: Mus sp.
<220> FEATURE:
<221> NAME/KEY: CDS
<222> LOCATION: (1)..(717)
<223> OTHER INFORMATION:

<400> SEQUENCE: 72

```
gag gtg cag ctg ctc gag tct gga ggt ggc ctg gtg cag cct gga gga    48
Glu Val Gln Leu Leu Glu Ser Gly Gly Gly Leu Val Gln Pro Gly Gly
1               5                   10                  15 tcc ctg aaa ctc tcc tgt gca gcc tca gga ttc gat ttt agt aga tac    96
Ser Leu Lys Leu Ser Cys Ala Ala Ser Gly Phe Asp Phe Ser Arg Tyr
            20                  25                  30 tgg atg agt tgg gtc cgg cag gct cca ggg aaa ggg cta gaa tgg att   144
Trp Met Ser Trp Val Arg Gln Ala Pro Gly Lys Gly Leu Glu Trp Ile
        35                  40                  45 gga gaa att aat cca gat agc agt acg ata aac tat acg cca tct ctg   192
Gly Glu Ile Asn Pro Asp Ser Ser Thr Ile Asn Tyr Thr Pro Ser Leu
50                  55                  60
```

```
aag gat aaa ttc atc atc tcc aga gac aac gcc aaa aat acg ctg tac        240
Lys Asp Lys Phe Ile Ile Ser Arg Asp Asn Ala Lys Asn Thr Leu Tyr
 65                  70                  75                  80 ctg caa atg ggc aaa gtg aga tct gag gac aca gcc ctt tat tac tgt        288
Leu Gln Met Gly Lys Val Arg Ser Glu Asp Thr Ala Leu Tyr Tyr Cys
                 85                  90                  95 gca aga gga gcc ttc ctt ttt gac tac tgg ggc caa ggg acc acg gtc        336
Ala Arg Gly Ala Phe Leu Phe Asp Tyr Trp Gly Gln Gly Thr Thr Val
            100                 105                 110 acc gtc tcc tca ggt ggt ggt ggt tct ggc ggc ggc tcc ggt ggt            384
Thr Val Ser Ser Gly Gly Gly Gly Ser Gly Gly Gly Ser Gly Gly
        115                 120                 125 ggt ggt tct gag ctc gtg ctc acc cag tct cca acc acc atg gct gca        432
Gly Gly Ser Glu Leu Val Leu Thr Gln Ser Pro Thr Thr Met Ala Ala
130                 135                 140 tct ccc ggg gag aag atc act atc acc tgc agt gcc agc tca agt ata        480
Ser Pro Gly Glu Lys Ile Thr Ile Thr Cys Ser Ala Ser Ser Ser Ile
145                 150                 155                 160 agt tcc aat tac ttg cat tgg tat cag cag aag cca gga ttc tcc cct        528
Ser Ser Asn Tyr Leu His Trp Tyr Gln Gln Lys Pro Gly Phe Ser Pro
                165                 170                 175 aaa ctc ttg att tat agg aca tcc aat ctg gct tct gga gtc cca gct        576
Lys Leu Leu Ile Tyr Arg Thr Ser Asn Leu Ala Ser Gly Val Pro Ala
            180                 185                 190 cgc ttc agt ggc agt ggg tct ggg acc tct tac tct ctc aca att ggc        624
Arg Phe Ser Gly Ser Gly Ser Gly Thr Ser Tyr Ser Leu Thr Ile Gly
        195                 200                 205 acc atg gag gct gaa gat gtt gcc act tac tac tgc cag cag ggt agt        672
Thr Met Glu Ala Glu Asp Val Ala Thr Tyr Tyr Cys Gln Gln Gly Ser
210                 215                 220 agt ata cca ctc acg ttc ggt gct ggg acc aag ctt gag atc aaa            717
Ser Ile Pro Leu Thr Phe Gly Ala Gly Thr Lys Leu Glu Ile Lys
225                 230                 235
```

<210> SEQ ID NO 73
<211> LENGTH: 239
<212> TYPE: PRT
<213> ORGANISM: Mus sp.

<400> SEQUENCE: 73

```
Glu Val Gln Leu Leu Glu Ser Gly Gly Gly Leu Val Gln Pro Gly Gly
 1               5                  10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
 65                  70                  75                  80

Leu Gln Met Gly Lys Val Arg Ser Glu Asp Thr Ala Leu Tyr Tyr Cys
                 85                  90                  95

Ala Arg Gly Ala Phe Leu Phe Asp Tyr Trp Gly Gln Gly Thr Thr Val
            100                 105                 110

Thr Val Ser Ser Gly Gly Gly Gly Ser Gly Gly Gly Ser Gly Gly
        115                 120                 125

Gly Gly Ser Glu Leu Val Leu Thr Gln Ser Pro Thr Thr Met Ala Ala
130                 135                 140
```

```
Ser Pro Gly Glu Lys Ile Thr Ile Thr Cys Ser Ala Ser Ser Ser Ile
145                 150                 155                 160

Ser Ser Asn Tyr Leu His Trp Tyr Gln Gln Lys Pro Gly Phe Ser Pro
            165                 170                 175

Lys Leu Leu Ile Tyr Arg Thr Ser Asn Leu Ala Ser Gly Val Pro Ala
        180                 185                 190

Arg Phe Ser Gly Ser Gly Ser Gly Thr Ser Tyr Ser Leu Thr Ile Gly
            195                 200                 205

Thr Met Glu Ala Glu Asp Val Ala Thr Tyr Tyr Cys Gln Gln Gly Ser
        210                 215                 220

Ser Ile Pro Leu Thr Phe Gly Ala Gly Thr Lys Leu Glu Ile Lys
225                 230                 235

<210> SEQ ID NO 74
<211> LENGTH: 744
<212> TYPE: DNA
<213> ORGANISM: Mus sp.
<220> FEATURE:
<221> NAME/KEY: CDS
<222> LOCATION: (1)..(744)
<223> OTHER INFORMATION:

<400> SEQUENCE: 74 gag gtg cag ctg ctc gag cag tct gga gct gag ctg gta agg cct ggg     48
Glu Val Gln Leu Leu Glu Gln Ser Gly Ala Glu Leu Val Arg Pro Gly
1               5                   10                  15 act tca gtg aag ata tcc tgc aag gct tct gga tac gcc ttc act aac     96
Thr Ser Val Lys Ile Ser Cys Lys Ala Ser Gly Tyr Ala Phe Thr Asn
            20                  25                  30 tac tgg cta ggt tgg gta aag cag agg cct gga cat gga ctt gag tgg    144
Tyr Trp Leu Gly Trp Val Lys Gln Arg Pro Gly His Gly Leu Glu Trp
        35                  40                  45 att gga gat att ttc cct gga agt ggt aat atc cac tac aat gag aag    192
Ile Gly Asp Ile Phe Pro Gly Ser Gly Asn Ile His Tyr Asn Glu Lys
    50                  55                  60 ttc aag ggc aaa gcc aca ctg act gca gac aaa tct tcg agc aca gcc    240
Phe Lys Gly Lys Ala Thr Leu Thr Ala Asp Lys Ser Ser Ser Thr Ala
65                  70                  75                  80 tat atg cag ctc agt agc ctg aca ttt gag gac tct gct gtc tat ttc    288
Tyr Met Gln Leu Ser Ser Leu Thr Phe Glu Asp Ser Ala Val Tyr Phe
                85                  90                  95 tgt gca aga ctg agg aac tgg gac gag cct atg gac tac tgg ggc caa    336
Cys Ala Arg Leu Arg Asn Trp Asp Glu Pro Met Asp Tyr Trp Gly Gln
            100                 105                 110 ggg acc acg gtc acc gtc tcc tca ggt ggt ggt ggt tct ggc ggc ggc    384
Gly Thr Thr Val Thr Val Ser Ser Gly Gly Gly Gly Ser Gly Gly Gly
        115                 120                 125 ggc tcc ggt ggt ggt ggt tct gag ctc gtg atg aca cag tct cca tcc    432
Gly Ser Gly Gly Gly Gly Ser Glu Leu Val Met Thr Gln Ser Pro Ser
    130                 135                 140 tcc ctg act gtg aca gca gga gag aag gtc act atg agc tgc aag tcc    480
Ser Leu Thr Val Thr Ala Gly Glu Lys Val Thr Met Ser Cys Lys Ser
145                 150                 155                 160 agt cag agt ctg tta aac agt gga aat caa aag aac tac ttg acc tgg    528
Ser Gln Ser Leu Leu Asn Ser Gly Asn Gln Lys Asn Tyr Leu Thr Trp
                165                 170                 175 tac cag cag aaa cca ggg cag cct cct aaa ctg ttg atc tac tgg gca    576
Tyr Gln Gln Lys Pro Gly Gln Pro Pro Lys Leu Leu Ile Tyr Trp Ala
            180                 185                 190
```

| | | | | | | | | | | | | | | | | |
|---|---|---|---|---|---|---|---|---|---|---|---|---|---|---|---|---|
| tcc | act | agg | gaa | tct | ggg | gtc | cct | gat | cgc | ttc | aca | ggc | agt | gga | tct | 624 |
| Ser | Thr | Arg | Glu | Ser | Gly | Val | Pro | Asp | Arg | Phe | Thr | Gly | Ser | Gly | Ser | |
| | 195 | | | | 200 | | | | | 205 | | | | | | |
| gga | aca | gat | ttc | act | ctc | acc | atc | agc | agt | gtg | cag | gct | gaa | gac | ctg | 672 |
| Gly | Thr | Asp | Phe | Thr | Leu | Thr | Ile | Ser | Ser | Val | Gln | Ala | Glu | Asp | Leu | |
| 210 | | | | | 215 | | | | 220 | | | | | | | |
| gca | gtt | tat | tac | tgt | cag | aat | gat | tat | agt | tat | ccg | ctc | acg | ttc | ggt | 720 |
| Ala | Val | Tyr | Tyr | Cys | Gln | Asn | Asp | Tyr | Ser | Tyr | Pro | Leu | Thr | Phe | Gly | |
| 225 | | | | | 230 | | | | | 235 | | | | | 240 | |
| gct | ggg | acc | aag | ctt | gag | atc | aaa | | | | | | | | | 744 |
| Ala | Gly | Thr | Lys | Leu | Glu | Ile | Lys | | | | | | | | | |
| | | | | 245 | | | | | | | | | | | | |

<210> SEQ ID NO 75
<211> LENGTH: 248
<212> TYPE: PRT
<213> ORGANISM: Mus sp.

<400> SEQUENCE: 75

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Ile Gly Asp Ile Phe Pro Gly Ser Gly Asn Ile His Tyr Asn Glu Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Glu Pro Met Asp Tyr Trp Gly Gln
            100                 105                 110

Gly Thr Thr Val Thr Val Ser Ser Gly Gly Gly Ser Gly Gly Gly
        115                 120                 125

Gly Ser Gly Gly Gly Ser Glu Leu Val Met Thr Gln Ser Pro Ser
    130                 135                 140

Ser Leu Thr Val Thr Ala Gly Glu Lys Val Thr Met Ser Cys Lys Ser
145                 150                 155                 160

Ser Gln Ser Leu Leu Asn Ser Gly Asn Gln Lys Asn Tyr Leu Thr Trp
                165                 170                 175

Tyr Gln Gln Lys Pro Gly Gln Pro Pro Lys Leu Leu Ile Tyr Trp Ala
            180                 185                 190

Ser Thr Arg Glu Ser Gly Val Pro Asp Arg Phe Thr Gly Ser Gly Ser
        195                 200                 205

Gly Thr Asp Phe Thr Leu Thr Ile Ser Ser Val Gln Ala Glu Asp Leu
    210                 215                 220

Ala Val Tyr Tyr Cys Gln Asn Asp Tyr Ser Tyr Pro Leu Thr Phe Gly
225                 230                 235                 240

Ala Gly Thr Lys Leu Glu Ile Lys
                245

<210> SEQ ID NO 76
<211> LENGTH: 744
<212> TYPE: DNA
<213> ORGANISM: Mus sp.

```
<220> FEATURE:
<221> NAME/KEY: CDS
<222> LOCATION: (1)..(744)
<223> OTHER INFORMATION:

<400> SEQUENCE: 76 gag gtg cag ctg ctc gag cag tct gga gct gag ctg gta agg cct ggg      48
Glu Val Gln Leu Leu Glu Gln Ser Gly Ala Glu Leu Val Arg Pro Gly
1               5                   10                  15 act tca gtg aag ata tcc tgc aag gct tct gga tac gcc ttc act aac      96
Thr Ser Val Lys Ile Ser Cys Lys Ala Ser Gly Tyr Ala Phe Thr Asn
            20                  25                  30 tac tgg cta ggt tgg gtt aag cag agg cct gga cat gga ctt gaa tgg     144
Tyr Trp Leu Gly Trp Val Lys Gln Arg Pro Gly His Gly Leu Glu Trp
        35                  40                  45 gtt gga gat att ttc cct gga agt ggt aat gct cac tac aat gag aag     192
Val Gly Asp Ile Phe Pro Gly Ser Gly Asn Ala His Tyr Asn Glu Lys
    50                  55                  60 ttc aag ggc aaa gcc aca ctg act gca gac aag tcc tcg tac aca gcc     240
Phe Lys Gly Lys Ala Thr Leu Thr Ala Asp Lys Ser Ser Tyr Thr Ala
65                  70                  75                  80 tat atg cag ctc agt agc ctg aca tct gag gac tct gct gtc tat ttc     288
Tyr Met Gln Leu Ser Ser Leu Thr Ser Glu Asp Ser Ala Val Tyr Phe
                85                  90                  95 tgt gca aga ttg cgg aac tgg gac gag gct atg gac tac tgg ggc caa     336
Cys Ala Arg Leu Arg Asn Trp Asp Glu Ala Met Asp Tyr Trp Gly Gln
            100                 105                 110 ggg acc acg gtc acc gtc tcc tca ggt ggt ggt ggt tct ggc ggc ggc     384
Gly Thr Thr Val Thr Val Ser Ser Gly Gly Gly Gly Ser Gly Gly Gly
        115                 120                 125 ggc tcc ggt ggt ggt ggt tct gag ctc gtg atg aca cag tct cca tcc     432
Gly Ser Gly Gly Gly Gly Ser Glu Leu Val Met Thr Gln Ser Pro Ser
    130                 135                 140 tcc ctg gct atg tca gta gga cag aag gtc act atg agc tgc aag tcc     480
Ser Leu Ala Met Ser Val Gly Gln Lys Val Thr Met Ser Cys Lys Ser
145                 150                 155                 160 agt cag agc ctt tta aat agt agc aat caa aag aac tat ttg gcc tgg     528
Ser Gln Ser Leu Leu Asn Ser Ser Asn Gln Lys Asn Tyr Leu Ala Trp
                165                 170                 175 tac cag cag aaa caa ggg cag cct cct aaa ctg ctt atc tat ggg gca     576
Tyr Gln Gln Lys Gln Gly Gln Pro Pro Lys Leu Leu Ile Tyr Gly Ala
            180                 185                 190 tcc att aga gaa tct tgg gtc cct gat cga ttc aca gga agt gga tct     624
Ser Ile Arg Glu Ser Trp Val Pro Asp Arg Phe Thr Gly Ser Gly Ser
        195                 200                 205 ggg aca gac ttc act ctc acc atc agc agt gtg aag gct gaa gac ctg     672
Gly Thr Asp Phe Thr Leu Thr Ile Ser Ser Val Lys Ala Glu Asp Leu
    210                 215                 220 gca gtt tat tac tgt cag caa tat tat agc tat ccg tac acg ttc gga     720
Ala Val Tyr Tyr Cys Gln Gln Tyr Tyr Ser Tyr Pro Tyr Thr Phe Gly
225                 230                 235                 240 ggg ggg acc aag ctt gag atc aaa                                     744
Gly Gly Thr Lys Leu Glu Ile Lys
                245

<210> SEQ ID NO 77
<211> LENGTH: 248
<212> TYPE: PRT
<213> ORGANISM: Mus sp.
```

-continued

```
<400> SEQUENCE: 77

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Val Gly Asp Ile Phe Pro Gly Ser Gly Asn Ala His Tyr Asn Glu Lys
    50                  55                  60

Phe Lys Gly Lys Ala Thr Leu Thr Ala Asp Lys Ser Ser Tyr Thr Ala
65                  70                  75                  80

Tyr Met Gln Leu Ser Ser Leu Thr Ser Glu Asp Ser Ala Val Tyr Phe
            85                  90                  95

Cys Ala Arg Leu Arg Asn Trp Asp Glu Ala Met Asp Tyr Trp Gly Gln
            100                 105                 110

Gly Thr Thr Val Thr Val Ser Ser Gly Gly Gly Ser Gly Gly Gly
        115                 120                 125

Gly Ser Gly Gly Gly Gly Ser Glu Leu Val Met Thr Gln Ser Pro Ser
    130                 135                 140

Ser Leu Ala Met Ser Val Gly Gln Lys Val Thr Met Ser Cys Lys Ser
145                 150                 155                 160

Ser Gln Ser Leu Leu Asn Ser Ser Asn Gln Lys Asn Tyr Leu Ala Trp
            165                 170                 175

Tyr Gln Gln Lys Gln Gly Gln Pro Pro Lys Leu Leu Ile Tyr Gly Ala
            180                 185                 190

Ser Ile Arg Glu Ser Trp Val Pro Asp Arg Phe Thr Gly Ser Gly Ser
            195                 200                 205

Gly Thr Asp Phe Thr Leu Thr Ile Ser Ser Val Lys Ala Glu Asp Leu
    210                 215                 220

Ala Val Tyr Tyr Cys Gln Gln Tyr Tyr Ser Tyr Pro Tyr Thr Phe Gly
225                 230                 235                 240

Gly Gly Thr Lys Leu Glu Ile Lys
            245
```

METHOD OF IDENTIFYING BINDING SITE DOMAINS THAT RETAIN THE CAPACITY OF BINDING TO AN EPITOPE

This application is the national phase under 35 U.S.C. § 371 of PCT International Application No. PCT/EP98/07313 which has an International filing date of Nov. 16, 1998, which designated the United States of America.

The present invention relates to a method of identifying domains having binding affinity for a preselected epitope. The domains comprise preferably immunoglobulin $V_H$ and $V_L$ domains that retain the capacity of binding to an epitope when positioned C-terminal of at least one further domain in a recombinant bi- or multivalent polypeptide. The present invention further relates to a kit comprising components such as panels of recombinant vectors or bacterial libraries transfected with a panel of recombinant vectors which is useful in carrying out the method of the invention. Furthermore, the present invention relates to polypeptides obtainable by the afore-described method and their use in pharmaceutical and diagnostic compositions.

Multivalent receptors such as recombinant bifunctional antibody constructs play an increasingly important therapeutic and scientific role in particular in the medical field, for example, in the development of new treatment approaches for cancer and autoimmune diseases or as interesting tools for the analysis and modulation of cellular signal transduction pathways, pioneer work has been done using such receptors.

Thus, by cross-linking of the CD3-activation antigen on T cells with a tumor associated antigen on tumor cells, bispecific single-chain antibodies can bring both cells together so that the tumor cell is efficiently lysed during the cell-cell contact (Mack, Proc. Natl. Acad. Sci. U.S.A. 92 (1995) 7021-7025). Comparable approaches have been or are being developed for other target cells (e.g. virus-infected cells) and for the recruitment of other effector cell populations (e.g. NK-cells and mononuclear phagocytes). Using bifunctional fusion proteins that carry an antibody fragment as targeting mechanism, a large number of different receptors and ligands can be specifically bound to defined surface molecules on selected cell populations. It is particularly interesting that surface molecules on the same cell can be cross-linked by bi-specific antibodies in order to modulate cellular function or the state of activation or differentiation of such cells. A possible application of this type of approach may be the induction of anergy in auto-aggressive B- or T-lymphocytes that play a pathogenetic role in many autoimmune diseases. Regarding the broad scientific and therapeutic relevance, efficient and reproducible methods for producing recombinant polypeptides comprising functional antigen binding sites are of particular importance; such methods yield, for example, functionally active bispecific antibody constructs by expression in bacteria and in mammalian cells. Said recombinant bifunctional single-chain proteins usually are built up by different scFv-antibody fragments, each of which consists of one immunoglobulin variable heavy ($V_H$) and one variable light ($V_L$)-antigen binding domain. Alternatively, they may comprise such an antibody fragment and one non-immunoglobulin part. All functional domains are located on a single polypeptide chain and joined together by flexible Glycin-Serin- or other appropriate peptide linkers. The bifunctional polypeptide chain can be produced as functional protein by transfecting mammalian or less preferentially other host cells with the corresponding DNA-sequence, that additionally may encode an optional protein-tag, preferentially a poly-histidine-tag, enabling easy purification of the recombinant protein for example by using a nickel-chelate-column. The production of multivalent and preferably bifunctional constructs according to this single-chain approach has important advantages compared to conventional methods using in vitro- or in vivo-heterodi- or multimerization of independently expressed functional domains, a procedure that can be very laborious and frequently associated with low yields. The appearance of contaminating homodimers is excluded by the single-chain approach, thus resulting in protein preparations of high purity and yield since all the recombinant protein produced consists to 100% of the desired bifunctional construct. As has been demonstrated by way of example with a bispecific single-chain antibody functionally expressed in CHO-cells, scFv-antibody fragments can in principle bind to their antigen either as the N-terminal or the C-terminal part of a bifunctional single-chain construct, (Mack, Proc. Natl. Acad. Sci. U.S.A. 92(1995) 7021-7025).

However, many functional domains of multivalent polypeptides such as antibody fragments lose their binding activity when located C-terminal of a further three-dimensional proteinaceous structure within a fusion protein. For example, scFv-fragments derived from randomly selected antibodies produced by hybridoma cell lines or selected in vitro from combinatorial antibody libraries frequently lose their antigen binding activity when located at the C-terminal position within recombinant bifunctional single-chain proteins, although the same $V_H/V_L$-pairs bind to the antigen when located at the N-terminus or as whole antibodies or free monovalent scFv-fragments (FIG. 10). This phenomenon was, by way of reference Examples, extensively characterized with recombinant bifunctional single-chain molecules consisting at the N-terminus of the extra-cellular part of human CD80 (B7-1) followed at the C-terminus by different scFv-fragments derived form antibodies that specifically bind to the 17-1A-antigen (FIG. 1.1). Of four different 17-1A-specific antibodies, three of which were produced by murine hybridoma cell lines and one selected in vitro from a human combinatorial antibody library using the phage display method, none gave raise to a scFv-fragment that retains its antigen binding activity when fused with its N-terminus to the C-terminus of the human CD80-fragment and expressed as bifunctional single-chain molecule in CHO-cells (Examples 1-4). It is noteworthy that two of the murine antibody fragments (M79 and M74) bind to the 17-1A-antigen as N-terminal part of bi-specific single-chain antibodies (Mack, Proc. Natl. Acad. Sci. U.S.A. (1995) 7021-7025) as well as in the form of free monovalent scFv-fragments, the latter of which was also shown for the human 17-1A-specific antibody VD4.5VK8 (Example 3) derived in vitro from a phage library. All four specificities bind to the 17-1A-antigen in the form of whole antibody molecules. Accordingly, the technical problem underlying the present invention was to provide means and methods to identify bi- or multivalent polypeptides that comprise antibody binding sites capable of efficiently binding to the corresponding antigen. The solution to said technical problem is achieved by providing the embodiments characterized in the claims.

Thus, the present invention relates to a method of identifying a binding site domain having the capacity of binding to a predetermined epitope when positioned C-terminal of at least one further domain in a recombinant bi- or multivalent polypeptide comprising the steps of (a) testing a panel of binding site domains displayed on the surface of a biological display system as part of a fusion protein for binding to a predetermined epitope, wherein said fusion protein comprises an additional domain positioned N-terminal of said binding site domain and an amino acid sequence that mediates anchoring of the fusion protein to the surface of said display system; and (b) identifying a binding site domain that binds to said predetermined epitope.

Preferably, the binding site domain capable of binding to a preselected antigenic determinant comprises an amino acid sequence homologous with the sequence of a variable region of an immunoglobulin molecule capable of binding said preselected epitope.

The term "binding site domain" as used in accordance with the present invention denotes a domain comprising a three-dimensional structure capable of binding to an epitope.

The term "bi- or multivalent polypeptide" as used herein denotes a polypeptide comprising at least two amino acid sequences derived from different origins wherein one of said origins specifies the binding site domain.

In accordance with the present invention, the term "capacity of binding to an epitope" denotes the capacity of said binding site domain to enter and bind a corresponding epitope, like native antibodies or free scFv fragments. The term "panel" as used in accordance with the present invention relates to two or more pairs of the recited domains. Preferably, said panel is derived from a library such as a cDNA library, or, more preferably, a combinatorial library of, e.g., $V_H/V_L$ chains.

The fusion protein is capable of binding to a preselected epitope and preferably, has a specificity at least substantially identical to the binding specificity of the, e.g., immunoglobulin molecule where it is derived from. Such binding site domains can have a binding affinity of at least $10^6 M^{-1}$, preferably $10^8 M^{-1}$ and advantageously up to $10^{10} M^{-1}$ or higher. The additional domain present in the fusion protein may be linked by a polypeptide linker to the binding site domain. Furthermore, said additional domain may be of a predefined specificity or function. For example, the literature contains a host of references to the concept of targeting bioactive substances such as drugs, toxins, and enzymes to specific points in the body to destroy or locate malignant cells or to induce a localized drug or enzymatic effect. It has been proposed to achieve this effect by conjugating the bioactive substance to monoclonal antibodies (see, e.g., N.Y. Oxford University Press; and Ghose, (1978) J. Natl. Cancer Inst. 61:657-676). However, constructing corresponding targeted multifunctional proteins is hampered by the fact that the chimeric proteins loose their binding affinity and/or specificity due to the presence of extra sequences and guess work turned out to be insufficient to remedy this obstacle. The method of the present invention can solve this problem and thus can be used to prepare and identify such multi-functional proteins which substantially retain both, the binding affinity and the function of the additional domain(s). In a preferred embodiment of the method of the invention the binding site domain and said additional domain are linked by a polypeptide linker disposed between said binding site and said additional domain, wherein said polypeptide linker comprises plural, hydrophilic, peptide-bonded amino acids and connects the N-terminal end of said binding site and the C-terminal end of said additional domain. As well known, Fv, the minimum antibody fragment which contains a complete antigen recognition and binding site, consists of a dimer of one heavy and one light chain variable domain ($V_H$ and $V_L$) in noncovalent association. It is in this configuration that the three complementarity determining regions (CDRs) of each variable domain interact to define an antigen binding site on the surface of the $V_H$-$V_L$ dimer. Collectively, the six CDRs confer antigen binding specificity to the antibody. Frameworks (FRs) flanking the CDRs have a tertiary structure which is essentially conserved in native immunoglobulins of species as diverse as human and mouse. These FRs serve to hold the CDRs in their appropriate orientation. The constant domains are not required for binding function, but may aid in stabilizing $V_H$-$V_L$ interaction. Even a single variable domain (or half of an Fv comprising only three CDRs specific for an antigen) has the ability to recognize and bind antigen, although at a lower affinity than an entire binding site (Painter (1972) Biochem. 11:1327-1337). Hence, in a particularly preferred embodiment of the method of the invention, said binding site domain is a pair of $V_H$-$V_L$, $V_H$-$V_H$ or $V_L$-$V_L$ domains either of the same or of different immunoglobulins.

The order of $V_H$ and $V_L$ domains within the polypeptide chain is not decisive for the present invention, the order of domains given herein above may be reversed without any loss of function. It is important, however, that the $V_H$ and $V_L$ domains are arranged so that the antigen binding site can properly fold.

In accordance with the present invention, the term "identify" relates, in its broadest sense, to the identification of a clone that comprises the properly binding site domain, preferably raid clone can be purified and the sequence of the binding site domain, e.g., $V_H$ and $V_L$ domains may be determined.

Naturally, the method of the invention is not only applicable to the identification of a single pair of $V_H$ and $V_L$ domains, but may also be applied to the identification and isolation of a variety of such pairs.

Prior to establishing the method of the invention, a variety of parameters were considered that were expected to possibly influence the binding activity of scFv-antibody fragments located at the C-terminus of multivalent polypeptides, in particular of bifunctional singly-chain molecules. Thus, constructs with 5- and 15-amino acid glycin-serin-linkers between the CD80- and the scFv-fragment as well as alternative domain arrangements, namely $V_L$-$V_H$ and $V_H$-$V_L$ within the C-terminal scFv-fragment were produced and analysed for antigen binding (Examples 1 and 2).

However, antigen binding of scFv-fragments that lost their binding activity due to their position at the C-terminus of bifunctional single-chain molecules could not be reconstituted by using different linker lengths and/or by changing the arrangement of the $V_L$- and the $V_H$-domains in any Example tested. Surprisingly, it was now found in accordance with the present invention that by using a novel in vitro selection method based on the phage display technology (FIG. 11), scFv-antibody fragments that bind independently of their position within bifunctional single-chain fusion proteins could be isolated from, by way of Example, combinatorial antibody libraries, (Examples 5 and 6).

The present invention thus significantly extends the applicability of multivalent polypeptides such as bifunctional single-chain molecules.

To functionally simulate the C-terminal context in multivalent polypeptides exemplified by bifunctional single-chain constructs, the N-terminus of $V_H$-$V_L$-scFv-antibody fragments, respectively that of the $V_H$-domain, was fused to the C-terminus of a stretch of amino acids folding into a three-dimensional structure. Experimentally, this was achieved by employing the N2-domain of the gene III-product of filamentous phage (Krebber, FEBS Letters 377 (1995) 227-231). Accordingly, the N2-domain plays the role of a surrogate for any preferably functional domain located at the N-terminus of a pair of $V_H$ and $V_L$ domains within a bi- or multivalent single-chain protein. The "N-terminally blocked" scFv-fragment N2-$V_H$-$V_L$, respectively the C-terminus of $V_L$, was fused to an amino acid sequence that mediates anchoring of the fusion protein to the surface of a phage. Experimentally, this was effected by employing the N-terminus of the C-terminal CT-domain of the gene III-filamentous phage product (Barbas, Proc. Natl. Acad. Sci. U.S.A. 88 (1991) 7978-7982). In the following, the invention will be explained in more detail on the basis of the experiments that were actually carried out: The DNA encoding the fusion protein N2-$V_H$-$V_L$-CT can be cloned into a phagemid vector (e.g. pComb3H) and transformed into a male $E.$ $coli$-strain (e.g. XL1-blue) that will, after infection with a filamentous helper phage, produce phage particles carrying the N2-$V_H$-$V_L$-CT-fusion protein on their surface and containing a single-stranded copy of the corresponding DNA. This coupling of phenotype and genotype enables to select and enrich—by several rounds of panning on the antigen—from large repertoires of $V_H$/$V_L$-combinations those "N-terminally blocked" scFv-antibody fragments that nevertheless retain their antigen binding activity. To test the method of the invention, mice were immunized with recombinant soluble 17-1A-antigen; animals with detectable anti-17-1A serum antibody titer were sacrificed, total RNA was prepared from the murine spleen cells and reverse-transcribed into cDNA using random hexamer priming. The $V_L$- and $V_H$-repertoire of the current antibody response was amplified by PCR using $V_L$- and $V_H$-subfamily specific oligonucleotide primers and cloned into the phagemid vector pComb3H already containing the DNA-sequences encoding the N2- and the CT-domain of the gene III-product of filamentous phage. This combinatorial antibody library was transformed into the $E.$ $coli$-strain XL1-blue to subsequently proceed with the in vitro-selection by panning on immobilized 17-1A-antigen according to the phage display method (Winter, Annu. Rev. Immunol. 12 (1994) 433-455; Barbas, METHODS, A companion to Methods in Enzymology 2 (1991) 119-124). After the third, fourth and fifth round of panning, soluble N2-$V_H$-$V_L$-single chain fragments of individual clones were generated by the excision of the gene III-CT-sequence prior to the periplasmatic expression in $E.$ $coli$ and tested by ELISA for binding to immobilized 17-1A-antigen. The $V_L$- and $V_H$-regions of "N2-blocked" scFv-fragments that bound to the 17-1A-antigen were sequenced and subcloned into the mammalian expression vector pEF-DHFR already containing the coding sequence of the extra-cellular CD80-fragment thus resulting in a final construct that encodes a bifunctional single-chain protein with the CD80-fragment located at the N-terminal position (Example 7). In addition, one $V_H$-$V_L$-pair derived from a 17-1A-specific murine hybridoma cell line (Example 4) and another 17-1A-specific $V_H$-$V_L$-pair selected from a human combinatorial antibody library by the conventional phage display method (Example 3) were also cloned into this bifunctional context. The bifunctional single-chain constructs were transfected into DHFR-deficient CHO-cells using nucleoside-free culture medium for the primary selection and the protein expression was subsequently increased by gene amplification using the DHFR-inhibitor methotrexat at a final concentration of 20 nM. The recombinant bifunctional proteins were secreted into the culture supernatant; the culture supernatants from the different clones were analysed for antigen binding by ELISA on immobilized recombinant 17-1A-antigen (Example 8) and by flow cytometry on CHO-cells transfected with the transmembrane form of the 17-1A-antigen (Example 9). All of the nine different bifunctional single-chain constructs derived from the method of the invention proved to bind to the 17-1A-antigen as demonstrated in both binding assays (ELISA and FACS) (FIGS. 8.1, 8.2 and 9.1); both conventionally derived bifunctional single-chain constructs, however, failed to bind to the 17-1A-antigen (FIGS. 8.3, 8.4 and 9.1). As shown in Example 10 it could be further confirmed that specific antigen binding of scFv-antibody fragments obtained by the method of the invention does not depend on a particular further N-terminal domain (like the extracellular part of CD80) within a bifunctional single chain protein. Taken together, these data demonstrate that scFv-antibody fragments that retain their antigen binding activity at the C-terminal position of bifunctional single-chain proteins can be selectively obtained by the method of the invention involving an N-terminal surrogate domain simulating the effect of other functional domains fused to the N-terminus of scFv-antibody fragments. This exemplary approach can, by the person skilled in the art, be transferred to any other pair of $V_H$ and $V_L$ domains comprised in a multivalent polypeptide in the above indicated position(s).

In a preferred embodiment of the present invention, said biological display system is filamentous phage produced by bacteria transfected therewith, a baculovirus expression system, a ribosome based display system, a bacteriophage lambda display system or a bacterial surface expression system based, for example, on the ompA protein.

An Example of a ribosome display system has been described, for example, by Hanes, Proc. Natl. Acad. Sci. U.S.A. 94 (1997) 4937-4942. Examples of the other systems referred to above are well established in the art (Mottershead, Biochem. Biophys. Res. Commun. 238 (1997) 717-722; Sternberg, Proc. Natl. Acad. Sci. U.S.A. 92 (1995) 1609-1613; Stahl, Trends Biotechnol, 15 (1997) 185-192).

As regards the bacteria transfected with the phage, it is preferred that the bacteria are $E.$ $coli$.

Referring now to the experimental procedure used to explain the invention and described herein above, in a further preferred embodiment of the invention, said method comprises prior to step (a), the further step of (a'') transfecting bacteria with recombinant vectors encoding said fusion proteins. Preferably, said vectors are phagemid vectors.

In a further preferred embodiment of the invention, said method comprises prior to step (a''), the further step of (a') cloning a panel of nucleic acid molecules encoding the binding site domain, e.g., pairs of $V_H$ and $V_L$ domains into a vector.

In a most preferred embodiment of the invention, said panel of nucleic acid molecules is derived from immune competent cells of a mammal, fish or bird. This embodiment is particularly preferred insofar as it reflects the immune repertoire of the B-cell compartment of the mammal which may be amplified and cloned by RT-PCR using $V_L$- and $V_H$-specific oligonucleotide primers or primer sets.

In an additional preferred embodiment of the invention, said additional domain comprises at least 9 amino acids. Preferably, said additional domain is not sufficient to mediate phage infectivity when displayed on the surface of phage particles.

In a most preferred embodiment of the invention, said additional domain is or is derived from the N2-domain of the gene III product of filamentous phage. Preferably, N2 is not capable of mediating infectivity of the phage.

In a preferred embodiment of the invention, said sequence mediating said anchoring is or is derived from the C-terminal CT-domain of the gene III product of filamentous phage. However, other suitable domains known to be capable of mediating anchoring to surfaces of, e.g., phage displays may be used as well.

In a further preferred embodiment of the invention, said bi- or multivalent polypeptide is a bi- or multifunctional polypeptide.

In a most preferred embodiment of the invention, said at least one further domain comprises a polypeptide selected from the group consisting of effector proteins having a conformation suitable for biological activity, amino acid sequences capable of sequestering an ion, and amino acid sequences capable of selective binding to a solid support. Preferably, said effector protein is an enzyme, toxin, receptor, binding site, biosynthetic antibody binding site, growth factor, cell-differentiation factor, lymphokine, cytokine, hormone, a remotely detectable moiety, or anti-metabolite. Furthermore, said sequence capable of sequestering an ion is preferably selected from calmodulin, methallothionein, a fragment thereof, or an amino acid sequence rich in at least one of glutamic acid, aspartic acid, lysine, and arginine. In addition, said polypeptide sequence capable of selective binding to a solid support can be a positively or negatively charged amino acid sequence, a cysteine-containing amino acid sequence, avidin, streptavidin, or a fragment of *Staphyloccocus* protein A.

The effector proteins and amino acid sequences described above may be present in a proform which itself is either active or not and which may be removed, when, e.g., entering a certain cellular environment.

In a most preferred embodiment of the invention, said receptor is a costimulatory surface molecule important for T-cell activation or comprises an epitope binding site or a hormone binding site.

In a further most preferred embodiment of the invention, said costimulatory surface molecule is CD80 (B7-1), CD86 (B7-2), CD58 (LFA-3) or CD54 (ICAM-1).

In a further most preferred embodiment of the invention, said epitope binding site is embedded in a pair of $V_H$-$V_L$, $V_H$-$V_H$ and $V_L$-$V_L$ domains.

In a preferred embodiment of the invention, said $V_H$ and/or $V_L$ domains are connected by a flexible linker, preferably by a polypeptide linker disposed between said domains, wherein said polypeptide linker comprises plural, hydrophilic, peptide-bonded amino acids of a length sufficient to span the distance between the C-terminal end of one of said domains and the N-terminal end of the other of said domains when said fusion protein assumes a conformation suitable for binding when disposed in aqueous solution.

In a further preferred embodiment of the invention, the identification of said binding site domain comprises the steps of (a) removing said amino acid sequence that mediates anchoring of the fusion protein to the surface of a phage from said fusion protein;
(b) periplasmatically expressing the nucleic acid molecules encoding the remainder of said fusion protein in bacteria; and
(c) verifying whether said binding site domain binds to said predetermined epitope.

In another embodiment the present invention relates to a recombinant vector as defined in the above-described embodiments and to a host cell harboring and capable of expressing such a recombinant vector.

In a further preferred embodiment of the invention, the kit comprises (a) the described recombinant vector or a panel of recombinant vectors encoding a panel of fusion proteins as defined in the embodiments described above; and/or
(b) the described host cell or a bacterial library transfected with a panel of vectors as defined in (a).

Furthermore, the present invention relates to a binding site domain or fusion protein obtainable by the method of the invention as characterized in the embodiments above. Advantageously, the amino acid sequence that mediate anchoring of the fusion protein to the surface of a phage of said fusion protein is removed from the fusion protein. Thus, the resultant fusion protein may only comprise the binding site domain and an additional domain, preferably an effector protein as described above.

In a preferred embodiment of the present invention, the binding site domain, for example contained in a fusion protein comprises at least one complementarity determined region (CDR) of the scFv fragment shown in any one of FIGS. 6.3 to 6.10 and 7. The person skilled in the art knew that each variable domain comprises three hypervariable regions, sometimes called complementarity determining regions or "CDRs" flanked by four relatively conserved framework regions or "FRs". The CDRs contained in the variable regions shown in FIGS. 6.3 to 6.10 and 7 can be determined according to Kabat, *Sequences of Proteins of Immunological Interest* (U.S. Department of Health and Human Services, third edition, 1983, fourth edition, 1987, fifth edition 1990). The person skilled in the art will readily appreciate that the binding site domain or fusion protein identified according to the method of the invention or at least one CDR derived therefrom can be used for the construction of other polypeptides or antibodies of desired specificity and biological function. Thus, the present invention also relates to polypeptides and antibodies comprising a binding site domain or fusion protein of the invention. Preferably, said polypeptide or antibody comprises the amino acid sequence as depicted in any one of FIGS. 6.3 to 6.10 and 7. The person skilled in the art will readily appreciate that using the binding sites or CDRs described above antibodies can be constructed according to methods known in the art, e.g., as described in EP-A1 0 451 216 and EP-A1 0 549 581.

Yet in a further embodiment, the present invention relates to polynucleotides which upon expression encode the above-described polypeptides and antibodies. Said polynucleotides may be fused to suitable expression control sequences known in the art to ensure proper transcription and translation of the polypeptide.

Furthermore, the polynucleotides may be comprised in a vector which further comprises a selectable marker.

In a still further embodiment, the present invention relates to a cell containing the polynucleotide described above. Preferably, said cell is a mammalian cell if therapeutic uses of the polypeptide are envisaged. Of course, yeast and bacterial cells may serve as well, in particular if the produced polypeptide is used as a diagnostic means.

In a further embodiment, the present invention thus relates to a process for the preparation of a fusion protein obtainable by the method according to the invention, a polypeptide or antibody as described above comprising cultivating a cell of the invention under conditions suitable for the expression of the fusion protein or polypeptide and isolating the fusion protein, polypeptide or antibody from the cell culture medium.

Moreover, the present invention relates to a pharmaceutical composition containing a fusion protein, polypeptide or antibody of the invention and optionally a pharmaceutically acceptable carrier.

As to a further embodiment, the present invention relates to a diagnostic composition comprising a fusion protein, polypeptide or antibody as described above and optionally suitable means for detection.

The present invention allows recombinant production of single chain binding sites having affinity and specificity for a predetermined epitope. This technology has been developed and is disclosed herein. In view of this disclosure, persons skilled in recombinant DNA technology, protein design, and protein chemistry can produce such sites which, when disposed in solution, have high binding constants (usually at least $10^6$, preferably $10^8 M^{-1}$) and excellent specificity. As is evident from the foregoing, the invention provides a large family of binding site domains and fusion proteins as well as polypeptides comprising such binding site domains and fusion proteins for any use in therapeutic and diagnostic approaches. It will be apparent to those skilled in the art that the binding site domains and fusion proteins can be further coupled to other moieties for, e.g., drug targeting and imaging applications. Such coupling may be conducted chemically after expression of the fusion proteins or polypeptides to site of attachment or the coupling product may be engineered into the polypeptide of the invention at the DNA level. The DNAs are then expressed in a suitable host system, and the expressed proteins are collected and renatured, if necessary. As described above, the binding site domain is preferably derived from the variable region of antibodies, preferably monoclonal antibodies. In this respect, hybridoma technology enables production of cell lines secreting antibody to essentially any desired substance that produces an immune response. RNA encoding the light and heavy chains of the immunoglobulin can then be obtained from the cytoplasm of the hydridoma. The 5+ end portion of the mRNA can be used to prepare cDNA to be used in the method of the present invention.

The DNA encoding the fusion proteins obtained according to the method of the invention can then be expressed in cells, preferably mammalian cells.

Depending on the host cell, renaturation techniques may be required to attain proper conformation. The various proteins can then be further tested for binding ability, and one having appropriate affinity can be selected for incorporation into a polypeptide of the type described above. If necessary, point substitutions seeking to optimize binding may be made in the DNA using conventional cassette mutagenesis or other protein engineering methodology such as is disclosed below.

Preparation of the polypeptides of the invention also is dependent on knowledge of the amino acid sequence (or corresponding DNA or RNA sequence) of bioactive proteins such as enzymes, toxins, growth factors, cell differentiation factors, receptors, anti-metabolites, hormones or various cytokines or lymphokines. Such sequences are reported in the literature and available through computerized data banks.

The DNA sequences of the binding site and the second protein domain are fused using conventional techniques, or assembled from synthesized oligonucleotides, and then expressed using equally conventional techniques.

The processes for manipulating, amplifying, and recombining DNA which encode amino acid sequences of interest are generally well known in the art, and therefore, not described in detail herein. Methods of identifying and isolating genes encoding antibodies of interest are well understood, and described in the application and other literature. In general, the methods involve selecting genetic material coding for amino acids which define the proteins of interest, including the CDRs and FRs of interest, according to the genetic code.

Accordingly, the construction of DNAs encoding proteins as disclosed herein can be done using known techniques involving the use of various restriction enzymes which make sequence specific cuts in DNA to produce blunt ends or cohesive ends, DNA ligases, techniques enabling enzymatic addition of sticky ends to blunt-ended DNA, construction of synthetic DNAs by assembly of short or medium length oligonucleotides, cDNA synthesis techniques, and synthetic probes for isolating immunoglobulin or other bioactive protein genes. Various promoter sequences and other regulatory DNA sequences used in achieving expression, and various types of host cells are also known and available. Conventional transfection techniques, and equally conventional techniques for cloning and subcloning DNA are useful in the practice of this invention and known to those skilled in the art. Various types of vectors may be used such as plasmids and viruses including animal viruses and bacteriophages. The vectors may exploit various marker genes which impart to a successfully transfected cell a detectable phenotypic property that can be used to identify which of a family of clones has successfully incorporated the recombinant DNA of the vector.

These and other embodiments are disclosed and encompassed by the description and Examples of the present invention. For example, further literature concerning any one of the methods, uses and compounds to be employed in accordance with the present invention may be retrieved from public libraries, using for example electronic devices. For example the public database "Medline" may be utilized which is available on the Internet. An overview of patent information in biotechnology and a survey of relevant sources of patent information useful for retrospective searching and for current awareness is given in Berks, TIBTECH 12 (1994), 352-364.

The figures show:

FIG. 1.1: Design of various bifunctional CD80-scFv-constructs showin the construction elements on the protein-level. $V_H$ indicates the variable region of the Ig-heavy chain, $V_L$ that of the Ig-light chain. The single-chain-Fv-fragments used in the present invention are given in the Examples 1, 2, 3, 4 and 9.

FIG. 1.2: DNA sequence (SEQ ID NO: 49) designated CTI that was cloned into the multiple cloning site of the Bluescript KS vector (GenBank® accession number X52327) by using the restriction sites XbaI and SalI in order to increase the number of possible cloning sites. CTI-derived restriction enzyme cleavage sites are shown.

FIG. 1.3: Design of various bifunctional CD80-scFv-constructs showing the construction elements on the DNA-level as well as the restriction enzyme cleavage sites used.

FIG. 1.4: ELISA-analysis of the cell-culture supernatant obtained from CHO cells transfected with the expression plasmid pEF-DHFR+CTI+CD80-M79scFv($V_L/V_H$) including the coding sequence of the short $(Gly_4Ser_1)_1$ linker. 96 well ELISA plates were incubated with 50 µl of soluble 17-1A antigen (50 µg/ml) per well. Subsequently pure cell-culture supernatant dilutions thereof were added as indicated. Detection was performed by a murine IgG1 anti His-tag antibody (dianova, Hamburg) diluted 1:200 and a peroxidase conjugated polyclonal goat anti mouse IgG (Fc) antibody (dianova, Hamburg) diluted 1:5000. The anti-17-1A/anti-CD3 bispecific-single-chain antibody (Mack, Proc. Natl. Acad. Sci. USA 92 (1995) 7021-7025) was used as positive control. As negative control, wells were incubated with phosphate buffered saline. The ELISA was developed by ABTS-substrate solution as described in Example 8. The OD-values were measured at 405 nm by an ELISA reader.

FIG. 1.5: ELISA-analysis of the cell-culture supernatant obtained from CHO-cells transfected with the expression plasmid pEF-DHFR+CTI+CD80-M79scFv($V_L/V_H$) including the coding sequence of the short $(Gly_4Ser_1)_1$ linker. 96 well ELISA plates were incubated with 50 µl soluble 17-1A antigen (50 µg/ml) per well. Subsequently pure cell-culture supernatant and dilutions thereof were added as indicated. Detection was performed by a murine IgG1-anti CD80 antibody diluted 1:1000 followed by a peroxidase conjugated polyclonal goat anti mouse IgG (Fc) antibody (dianova, Hamburg) diluted 1:5000. The anti-17-1A/anti-CD3 bispecific-single-chain antibody (Mack, Proc. Natl. Acad. Sci. USA 92 (1995) 7021-7025). was used as positive control and detected as described in FIG. 1.4. As negative control, wells were incubated with phosphate buffered saline. The ELISA was developed by an ABTS-substrate solution as described in Example 8. The OD-values were measured at 405 nm by an ELISA reader.

FIG. 1.6: ELISA-analysis of the purified recombinant CD80-M79scFv($V_L/V_H$)-construct with a short $(Gly_4Ser_1)_1$ linker obtained by purification from cell-culture supernatant using a Ni-NTA-column as described (Mack, Proc. Natl. Acad. Sci. USA 92 (1995) 7021-7025). 96 well ELISA plates were coated overnight at 4° C. with pure eluate from the Ni-NTA-column and dilutions thereof as indicated. Subsequently bound recombinant protein was detected by a murine IgG1-anti CD80 antibody diluted 1:1000 or by a murine IgG1-anti His-tag antibody (dianova, Hamburg) diluted 1:200 followed by a peroxidase conjugated polyclonal goat anti mouse IgG (Fc) antibody (dianova, Hamburg) respectively diluted 1:5000. As negative control wells were coated overnight at 4° C. with 3% BSA in phosphate buffered saline. The ELISA was developed by an ABTS-substrate solution as described in Example 8. The OD-values were measured at 405 nm by an ELISA reader.

FIG. 1.7: ELISA-analysis of the cell-culture supernatant obtained from CHO-cells transfected with the expression plasmid pEF-DHFR+CTI+CD80-M79scFv($V_H/V_L$) including the coding sequence of the short $(Gly_4Ser_1)_1$ linker. 96 well ELISA plates were incubated with soluble 17-1A antigen (50 µg/ml) per well. Subsequently pure cell-culture supernatant and dilutions: thereof were added as indicated. Detection was performed by a murine IgG1-anti CD80 antibody diluted 1:1000 followed by a peroxidase conjugated polyclonal goat anti-mouse IgG (Fc) antibody (dianova, Hamburg) diluted 1:5000. The anti-17-1A/anti-CD3 bispecific-single-chain antibody (Mack, Proc. Natl. Acad. Sci. USA 92 (1995) 7021-7025) was used as positive control and detected as described in FIG. 1.4. As negative control wells were incubated with phosphat buffered saline. The ELISA was processed by an ABTS-substrate solution as described in Example 8. The OD-values were measured at 405 nm by an ELISA reader.

FIG. 1.8: DNA-sequence (SEQ ID NOS: 50-51) of the double-stranded oligonucleotide designated ACCGS15BAM with single-stranded overhangs compatible with those of restriction enzymes BspEI and BamHI. Amino acids (SEQ ID NO: 52) encoded by the nucleotide sequence are shown.

FIG. 1.9: ELISA-analysis of the cell-culture supernatant and of its dilutions obtained from CHO-cells transfected with the expression plasmid pEF-DHFR+CTI+CD80-M79scFv ($V_H/V_L$) including the coding sequence of the long $(Gly_4Ser_1)_3$ linker. 96 well ELISA plates were incubated with 50 µl soluble 17-1A antigen (50 µg/ml) per well. Subsequently pure cell-culture supernatant and dilutions thereof were added as indicated. Bound protein was detected by a murine anti His-tag antibody (dianova, Hamburg) diluted 1:200 followed by a peroxidase conjugated polyclonal goat anti mouse IgG (Fc) antibody (dianova, Hamburg) diluted 1:5000. The anti-17-1A/anti-CD3 bispecific-single-chain antibody antibody (Mack, Proc. Natl. Acad. Sci. USA 92 (1995) 7021-7025) was used as positive control. As negative control wells were incubated with phosphat buffered saline. The ELISA was developed by an ABTS-substrate solution as described in Example 8. The OD-values were measured at 405 nm by an ELISA reader.

FIG. 2.1: ELISA-analysis of the cell-culture supernatant obtained from CHO-cells transfected with the expression plasmids pEF-DHFR+CTI+CD80-M74scFv($V_H/V_L$) or pEF-DHFR+CTI+CD80-M74scFv($V_L/V_H$) including the coding sequence of the long $(Gly_4Ser_1)_3$ or short $(Gly_4Ser_1)_1$ linker respectively. 96 well ELISA plates were incubated with 50 µl soluble 17-1A antigen (50 µg/ml) per well. Subsequently pure cell-culture supernatant and dilutions thereof were added as indicated. Detection was performed by a murine IgG1 anti His-tag antibody (dianova, Hamburg) diluted 1:1000 and followed by a peroxidase conjugated polyclonal goat anti mouse IgG (Fc) antibody (dianova, Hamburg) diluted 1:5000. The anti-17-1A/antiCD3 bispecific-single-chain antibody antibody (Mack, Proc. Natl. Acad. Sci. USA 92 (1995) 7021-7025) was used as positive control and detected as described in FIG. 1.4. As negative control wells were incubated with phosphat buffered saline. The ELISA was developed by an ABTS-substrate solution as described in Example 8. The OD-values were measured at 405 nm by an ELISA reader.

FIG. 2.2: ELISA-analysis of the cell-culture supernatant obtained from CHO-cells transfected with the expression plasmids pEF-DHFR+CTI+CD80-M74scFv($V_H/V_L$) or pEF-DHFR+CTI+CD80-M74scFv($V_L/V_H$) including the coding sequence of the long $(Gly_4Ser_1)_3$ or short $(Gly_4Ser_1)_1$ linker respectively. 96 well ELISA plates were incubated with 50 µl soluble 17-1A antigen (50 µg/ml) per well. Subsequently pure cell-culture supernatant and dilutions thereof were added as indicated. Detection was performed by a murine IgG1-anti CD80 antibody diluted 1:1000 followed by a peroxidase conjugated polyclonal goat anti mouse IgG (Fc) antibody (dianova, Hamburg) diluted 1:5000. The anti-17-1A/anti-CD3 bispecific-single-chain antibody antibody (Mack, Proc. Natl. Acad. Sci. USA 92 (1995) 7021-7025) was used as positive control and detected as described in FIG. 1.4. As negative control wells were incubated with phosphat buffered saline. The ELISA was developed by an ABTS-substrate solution as described in Example 8. The OD-values were measured at 405 nm by an ELISA reader.

FIG. 3.1: DNA- and protein sequence (SEQ ID NOS: 53-54) of the human D4.5. heavy chain variable region ($V_H$ of the human anti-17-1A-antibody VD4.5VK8). Number indicate the nucleotide (nt) positions, amino acids are presented in the single letter code. CDR1 includes nt 91 to nt 105, CDR2 nt 148 to nt 198, CDR3 nt 292 to nt 351.

FIG. 3.2: DNA- and protein sequence (SEQ ID NOS: 55-56) of the human kappa 8 light chain variable region ($V_L$ of the human anti-17-1A-antibody VD4.5VK8). Numbers indicate the nucleotide (nt) positions, amino acids are presented in single letter code. CDR1 includes nt 70 to nt 102, CDR2 nt 148 to nt 168, CDR3 nt 265 to nt 294.

FIG. 3.3: ELISA-analysis of free scFv-fragment ($V_H/V_L$) of the human anti 17-1A antibody VD4.5VK8. The sequence encoding the N2-domain was excised from the plasmid pComb3H5BHis-VD4.5VK8scFv (Example 3) using the restriction enzymes SalI and XhoI followed by religation of the vector. The resulting plasmid was used for periplasmatic expression of soluble VD4.5VK8-scFv-fragment in E. coli XL1-blue according to the procedure described in Example 6. Analysis of binding to the 17-1A-antigen of soluble VD4.5VK8-scFv-fragment was performed as follows: 96 well ELISA plates were incubated with soluble 17-1A antigen (50 µg/ml). Subsequently, pure periplasma preparation was added. Detection was performed by a murine IgG1-anti-His-tag antibody diluted 1:250 followed by a peroxidase conjugated polyclonal goat anti mouse IgG (Fc) antibody (dianova, Hamburg) diluted 1:5000. The anti-17-1A/anti-CD3 bispecific-single-chain antibody (Mack, Proc. Natl. Acad. Sci. USA 92 (1995) 7021-7025) was used as positive control and detected as described in FIG. 1.4. As negative control, an irrelevant periplasma preparation was used. The ELISA was developed by an ABTS-substrate solution as described in Example 8. The OD-values were measured at 405 nm by an ELISA reader.

FIG. 3.4: NS3 Frame: DNA-sequence (SEQ ID NO: 57) designated L-F-NS3Frame that was cloned into the multi-cloning site of the vector Bluescript-KS-CTI (FIG. 1.2) by using the restriction sites EcoRI and SalI in order to increase the number of possible cloning sites. Cloning sites derived from L-F-NS3Frame are shown.

FIG. 4: ELISA-analysis of the cell-culture supernatant obtained from CHO-cells transfected with the light and heavy chain of the chimerized anti 17-1A antibody MACH (Example 4). 96 well ELISA plates were incubated with soluble 17-1A antigen (50 μg/ml). Subsequently, pure cell-culture supernatant and dilutions thereof were added as indicated. Detection was performed by a biotinylated anti human IgG antibody followed by streptavidin. Supernatant of the parent murine anti-17-1A antibody MACH and dilutions thereof were used as positive control and detected by a biotiylated anti-mouse IgG antibody. As negative control, phosphat buffered saline was used. The ELISA was developed by an ABTS-substrate solution as described in Example 8. The OD-values were measured at 405 nm by an ELISA reader.

FIG. 5.1: Cloning site of pComb3H with important restriction sites. The following abbreviations were used: P, lac-promotor: $V_L$, variable light chain domain: CL, constant light chain domain; $V_H$, variable heavy chain domain; CH1, constant heavy chain domain; L1/2, procaryotic leader sequences (L1=ompA, L2=pelB).

FIG. 5.2: DNA sequence (SEQ ID NO: 58) of the multiple cloning site of pComb3H5BHis showing important restriction enzyme cleavage sites as well as the amino acid sequence (SEQ ID NO: 59) of the Glycine-Serine-linker and that of the N2-domain of the gene III-product of filamentous phage. The DNA-sequence encoding the N2-domain starts at nt 19 and ends at nt 411.

FIG. 5.3: Cloning site of pComb3H5BHis with important restriction sites. The following abbreviations were used: P, lac-promotor; $V_K$, variable kappa light chain domain; $V_H$, variable heavy chain domain; ompA, procaryotic leader sequence; N2 is linked to $V_H$ by a $Gly_4Ser_1$-linker; $V_H$ is linked to $V_K$ by a $(Gly_4Ser_1)_3$-linker.

FIG. 6.1: Scheme of the pComb3H5BHis-plasmid and the fully expressed M13-phage. At the top the organization of leader (L) ompA, $V_H$, $V_K$ and gene III is shown. A representative expressed M13-phage-particle (bottom) displays on its surface the phenotype of a certain scFv-fragment consisting of $V_H$ and $V_K$ linked with its C-terminus to the gene III product and with its N-terminus in the N2-domain and contains the corresponding genotype as single-stranded DNA encoding said protein elements as a single polypeptide chain.

FIG. 6.2: ELISA-analysis of 17-1A-specific scFv protein fragments generated by the method of invention. Periplasma preparations of soluble scFv protein fragments containing the N2-domain at their N-terminus and consisting of one single mouse Vkappa- and one single Vheavy chain-domain, respectively were added pure to an ELISA-plate that had been coated with soluble 17-1A antigen. Detection was performed by a murine IgG1 anti-his-tag antibody followed by a peroxidase conjugated polyclonal goat anti mouse-Ig(Fc) antibody. The ELISA was developed by an ABTS-substrate solution as described in Example 8. The OD-values (y-axis) were measured at 405 nm by an ELISA-reader. Clones are presented on the x-axis, the lower number indicates the round of panning, the number above indicates the tested clone of this round. Clones 0-1 to 0-9 have a combination of unselected scFv-fragments and therefore can be seen as negative controls. the positive control is an anti 17-1A/anti-CD3 bispecific single chain Fv antibody (Mack, Proc. Natl. Acad. Sci. USA 92 (1995) 7021-7025).

FIG. 6.3: DNA- and protein-sequence (SEQ ID NOS: 60-61) of the mouse scFv fragment 3-1. Numbers indicate the nucleotide (nt) positions, amino acids (aa) are presented in single letter code. The first four aa of the $V_H$-fragment are encoded by the plasmid pComb3H5BHis. The encoding DNA sequence for the V-region of the heavy chain starts at nt 1 and ends at nt 360 followed by a $(G_4S_1)_3$-linker. The coding DNA sequence for the V-region of the kappa chain starts at nt 406 and ends at nt 726.

FIG. 6.4: DNA- and protein-sequence (SEQ ID NOS: 62-63) of the mouse scFv fragment 3-5. Numbers indicate the nucleotide (nt) positions, amino acids (aa) are presented in single letter code. The first four aa of the $V_H$-fragment are encoded by the plasmid pComb3H5BHis. The encoding DNA sequence for the V-region of the heavy chain starts at nt 1 and ends at nt 372 followed by a $(G_4S_1)_3$-linker. The coding DNA sequence for the V-region of the kappa chain starts at nt 418 and ends at nt 753.

FIG. 6.5: DNA- and protein-sequence (SEQ ID NOS: 64-65) of the mouse scFv fragment 3-8. Numbers indicate the nucleotide (nt) positions, amino acids (aa) are presented in single letter code. The first four aa of the $V_H$-fragment are encoded by the plasmid pComb3H5BHis. The encoding DNA sequence for the V-region of the heavy chain starts at nt 1 and ends at nt 360 followed by a $(G_4S_1)_3$-linker. The coding DNA sequence for the V-region of the kappa chain starts at nt 406 and ends at nt 726.

FIG. 6.6: DNA- and protein-sequence (SEQ ID NOS: 66-67) of the mouse scFv fragment 4-1. Numbers indicate the nucleotide (nt) positions, amino acids (aa) are presented in single letter code. The first four aa of the $V_H$-fragment are encoded by the plasmid pComb3H5BHis. The encoding DNA sequence for the V-region of the heavy chain starts at nt 1 and ends at nt 360 followed by a $(G_4S_1)_3$-linker. The coding DNA sequence for the V-region of the kappa chain starts at nt 406 and ends at nt 744.

FIG. 6.7: DNA- and protein-sequence (SEQ ID NOS: 68-69) of the mouse scFv fragment 4-4. Numbers indicate the nucleotide (nt) positions, amino acids (aa) are presented in single letter code. The first four aa of the $V_H$-fragment are encoded by the plasmid pComb3H5BHis. The encoding DNA sequence for the V-region of the heavy chain starts at nt 1 and ends at nt 360 followed by a $(G_4S_1)_3$-linker. The coding DNA sequence for the V-region of the kappa chain starts at nt 406 and ends at nt 726.

FIG. 6.8: DNA- and protein-sequence (SEQ ID NOS: 70-71) of the mouse scFv fragment 4-7. Numbers indicate the nucleotide (nt) positions, amino acids (aa) are presented in single letter code. The first four aa of the $V_H$-fragment are encoded by the plasmid pComb3H5BHis. The encoding DNA sequence for the V-region of the heavy chain starts at nt 1 and ends at nt 372 followed by a $(G_4S_1)_3$-linker. The coding DNA sequence for the V-region of the kappa chain starts at nt 417 and ends at nt 753.

FIG. 6.9: DNA- and protein-sequence (SEQ ID NOS: 72-73) of the mouse scFv fragment 5-3. Numbers indicate the nucleotide (nt) positions, amino acids (aa) are presented in single letter code. The first four aa of the $V_H$-fragment are encoded by the plasmid pComb3H5BHis. The encoding DNA sequence for the V-region of the heavy chain starts at nt 1 and ends at nt 348 followed by a $(G_4S_1)_3$-linker. The coding DNA sequence for the V-region of the kappa chain starts at nt 394 and ends at nt 717.

FIG. 6.10: DNA- and protein-sequence (SEQ ID NOS: 74-75) of the mouse scFv fragment 5-10. Numbers indicate the nucleotide (nt) positions, amino acids (aa) are presented in single letter code. The first four aa of the $V_H$-fragment are encoded by the plasmid pComb3H5BHis. The encoding DNA sequence for the V-region of the heavy chain starts at nt 1 and ends at nt 360 followed by a $(G_4S_1)_3$-linker. The coding DNA sequence for the V-region of the kappa chain starts at nt 406 and ends at nt 744.

FIG. 7: DNA- and protein-sequence (SEQ ID NOS: 76-77) of the mouse scFv fragment 5-13. Numbers indicate the nucleotide (nt) positions, amino acids (aa) are presented in single letter code. The first four aa of the $V_H$-fragment are encoded by the plasmid pComb3H5BHis. The encoding DNA sequence for the V-region of the heavy chain starts at nt 1 and ends at nt 360 followed by a $(G_4S_1)_3$-linker. The coding DNA sequence for the V-region of the kappa chain starts at nt 406 and ends at nt 744.

FIG. 8.1: ELISA analysis of nine cell-culture supernatants (primary selection step (PS)) obtained from CHO cells transfected with the expression plasmids pEF-DHFR+CTI+CD80+scFv 17-1A clones 3-1 to 5-13. 96 well U bottom ELISA plates were incubated with 50 μl of soluble 17-1A antigen (50 μg/ml) per well. Antibody constructs as culture supernatants were added pure and at following dilutions: 1:2, 1:4, 1:8. Detection was performed by a CD80-specific monoclonal antibody diluted 1:1000 in PBS 1% BSA followed by a polyclonal peroxidase-conjugated Goat Anti-Mouse IgG-antibody (Fc-specific) (dianova, Hamburg) diluted 1:5000. The ELISA was finally developed by adding the ABTS substrate solution as described in Example 8. For negative controls, the plates were incubated with PBS instead of bifunctional antibody constructs. The OD-values were measured by an ELISA reader at 405 nm.

FIG. 8.2: ELISA analysis of nine cell-culture supernatants (1. Amplification step (20 nM MTX) (1. Amp)) obtained from CHO cells transfected with the expression plasmids pEF-DHFR+CTI⇆CD80+scFv 17-1A clones 3-1 to 5-13. 96 well U bottom ELISA plates were incubated with 50 μl of soluble 17-1A antigen (50 μg/ml) per well. Antibody constructs as culture supernatants were added pure and at following dilutions: 1:2, 1:4, 1:8. Detection was performed by a CD80-specific monoclonal antibody diluted 1:1000 in PBS 1% BSA followed by a polyclonal peroxidase-conjugated Goat Anti-Mouse IgG-antibody (Fc-specific) (dianova, Hamburg) diluted 1:5000. The ELISA was finally developed by adding the ABTS substrate solution as described in Example 8. For negative controls, the plates were incubated with PBS instead of bifunctional antibody constructs. The OD-values were measured by an ELISA reader at 405 nm.

FIG. 8.3: ELISA analysis of two cell-culture supernatants (primary selection step (PS)) from 17-1A specific bifunctional CD80-scFv-constructs, which were generated as described in Example 3 and 4. 96 well U bottom ELISA plates were incubated with 50 μl of soluble 17-1A antigen (50 μg/ml) per well. Antibody constructs as culture supernatants were added pure and at following dilutions: 1:2, 1:4, 1:8. Detection was performed by a CD80-specific monoclonal antibody diluted 1:1000 in PBS 1% BSA followed by a polyclonal peroxidase-conjugated Goat Anti-Mouse IgG-antibody (Fc-specific) (dianova, Hamburg) diluted 1:5000. The ELISA was finally developed by adding the ABTS substrate as described in Example 8. For negative controls, the plates were incubated with PBS instead of bifunctional antibody constructs. As positive control served a supernatant generated in Example 7. The OD-values were measured at 405 nm using an ELISA-reader.

FIG. 8.4: ELISA analysis of two cell-culture supernatants (1. Amplification step (20 nM MTX) (1. Amp)) from 17-1A specific bifunctional CD80-scFv-constructs, which were generated as described in Example 3 and 4. 96 well U bottom ELISA plates were incubated with 50 μl of soluble 17-1A antigen (50 μg/ml) per well. Antibody constructs as culture supernatants were added pure and at following dilutions: 1:2, 1:4, 1:8. Detection was performed by a CD80-specific monoclonal antibody diluted 1:1000 in PBS 1% BSA followed by a polyclonal peroxidase-conjugated Goat Anti-Mouse IgG-antibody (Fc-specific) (dianova, Hamburg) diluted 1:5000. The ELISA was finally developed by adding the ABTS substrate solution as described in Example 8. For negative controls, the plates were incubated with PBS instead of bifunctional antibody constructs. As positive control a supernatant generated in Example 7 was used. The OD-values were measured at 405 nm using an ELISA-reader.

FIG. 9.1: Binding studies of 17-1A specific bifunctional CD80-scFv-constructs on 17-1A transfected (filled lines) and untransfected CHO cells (broken lines) detected by flow cytometry. $5 \times 10^5$ cells were incubated in 50 μl undiluted cell-culture supernatant containing the corresponding bifunctional construct. Bound bifunctional CD80-scFv-constructs were detected by a monoclonal anti-CD80 antibody (Immunotech. Cat. No.: 1449) diluted 1:20 in 50 μl PBS. Incubation conditions were the same as described in FIG. 8.5. Bound CD80-antibody was finally detected by a fluorescein conjugated polyclonal Goat Anti-Mouse IgG+IgM (H+L) antibody diluted 1:100 in PBS. Incubation was again carried out for 30 minutes on ice. For the fixation of fluorescein-labeled cells 1% paraformaldehyd in PBS was used. As first negative control untransfected CHO was used. The second negative control contained 17-1A-transfected cells that were incubated with PBS instead of bifunctional CD80-scFv-constructs. Cells were analysed by flow cytometry on a FACS scan (Becton Dickenson).

FIG. 9.2: FACS-Control of the CHO cells after transfection with 17-1A. The expression of transmembrane 17-1A was increased by stepwise gene amplification induced by subsequent addition of increasing concentrations of the DHFR inhibitor MTX to a final concentration of 500 nM, with concentration steps in between 20 nM and 100 nM. These cells were tested for membrane expression of 17-1A by flow cytometry at a concentration of 10 μg/ml of the 17-1A-specific antibody M79 (Göttlinger, Int. J. Cancer 38 (1986), 47-53) followed by a FITC-labeled polyclonal Goat Anti Mouse IgG+IgM (H+L) antibody diluted 1:100 in PBS. As negative control untransfected CHO cells were used whereas the 17-1A-positive human gastric cancer cell-line Kato, obtained from ATCC served as positive control.

FIG. 10: Principle of constructing bifunctional single-chain proteins.

Figure 11:
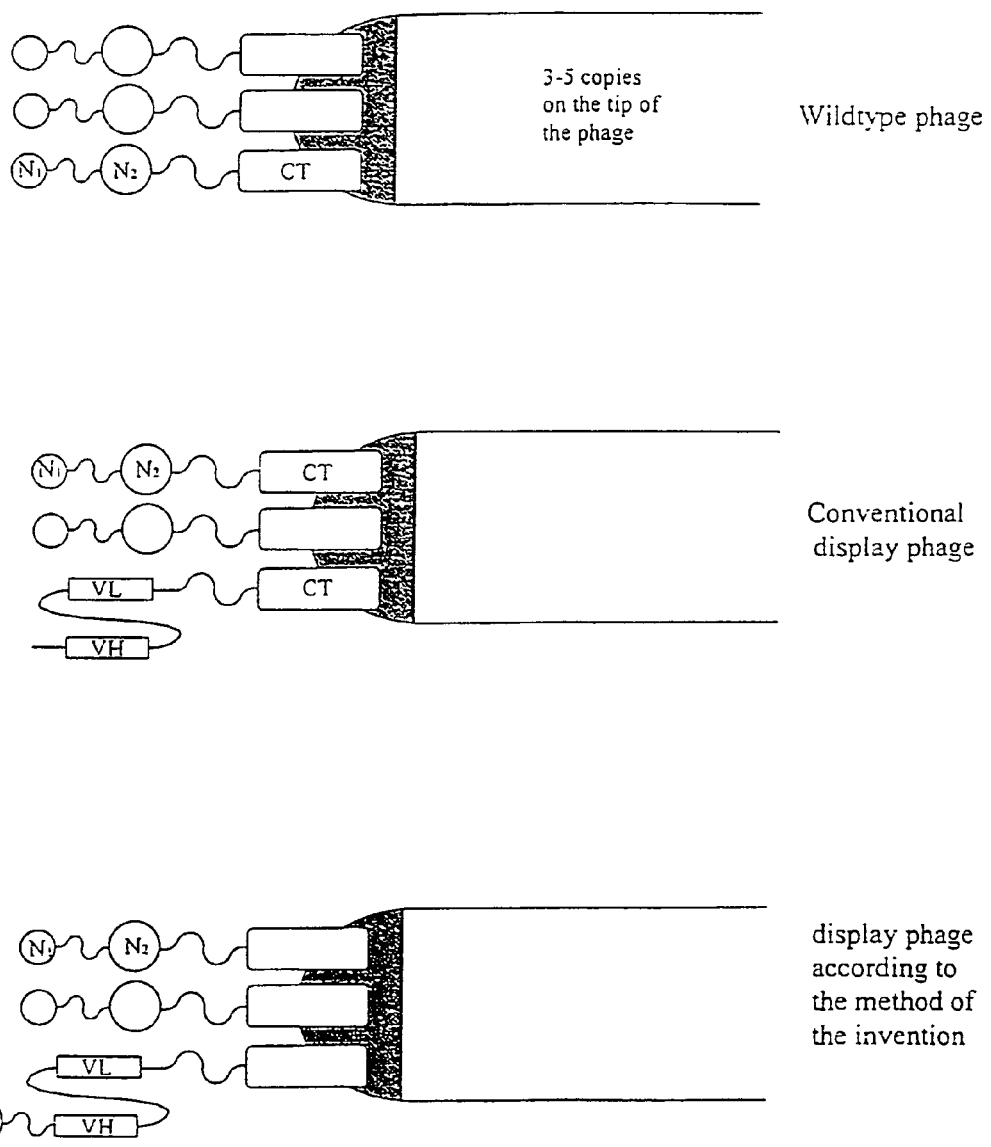

FIG. 11: Structural comparison between wildtype phage, conventional phage display and phage display according to the method of the invention.

Figure 12:
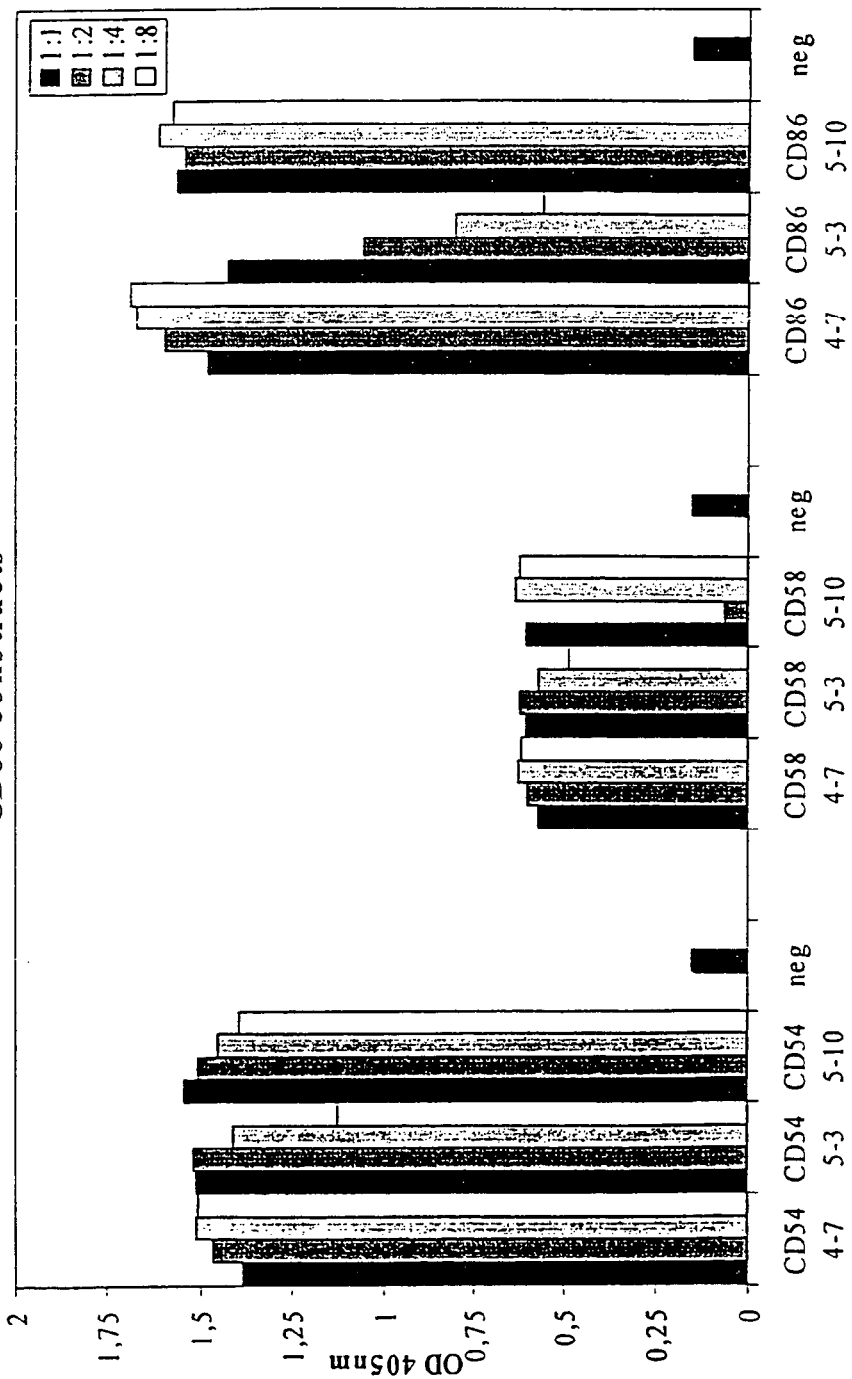

FIG. 12: ELISA-analysis of cell-culture supernatants of different anti 17-1A-CD54-, anti 17-1A-CD58- and anti 17-1A-CD86-scFv constructs with varying anti 17-1A specificities (4-7, 5-3, 5-10) obtained by the method of the invention. Cell-culture supernatant of transfected CHO-cells subjected to one step of gene amplification (20 nM MTX, see Example 10) was incubated in several dilutions in 96-well U bottom ELISA plates with immobilized 17-1A antigen (Coating conditions: see Example 8) Specific detection of the different constructs bound to immobilized 17-1A antigen was performed by using an anti-CD54-(Immunotech Hamburg, Cat. no 0544), an anti-CD58-(Immunotech, Hamburg Cat. no. 0861), or an anti-CD86-(R&D Systems, Cat. No. MB141) antibody (diluted 1:1000), followed by a polyclonal peroxidase-conjugated Goat Anti-Mouse IgG-antibody (Fc-specific) diluted 1:5000, respectively. The ELISA was finally developed by adding an ABTS substrate solution as described in Example 8. For negative controls, the plates were incubated with PBS instead of bifunctional antibody constructs. The OD-values were measured at 405 nm using an ELISA-reader.

Tab. 1: Primer sets for the amplification of the $V_H$- and VK-DNA-fragments (5' to 3')

The following Examples illustrate the invention:

Example 1

CD80-M79scFv Constructs 1.1 CD80-M79 scFv ($V_L/V_H$) Construct with Short $(Gly_4Ser_1)_1$ Linker A protein was constructed that consists of the single-chain Fv fragment (scFv) of the murine anti 17-1A antibody M79 and the extracellular part of the human costimulatory protein CD80 (B7-1) connected by a $(Gly_4Ser_1)_1$ linker (FIG. 1.1). The M79 antibody was obtained as described by Göttlinger (1986) Int. J. Cancer: 38, 47-53. The M79 scFv fragment was cloned as described by Mack. Proc. Natl. Acad. Sci. U.S.A. 92 (1995) 7021-7025. The complete plasmid was cloned in several steps. First a poly-linker designated CTI was inserted into the Bluescript KS vector (GenBank® accession number X52327) using the restriction enzyme cleavage sites XbaI and SalI (Boehringer Mannheim). The introduction of the polylinker CTI provided additional cleavage sites as well as the sequence encoding the $(Gly_4Ser_1)_1$, linker a six-amino acid histidine tag and a stop codon as shown in FIG. 1.2. The vector Bluescript KS+CTI was prepared by cleavage with the restriction enzymes EcoRV and XmaI (Boehringer Mannheim and New England Biolabs) in order to ligate it (T4 DNA, Ligase Boehringer Mannheim) with the M79 scFv fragment cleaved by EcoRV and BspEI (New England Biolabs). The resulting vector Bluescript KS+CTI+M79 scFv again was cleaved with EcoRI (Boehringer Mannheim) and BspEI in order to insert the CD80 DNA-fragment which was previously prepared using the same enzymes. Prior to subcloning, the CD80 fragment was obtained by polymerase chain reaction (PCR) using specific oligonucleotide primers complementary to the 5' and 3' ends of the nucleotide sequence encoding the extracellular part of CD80 (Freeman G. J et. al. J. Immunol. 143, (1989) 2714-2722.). These primers also introduced an EcoRI and BspEI cleavage site (5'CD80 Primer (SEQ ID NO: 1): 5'GCA GAA TTC ACC ATG GGC CAC ACA CGG AGG CAG 3'; 3'CD80 Primer (SEQ ID NO: 2): 5'TGG TCC GGA GTT ATC AGG AAA ATG CTC TTG CTT G 3') The cDNA template used for this PCR was prepared by reverse transcription of the total RNA prepared from the Burkitt-lymphoma cell line Raji according to standard procedures (Sambrook, Molecular Cloning; A Laboratory Manual, $2^{nd}$ Edition, Cold Spring Harbour Laboratory Press, cold Spring Habour, N.Y. (1989)).

The CD80 costimulatory protein belongs to the Ig superfamily. It is a heavily glycosylated protein of 262 amino acids. A more detailed description was published by Freeman G. J et. al. J. Immunol. 143. (1989) 2714-2722.

In the last step, the whole CD80-M79 scFv ($V_L/V_H$) DNA fragment (FIG. 1.3.1.) was isolated by cleaving the vector Bluescript KS+CTI+CD80-M79 scFv ($V_L/V_H$) with EcoRI and SalI (Boehringer Mannheim) and subsequently introduced into the eukaryontic expression vector pEF-DHFR described in Mack et. al. Proc. Natl. Sci. U.S.A. 92 (1995) 7021-7025 containing the dihydrofolatereductase gene as selection marker. The final plasmid was linearized with the restriction enzyme NdeI (Boehringer Mannheim) and transfected into CHO cells by electroporation. The electroporation conditions were 260V/960 µFD using a BioRad Gene Pulser™. Stable expression was performed in DHFR deficient CHO-cells as described by Kaufmann R. J. (1990) Methods Enzymol. 185, 537-566. The cells were grown for selection in nucleoside free α-MEM medium supplemented with 10% dialysed FCS and 2 mM L-glutamine. For production of the bifunctional CD80-M79 scFv ($V_L/V_H$) construct, cells were grown in rollerbottles (Falcon) for 7 days in 300 ml culture medium. The protein was purified via its His-tag attached to the C-terminus (see FIG. 1.1.) by using a Ni-NTA-column (Mack et. al., Proc. Natl. Acad. Sci. U.S.A. 92 (1995) 7021-7025). To analyse the binding properties different ELISA assay were performed.

1.1.1 ELISA with Cell Culture Supernatant Using Anti-His-tag Detection

Binding to the 17-1A-antigen was analysed using soluble 17-1A-antigen obtained as described (Mack, Proc. Natl. Acad. Sci. U.S.A. 92 (1995) 7021-7025) by stable expression in CHO-cells of the DNA encoding the first 264 amino acids of the 17-1A antigen also known as GA 733-2 (Szala, Proc. Natl. Acad. Sci. U.S.A. 87 (1990) 3542-3546) followed by a stop codon. The antigen was immobilized on 96 well U bottom ELISA plates (nunc maxisorb) at a concentration of 50 µg/ml phosphat buffered saline PBS. Coating was carried out at 4° C. for 12 hours with 50 µl followed by washing once with (PBS) 0.05% Tween. The ELISA was then blocked for 1 hour with PBS/3% bovine serum albumin (BSA) and washed again once. Now the cell-culture supernatant was added undiluted and at several dilutions and incubated for 2 hours. As detection system a murine IgG1 anti His-tag antibody (dianova, Hamburg) diluted 1:200 and a peroxidase conjugated polyclonal goat anti mouse IgG (Fc) (dianova, Hamburg) antibody were applied sequentially. The ELISA was developed by adding ABTS-substrate solution (2'2 Azino-bis (3-Ethlbenzthiazoline-6-Sulfonic Acid), SIGMA A-1888, Steinheim) as described in Example 8. The result was measured by an ELISA-Reader at OD 405 nm; results are shown in FIG. 1.4. Obviously no binding activity could be measured. As negative controls, the plates were incubated with PBS instead of antibody constructs. As positive control served the anti-17-1A/anti-CD3 bispecific-single-chain antibody described previously (Mack, Proc. Natl. Acad. Sci. U.S.A. 92 (1995) 7021-7025).

1.1.2 ELISA with Cell Culture Supernatant Using Anti-CD80 Detection

Immobilization of 17-1A-antigen, blocking and the incubation of cell culture supernatants was performed as described above. Detection was carried out with a murine IgG1 anti-CD80-antibody diluted 1:1000 (dianova, Hamburg) followed by a peroxidase conjugated polyclonal goat anti-mouse IgG (Fc)-antibody diluted 1:5000 (dianova, Hamburg). The ELISA was developed with ABTS-substrat solution and OD-values were measured as described above, however, again no 17-1A-binding activity could be detected. As positive control, the anti-17-1A/anti-CD3 bispecific-single-chain antibody (Mack, Proc. Natl. Acad. Sci. U.S.A. 92 (1995) 7021-7025) was used and detected with the described anti-His-tag antibody. Results are shown in FIG. 1.5.

1.1.3 ELISA-analysis of Purified Recombinant CD80-M79scFv-construct

As the ELISAs with cell-culture supernatants detecting specific antigen binding were all negative, soluble CD80-M79scFv was obtained by protein purification from supernatant of a roller bottle culture (300 ml) in order to exclude the possibility that no recombinant protein was secreted into the supernatant. The purification was carried out using a Nickel-NTA-column as described (Mack, Proc. Natl. Acad. Sci. U.S.A. 92 (1995) 7021-7025). ELISA wells were coated with the protein eluted from the Nickel-NTA-column. Detection of the bifunctional CD80-M79scFv-construct was performed independently of its 17-1A-antigen binding activity by using either an anti His-tag antibody (see Example 1.1.1.) as well as an anti-CD80 antibody (see Example 1.1.2.) in separate experiments followed by an anti-mouse IgG(Fc) antibody, respectively. Development of the ELISA as well as the measurement of the OD-values was carried out as described above. The results are shown in FIG. 1.6., confirming the presence of the CD80-M79scFv-construct in the cell culture supernatant.

1.2 CD80-M79 scFv ($V_H/V_L$) Construct with $(Gly_4Ser_1)_1$ Linker

To change the arrangement of the Ig variable regions within the M79scFv fragment from $V_L/V_H$ to $V_H/V_L$ a two step fusion PCR using oligonucleotide primers 5'$V_H$B5RRV (SEQ ID NO: 3):AGG TGT ACA CTC CGA TAT C(A,C)A (A,G)CT GCA G(G,C)A GTC (A;T)GG, 3'$V_H$GS15, 5'$V_L$GS15, 3'$V_L$BspE1 (for sequences of the three last oligonucleotides see Example 2.1) was performed according to the procedure described by Mack, Proc. Natl. Acad. Sci. U.S.A. 92 (1995) 7021-7025 (see also Example 2.1.) The PCR-fragment encoding the $V_H/V_L$-scFv-fragment was cleaved with the restriction enzymes EcoRV/BspEI and inserted into the vector Bluescript KS+CTI already prepared by cleavage with EcoRV/XmaI (see Example 1.1.). Next, the inverted M79scFv ($V_H/V_L$) fragment was excised with the restriction enzymes BspEI/SalI and introduced into the plasmid pEF-DHFR+CTI+CD80-M79scFv ($V_L/V_H$) using BspEI/SalI thus replacing the M79scFv-$V_L/V_H$ fragment (see FIG. 1.3.2.). Transfection and cell culture procedures were carried out as described above. Analysis of antigen binding was performed using the described 17-1A-ELISA (Example 1.1.2.). However, no 17-1A binding activity of the alternatively arranged CD80-M79scFv-construct could be detected. Results are shown in FIG. 1.7.

1.3 CD80-M79 scFv ($V_H/V_L$) Construct with a Long $(Gly_4Ser_1)_3$ Linker

First, the M79scFv ($V_H/V_L$) fragment was obtained by a two step fusion PCR as described in Example 1.2. The PCR fragment encoding the $V_H/V_L$-scFv-fragment was cleaved with the restriction enzymes EcoRV/BspEI and subcloned into the Bluescript KS+CTI vector cleaved EcoRV/Xmal (see Example 1.1). In a further step a longer Glyin-Serin linker $(Gly_4Ser_1)_3$ consisting of 15 amino acids was introduced. Therefore, another oligonucleotide linker (ACCGS15BAM), which was designed to encode the $(Gly_4Ser_1)_3$ linker and to provide BspEI and BamHI compatible overhangs had to be inserted into the Bluescript KS+CTI+M79 scFv ($V_H/V_L$) (Example 1.2). The nucleotide sequence of the linker is shown in FIG. 1.8.

The plasmid Bluescript KS+CTI+M79 scFv ($V_H/V_L$) including the coding sequence of the $(Gly_4Ser_3)_3$ linker was cleaved with BspEI and SalI and the resulting DNA-fragment $(Gly_4Ser_1)_3$+M79scFv ($V_H/V_L$) was inserted into the BspEI/SalI-cleaved vector pEF-DHFR that contains the CD80-coding fragment (Example 1.1) thus replacing the M79scFv ($V_L/V_H$) fragment together with the short $(Gly_4Ser_1)_1$ linker (see FIG. 1.3.3). For transfection and cell culture procedure see Example 1.1. Antigen specific binding was analysed by 17-1A ELISA as described above (Example 1.1.1) and detection of functional recombinant protein in the cell-culture supernatant was performed with an anti His-tag antibody followed by an anti mouse IgG (Fc) antibody (compare Example 1.1.1). The anti-17-1A/anti-CD3 bispecific-single-chain antibody (Mack, Proc. Natl. Acad. Sci. U.S.A. 92 (1995) 7021-7025) served as positive control. Development of the ELISA and measurement of the OD values was carried out as described above (Example 1.1.1). However, no antigen binding was detectable. Results are shown in FIG. 1.9.

Example 2

CD80-M74 scFv Construct with Either Short $(Gly_4Ser_1)_1$ or Long $(Gly_4Ser_1)_3$ Linker as well as $(V_H/V_L)$ or $(V_L/V_H)$-domain Arrangement A protein was constructed that consists of the single-chain Fv fragment (scFv) of the anti 17-1A antibody M74 and the costimulatory protein CD80 connected by a $(Gly_4Ser_1)$ linker (FIG. 1.1). The M74 antibody was obtained as described by Göttlinger (1986) Int. J. Cancer: 38, 47-53. $V_L$ and $V_H$ of M74 were cloned from the total RNA of the corresponding hybridoma cell line as described by Orlandi (1989) Proc. Natl. Acad. Sci. USA 86, 3833-3837 and sequenced. The plasmids containing $V_L$ and $V_H$ of the M74 antibody respectively were used as templates for a two-step fusions-PCR resulting in M74 scFv-fragments with either the domain arrangement $V_L/V_H$ or the alternative arrangement $V_H/V_L$. Regarding the $V_L/V_H$ arrangement, the primers for M74 $V_L$ were 5'$V_L$B5RRV (SEQ ID NO:4) (5'AGG TGT ACA CTC CGA TAT CCA GCT GAC CCA GTC TCC A3') and 3'$V_L$GS15 (SE ID NO:5) (5'GGA GCC GCC GCC GCC AGA ACC ACC ACC ACC TTT GAT CTC GAG CTT GGT CCC3') for M74 $V_H$ 5'M74$V_H$GS15 (SEQ ID NO: 6) (5'GGC GGC GGC GGC TCC GGT GGT GGT GGT TCT CAG GT(GC) (AC) A(AG) CTG CAG (GC)AG TC(AT) GGA CCT GAG CTG GTG AAG CCT GGG GCT TCA GTG AAG ATT TCC TGC 3') and 3'$V_H$BspEI (SEQ ID NO: 7) (5'AAT CCG GAG GAG ACG GTG ACC GTG GTC CCT TGG CCC CAG3'). Regarding the $V_H/V_L$-arrangement the primers for M74 $V_H$ were 5'M74$V_H$EcoRV (SEQ ID NO: 8) (5'TCC GAT ATC (AC)A(AG) CTG CAG (GC)AG TC(AT) GGA CCT GAG CTG GTG AAG CCT GGG GCT TCA GTG AAG ATT TCC TGC 3') and 3'$V_H$GS15 (SEQ ID NO: 9) (5'GGA GCC GCC GCC GCC AGA ACC ACC ACC ACC TGA GGA GAC GGT GAC CGT GGT CCC TTG GCC CCA G 3'), for M74 VL 5'$V_L$GS15 (SEQ ID NO: 10) (5'GGC GGC GGC GGC TCC GGT GGT GGT GGT TCT GAC ATT CAG CTG ACC CAG TCT CCA3') and 3'VLBspEI (SEQ ID NO: 11) (5'AAT CCG GAT TTG ATC TCG AGC TTG GTC CC3'). In the first PCR step the corresponding $V_H$-and-$V_L$ fragments were obtained using the following PCR-program: denaturation at 94° C. for 5 min., annealing at 37° C. for 2 min., elongation at 72° C. for 1 min. for the first cycle; denaturation at 94° C. for 1 min., annealing at 37° C. for 2 min., elongation at 72° C. for 1 min. for 6 cycles; denaturation at 94° C. for 1 min., annealing at 55° C. for 1 min., elongation at 72° C. for 45 sec and 18 cycles; terminal extension at 72° C. for 2 min.).

The purified PCR-fragments of $V_H$ and $V_L$ were then used for the second step of the fusion PCR using the following primers for M74 scFv $V_L/V_H$: 5'$V_L$B5RRV and 3'$V_H$BspEI, as well as 5'M74$V_H$EcoRV and 3'$V_L$BspEI for M74 scFv $V_H/V_L$. The following PCR-program was used: denaturation at 94° C. for 5 min. once; denaturation at 94° C. for 1 min., annealing at 55° C. for 1 min., elongation at 72° C. for 1:30 min. and 8 cycles; terminal extension at 72° C. for 2 min.). The next step was to clone both M74 scFv sequences into the plasmid Bluescript KS+CTI (see Example 1) by cleaving the fragments with EcoRV/BspEI and the vector with EcoRV/XmaI. To obtain constructs with different linker length, the following strategy was used:

For generating the CD80-M74scFv-construct with the $V_H/V_L$- and the $V_L/V_H$-arrangement respectively and a short $(Gly_4Ser_1)_1$ linker, the M74 scFv fragment $(V_H/V_L)$ as well as the M74 scFv fragment $(V_L/V_H)$ were excised from Bluescript KS+CTI respectively and each inserted into the vector pEF-DHFR+CTI+CD80-M79scFv$(V_L/V_H)$ (see Example 1.1) using the restriction enzymes BspEI and SalI (see FIGS. 1.3.4 and 1.3.5). For the transfection in CHO-cells and the cell-culture conditions see Example 1.1.

For generating the CD80-M74 scFv-construct with the $V_H/V_L$- and the $V_L/V_H$-arrangement respectively, each containing a long $(Gly_4Ser_1)_3$ linker, the M74 scFv fragments were excised from the vector Bluescript KS+CTI as described above and introduced into the plasmid Bluescript KS+CTI+M79scFv $(V_H/V_L)$ including the long linker (see Example 1.3) by cleaving vector and fragments with EcoRV and SalI respectively thereby replacing the M79 specificity with M74 $(V_H/V_L)$ or M74 $(V_L/V_H)$. The last step prior to transfection was to introduce M74 $(V_H/V_L)$ or M74 $(V_L/V_H)$ into the pEF-DHFR+CTI+CD80-M79scFv $(V_H/V_L)$ vector respectively using the restriction enzymes BspEI and SalI (see FIGS. 1.3.6 and 1.3.7) thus resulting in plasmids with all the requirements for the expression in CHO-cells of CD80-M74 scFv-constructs either with the $V_H/V_L$- or the $V_L/V_H$-domain arrangement and a long $(Gly_4Ser_1)_3$ linker, respectively. For the transfection in CHO-cells and the cell-culture conditions see Example 1.1. The four different constructs (CD80-$(Gly_4Ser_1)_1$-M74 $(V_H/V_L)$, CD80-$(Gly_4Ser_1)_1$-M74 $(V_L/V_H)$, CD80-$(Gly_4Ser_1)_3$-M74 $(V_H/V_L)$, CD80-$(Gly_4Ser_1)_3$-M74 $(Gly_4Ser_1)_3$-M74 $(V_L/V_H)$) were all tested for binding to the 17-1A-antigen using cell-culture supernatants as well as purified from culture supernatant using Nickel-NTA-columns as described in Example 1.1.1. and 1.1.3 respectively. The ELISA was performed as described and detection was carried out by using either an anti His-tag antibody or an anti CD80 antibody followed by a peroxidase conjugated anti-mouse-IgG (Fc) antibody (see Example 1.1.1) respectively. Despite the fact that recombinant protein could be purified from all four supernatants (data not shown), no binding to the 17-1A-antigen could be detected as shown in FIGS. 2.1 and 2.2.

Example 3

CD80-VD4.5VK8 scFv($V_H/V_L$) Construct with Short $(Gly_4Ser_1)_1$ Linker

In a further Example a human anti-17-1A antibody (VD4.5VK8) selected in vitro by the phage display method from a combinatorial antibody library was chosen to analyse its antigen-binding activity at the C-Terminus of a bifunctional single-chain construct as in Examples 1, 2 and 4 and as illustrated in FIG. 1.1. The $V_H$- and $V_L$-chain of VD4.5VK8 were available in the form of cloned DNA fragments with known nucleotide sequence (FIGS. 3.1 and 3.2) and served as template molecules for PCR using the following primers: for $V_H$: 5'$V_H$1357 (SEQ ID NO: 12) 5'-AGG TGC AGC TGC TCG AGT CTG G-3, and 3'huV$_H$BstEII (SEQ ID NO: 13) 5'-CTG AGG AGA CGG TGA CC'-3; for VL: 5'VK3 (SEQ ID NO: 14) GAG CCG CAC GAG CCC GAG CTC GTG (AT)TG AC(AG) CAG TCT CC-3', and 3'huVkBsiWI/SpeI (SEQ ID NO: 15) 5'-GAA GAC ACT AGT TGC AGC CAC CGT ACG TTT (AG)AT-3'). The $V_H$-respectively $V_L$-chains were introduced into a newly constructed vector designated pComb3H5BHis and described in Example 5. VD4.5VK8 VH was subcloned with XhoI and Bst EII, VD4.5VK8 $V_L$ with SacI and SpeI resulting in the plasmid: pComb3H5BHis+VD4.5VK8 $V_H+V_L$. By using the pComb3H5BHis-vector a fusion PCR was no longer necessary to obtain a scFv-antibody fragment with the domain arrangement $V_H/V_L$.

To analyse the 17-1A-binding activity of the VD4.5VK8 scFv-fragment the N2 fragment (see Example 5) was excised by the restriction enzymes XhoI and SalI. The compatible vector ends were religated; the ligation product was transformed into E. coli XI 1 Blue and periplasmatic protein expression was induced by adding IPTG.

Periplasma preparation was carried out and the resulting sample was directly used for the ELISA-based analysis of 17-1A antigen binding activity as described in Example 5. The wells were coated with soluble 17-1A and bound scFv fragments were detected with a murine anti His-tag antibody diluted 1:200 followed by an anti-mouse IgG (Fc) antibody (see Example 1.1.1) diluted 1:5000. Development of the ELISA and measurement of the OD-values was performed as described in Example 1.1.1. As positive control anti 17-1A antibody clone 3-5 obtained by the method of the invention was used (see Example 6). The results are shown in FIG. 3.3 and reveal significant binding of the free monovalent VD4.5.VK8 scFv-fragment to immobilized 17-1A antigen. The next step in generating the bifunctional CD80-VD4.5VK8-scFv-construct was to cleave the plasmid designated Bluescript KS+CTI+L-F-NS3 Frame, deleted of the Bluescript-derived NotI-site and containing an extended polylinker (for the sequence see FIG. 3.4), by the enzymes EcoRI and NotI to subclone the EcoRI/NotI VD4.5VK8 fragment from vector pComb3H5BHis+VD4.5VK8 $V_H+V_L$ described above. As the last step in generating the bifunctional CD80-VD4.5VK8-scFv-construct, the VD4.5VK8-scFv-fragment was excised from the vector Bluescript KS+CTI+L+F+NS3 Frame using the restriction enzymes BspEI and SalI and subcloned into the plasmid pEF-DHFR+CTI+CD80-M79scFv $(V_L/V_H)$ (see Examples 1.1 and 1.2) cleaved with the same enzymes and thereby replacing the M79 scFv fragment by that of the human antibody VD4.5VK8 (see FIG. 1.3.8) Transfection into CHO-cells and cell-culture procedures were performed as described in Example 1.1.1. The 17-1A-antigen-binding activity was analysed by ELISA (FIGS. 8.3 and 8.4) and flowcytometry (FIGS. 9.1 and 9.2) described in detail in Examples 8 and 9; however, no binding to the 17-1A-antigen could be detected by either method.

Example 4

CD80-MACHscFv Antibody Construct

Another murine anti-17-1A-antibody (MACH) obtained by the method described by Göttlinger (1986) Int. J. Cancer: 38, 47-53., was analysed with respect to the antigen binding activity of its scFv-fragment at the C-terminus of a bifunctional single-chain construct. The corresponding immunoglobulin variable regions $V_L$ and $V_H$ were cloned by RT-PCR according to Orlandi, (1989) Proc. Natl. Acad. Sci. USA: 86, 3833-3837 from the total RNA prepared from the hybridoma cell line and subsequently expressed in mammalian cells as chimeric antibody of the human IgG1$_{kappa}$-Isotype according to Orlandi (1989) Proc. Natl. Acad. Sci. U.S.A.: 86, 3833-3837. The recombinant antibody proved to bind to the 17-1A-antigen resembling its murine parent antibody as determined by 17-1A-ELISA using the culture supernatants of the transfected and the hybridoma cell line, respectively. Detection of bound antibody was performed with an anti-human- or anti-murine immunoglobulin antibody, respectively. Development of the ELISA and measurement of OD-values was performed as described in Example 8. The results are shown in FIG. 4.

The Vk and Vh domains were cloned into pComb3H5BHis (according to Examples 3 and 5). The murine anti-17-1A-scFv-fragment was introduced into plasmid the pEF-DHFR+CTI+CD80-VD4.5VK8 (see Example 3) using the restriction enzymes BspEI and NotI, thus replacing the 17-1A-specific VD4.5VK8scFv fragment (FIG. 1.3.9). The obtained expression plasmid was then transfected into CHO cells as described in Example 1.1. The 17-1A binding activity on was analysed by ELISA (FIGS. 8.3 and 8.4) and flowcytometry (FIGS. 9.1 and 9.2) described in detail in Examples 8 and 9; however, no binding to the 17-1A antigen could be detected by either method.

Example 5

Construction of the Phagmid Vector pComb3H5BHis

As a starting point for a phage display vector applicable for the in vitro selection of antibody fragments according to the method of the present invention the vector pComb3H, a derivative of pComb3 (Barbas, Proc. Natl. Acad. Sci. U.S.A. 88 (1991) 7978-7982) was used (for cloning sites see FIG. 5.1), providing:

the bla-gene enabling carbenicilline resistance selection for positive transformation and infection with recombinant phage particles a procaryotic leader sequences for protein excretion of functional antibody fragments into bacterial periplasma an inducible lac-promotor for high protein productivity the coat domain CT of the M13 phage gene III product necessary for anchoring antibody fragments on the surface of filamentous phage (phage display).

For the detection and isolation of proteins expressed in the periplasma of *E. coli*, especially small scFv fragments, a His tag is highly preferable. Therefore the first step was to subclone a DNA-sequence encoding six Histidine residues downstream of the gene III sequence.

The pComb3H vector was cleaved with NheI and a double stranded oligonucleotide with suitable ends was inserted by ligation. The double stranded oligomer encoding the six His residues was created through annealing of the two 5'-phosphorylated primers His6s and His6as (at 94° C., 10 min.; 65° C., 30 min.; 52° C. 30 min. and 30° C. 10 min.).

His6s (SEQ ID NO: 16): 5'-CTAGCCATCACCATCACCATCACA-3'

His6as (SEQ ID NO: 17): 5'-CTAGTGTGATGGTGATGGTGATGG-3'

The primer ends were designed in a way that after fusion with the vector the 3' NheI restriction site was destroyed whereas the 5' NheI cleavage site remained intact. The insert was sequenced to confirm successful cloning and the new vector designated pComb3HHis.

For the purpose of creating scFv-fragments linked to the gene III product with the C-terminus of the light chain variable domain (VK), a totally new multiple cloning site (mcs) had to be subcloned.

The first part of the original mcs of pComb3HHis was excised by SacI-XhoI digestion. The resulting vector fragment was ligated with a double stranded (ds) DNA fragment created by annealing of two 5'-phosphorylated primers (5BFors; 5BForas) giving rise to 5' SacI and 3' XhoI compatible overhangs and destroying the original 5' SacI cleavage site. The annealing of the two primers was carried out at 94° C. 10 min.; 65° C., 30 min.; 52° C. 30 min. and 30° C. 10 min.

Primer sequences:

5Bfors (SEQ ID NO: 18): 5'-GCAGCTGGTCGA-CAAATCCGGAGGTGGTGGATCCGAGGTG-CAGCTGC-3'

5BForas (SEQ ID NO: 19): 5'-TCGAGCAGCTGCAC-CTCGGATCCACCACCTCCGGATTTGTC-GACCAGCTGCAGCT-4'

The insert was sequenced to confirm successful cloning and the new vector designated pComb3HForHis. The original heavy chain cloning stuffer was then excised with XhoI and SpeI, and the resulting vector fragment was ligated with another ds DNA-fragment, again created by annealing of two 5' phosphorylated primers (5BBacks; 5BBackas) under the same conditions used for the annealing of 5BFors and 5BForas.

Primer sequences:

5Bbacks (SEQ ID NO: 20): 5'-TCGAGCCCGGTCAC-CGTCTCCTCAGGTGGTGGTGGTTCTG-GCGGCGGCGGCTCCGGTGGTGGTGGT-TCTGAGCTCGGGA-3'

5Bbackas (SEQ ID NO: 21): 5'-CTAGTCCCGAGCTCA-GAACCACCACCACCGGAGCCGCCGCCGC-CAGAACCACCACCACCTGAGGAGACGGT-GACCGGGC-3'

The whole insert was again sequenced to confirm successful cloning and the new vector designated pComb3HmcsHis (FIG. 5.2).

This vector provides all necessary cloning sites for the cloning of scFv antibody fragments, a procaryotic leader sequence for the transport of the recombinant proteins into the periplasma of *E. coli*, a linkage of scFv-fragments to the CT-domain of the gene III-product of filamentous phage and after removal of the CT-encoding sequence a linkage to a histidine tag. The last and most important step was to introduce a protein reducing the antigen binding activity of position-sensitive antibody fragments and being neutral to insensitive scFv-fragments so that its C-terminus will be fused to the N-terminus of subsequently cloned scFv-antibody-fragments. The M13 gene III domain N2 corresponding to the amino acids 87 to 217 of the gene III-product of bacteriophage fd (Beck, Nucl. Acid. Res. 5 (1978), 4495-4503) was chosen as a suitable protein to be fused to the N-terminus of scFv-fragments; unlike the complete gene III-product, the N2-domain does not mediate phage infectivity. The approximately 400 bp N2-fragment was amplified by PCR (polymerase chain reaction) from VCSM13-phage (available from Stratagene) infected *E. coli* XL1blue (94° C., 4 min.; (94° C., 0.5 min.; 52° C., 1 min.; 72° C., 0.5 min.)×40 cycles; 72° C., 10 min.; 30° C., 1 sec.) using the primers 5' N2 SalI and 3'N2 BspEI.

Primer sequences:

5' N2 SalI (SEQ ID NO: 22): 5'-GGTGTCGACACTAAAC-CTCCTGAGTACGG-3'

3' N2 BspEI (SEQ ID NO: 23): 5'-GCCTCCGGAAGCAT-TGACAGGAGGTTGAGG-3'

This fragment was then subcloned into the pComb3HmcsHis vector using the restriction sites, SalI and BspEI. Correct subcloning was confirmed by DNA-sequencing. The resulting vector was designated pComb3H5BHis.

The sequence of its multiple cloning site is shown in FIG. 5.2. FIG. 5.3 shows a plasmid map of pComb3H5H5BHis with a cloned scFv-antibody-fragment. Unless otherwise stated, the procedures used followed that described in Sambrook, Molecular Cloning, 'A Laboratory Manual', 2nd Edition, Cold Spring Harbour Laboratory Press, Cold Spring Harbour, N.Y. (1989).

Example 6

Construction of the Combinatorial Antibody Library and Phage Display

For immunization 25 µg soluble 17-1A-antigen in 100 µl PBS were mixed with 100 µl incomplete Freuds Adjuvance (IFA) and injected subcutaneously into one mouse. After two and five weeks injection was repeated with the same amount of antigen mixed with the same volume (100 µl) of IFA, respectively. Four weeks after the first injection, successful immunization was analysed by the 17-1A ELISA (see Example 8) using mouse-serum diluted 1:5, 1:50, and 1:500 followed by a peroxidase conjugated anti-mouse Ig-antibody. A strong signal was obtained in all concentrations compared to negative and cross-reactivity controls. Three days after the third injection the murine spleen cells were harvested for the preparation of total RNA according to Chomczynski, Analytical biochemistry 162 (1987) 156-159. A library of murine immunoglobuline (lg) light chain (kappa) variable region (VK) and lg heavy chain variable region ($V_H$) DNA-fragments was constructed by RT-PCR on murine spleen RNA using VK- and $V_H$ specific primer. cDNA was synthesized according to standard protocols (Sambrook, Cold Spring Harbour Laboratory Press 1989, second edition). The primer sets (Table 1) were chosen to give rise to a 5'-XhoI and a 3'-BstEII recognition site for the heavy chain V-fragments and to a 5'-SacI and a 3'-SpeI recognition site for VK. For the PCR-amplification of the $V_H$ DNA-fragments eight different 5'-$V_H$-family specific primers were each combined with one 3'-$V_H$ primer; for the PCR-amplification of the VK-chain fragments seven different 5'-VK-family specific primers were each combined with one 3'-VK primer. Primer sets for the amplification of the $V_H$-and VK-DNA-fragments (5' to 3') are shown in Table 1.

The following PCR program was used for amplification: denaturation at 94° C. for 20 sec.; primer annealing at 52° C. for 50 sec. and primer extension at 72° C. for 60 sec. and 40 cycles, followed by a 10 min. final extension at 72° C.

450 ng of the kappa light chain fragments (SacI-speI digested) were ligated with 1400 ng of the phagmid pComb3H5BHis (SacI-SpeI digested; large fragment). The resulting combinatorial antibody library was then transformed into 300 µl of electrocompetent *Escherichia coli* XL1 Blue cells by electroporation (2.5 kV, 0.2 cm gap cuvette, 25 µFD, 200 Ohm, Biorad gene-pulser) resulting in a library size of 6×10⁸ independent clones. After one hour of phenotype expression, positive transformants were selected for carbenicilline resistance encoded by the pComb3H5BHis vector in 100 ml of liquid super broth (SB)-culture over night. Cells were then harvested by centrifugation and plasmid preparation was carried out using a commercially available plasmid preparation kit (Qiagen). 2800 ng of this plasmid-DNA containing the VK-library (XhoI-BstEII digested; large fragment) were ligated with 900 ng of the heavy chain V-fragments (XhoI-BstEII digested) and again transformed into two 300 µl aliquots of electrocompetent *E. coli* XL1 Blue cells by electroporation (2.5 kV, 0.2 cm gap cuvette, 25 µFD, 200 Ohm) resulting in a total $V_H$-$V_K$ scFv (single chain variable fragment) library size of 4×10⁸ independent clones. After one hour of phenotype expression, positive transformation was selected by carbenicilline resistance. After this adaptation, these clones were infected with an infectious dose of 1×10¹² particles of the helper phage (VCSM13 resulting in the production and secretion of filamentous phages, each of them containing single stranded pComb3H5BHis-DNA encoding a murine scFv-fragment and displaying the corresponding scFv-protein fused to the N2 domain on the phage surface as a translational fusion to phage coat protein III (phage display, see FIG. 6.2).

This phage library carrying the cloned scFv-repertoire was harvested from the culture supernatant by PEG8000/NaCl precipitation and centrifugation, re-dissolved in TBS/1% BSA and incubated with recombinant soluble 17-1A immobilized on 96 well ELISA plates. Soluble 17-1A was prepared as described (Mack, Proc. Natl. Acad. Sci. U.S.A. 92 (1995) 7021-7025. Phage particles expression N2-fused scFv-fragments that did not specifically bind to the target antigen were eliminated by up to ten washing steps with TBS/Tween. Binding entities were eluted by using HCl-Glycine pH 2.2 and after neutralization with 2 M Tris pH 12, the eluat was used for infection of a new uninfected *E. coli* XL1 Blue culture. Cells successfully transduced with a pComb phagmid copy, encoding a murine scFv-fragment, were again selected for carbenicilline resistance and subsequently infected with VCMS13 helper phage to start the second round of antibody display and in vitro selection. After five rounds of phage-production and subsequent selection for antigen-binding scFv-displaying phages, plasmid DNA from *E. coli* cultures was isolated corresponding to 3, 4 and 5 rounds of panning as well as to the unselected repertoire prior to the first round of panning. For the production of soluble scFv-antibody-fragments that carry the N2-domain at their N-terminus, the DNA fragment encoding the CT-domain of the gene III-product was excised from the plasmids (SpeI/NheI), thus destroying the translational fusion anchoring the scFv-fragment to the phage surface. After religation this pool of plasmid DNA was transformed into 100 µl heat shock competent *E. coli* XL1 Blue cells and plated on Carbenicilline LB-Agar. Single colonies were grown in 10 ml LB-Carbenicilline-cultures/20 mM MgCl₂ and scFv-expression was induced after six hours by adding Isopropyl-β-D-thiogalactosid (IPTG) to a final concentration of 1 mM. This in vitro selection procedure as well as the periplasmic expression of soluble antibody fragments was carried out according to Burton, Proc. Natl. Acad. Sci. USA 88 (1991), 10134-10137. These cells were harvested after 20 hours by centrifugation and through four rounds of freezing at –70° C. and thawing at 37° C. the outer membrane of the bacteria was destroyed by temperature shock so that the soluble periplasmatic proteins including the N2-scFv fusion-proteins were released into solution. After elimination of intact cells and cell-debris by centrifugation, the supernatant was tested by ELISA for 17-1A-binding N2-scFv-fusion-proteins. Detection of N2-scFv-fragments bound to immobilized soluble 17-1A antigen was carried out using an anti-His-tag antibody (1 µg/ml PBS) detected with horse radish peroxidase conjugated polyclonal anti mouse antibody (1 µg/ml PBS). The signal was developed by adding ABTS substrate solution, as described in Example 8, and detected at a wavelength of 405 nm. In contrast to clones prior to antigen selection many clones obtained after 3, 4 and 5 rounds of panning showed 17-1A-binding activity as shown in FIG. 6.2.

The DNA-sequence of the $V_H$- and $V_K$-regions of some positive clones (3-1; 3-5; 3-8; 4-1; 4-4; 4-7; 5-3; 5-10 and 5-13) was determined but none of the clones turned out to have identical $V_H$ and VK DNA-sequence combinations (FIGS. 6.3-6.10 and 7). Unless otherwise stated, the procedures used followed that described in Sambrook, Molecular Cloning, 'A Laboratory Manual', 2nd Edition, Cold Spring Harbour Laboratory Press, Cold Spring Harbour, N.Y. (1989).

Example 7

Cloning of Bifunctional CD80-anti-17-1A Single-chain Constructs by Using the scFv-antibody-fragments Generated by the Method of the Present Invention The following nine 17-1A-specific scFv constructs obtained by the procedure described in Example 6
17-1A 3-1 in p-Comb3H-5B-His
17-1A 3-5 in p-Comb3H-5B-His
17-1A 3-5 in p-Comb3H-5B-His
17-1A 4-1 in p-Comb3H-5B-His
17-1A 4-4 in p-Comb3H-5B-His
17-1A 4-7 in p-Comb3H-5B-His
17-1A 5-3 in p-Comb3H-5B-His
17-1A 5-10-in p-Comb3H-5B-His
17-1A 5-13 in p-Comb3H-5B-His were subcloned into the vector pEF-DHFR for stable expression in CHO-cells. In this step the N2-domain was replaced by the two extracellular domains of human CD80 (=B7-1). For this purpose the vector pEF-DHFR+CTI+CD80+scFv VD4.5VK8 described in Example 3 was cleaved the same way as the fragments derived from pComb3H5BHis clones 3-1 to 5-13 using the restriction enzymes BspEI and NotI according to standard procedures (Sambrook, Molecular Cloning; A Laboratory Manual, Second Edition, Cold Spring Harbour Laboratory Press, Cold Spring Harbour, N.Y. (1989)).

Both, vector and fragments were isolated on a 1% agarose gel, the specific bands were eluted using a commercial gel elution kit (Qiagen). After ligation DNA was transformed into the *E. coli* strain XL-1 blue by the standard heat shock method (Sambrook, Molecular Cloning; A Laboratory Manual, Second Edition, Cold Spring Harbour Laboratory Press, Cold Spring Harbour, N.Y. (1989)).

Positive clones were detected by PCR-based colony screening with the following primers:
5' B7-1 (SEQ ID NO: 24) 5'-GCA GAA TTC ACC ATG GGC CAC ACA CGG AGG CAG-3'
3' mu VK (SEQ ID NO: 25) 5'-TGG TGC ACT AGT CGT ACG TTT GAT CTC AAG CTT GGT CCC-3'

One clone of each construct was grown to a 200 ml LB culture in the presence of 50 µg/ml ampicillin. Plasmid-DNA was purified with the commercially available Mega Prep kit (Qiagen) and linearized by the restriction enzyme Nde I. Finally these linearized plasmid-DNAs were transfected into dihydrofolate-reductase (DHFR) deficient CHO cells by electroporation at 260 V and 960 µFD as described (Mack, Proc. Natl. Acad. Sci. U.S.A. 92 (1995), 7021-7025).

Primary selection was carried out in nucleoside-free alpha MEM culture medium supplemented with 10% dialysed FCS as described (Kaufmann, Methods Enzymol. 185 (1990), 537-566). The expression of these constructs was increased by gene amplification induced by the addition of the DHFR-inhibitor methotrexate (MTX) to a final concentration of 20 nM as described (Kaufmann, Methods Enzymol, 185 (1990), 537-566).

Example 8

ELISA-analysis of Bifunctional CD80-anti-17-1A-scFv-constructs Produced by the Method of the Present Invention The culture supernatants of these transfected cell-lines derived from primary selection and first amplification step were tested by ELISA. Therefore recombinant soluble 17-1A (Mack, Proc. Natl. Acad. Sci. U.S.A. 92 (1995), 7021-7025) was coated to 96 well U-bottom ELISA plates (Nunc maxisorb) (50 µg/ml 50 µl/well) in phosphate buffered saline (PBS). Coating was performed overnight at 4° C., blocking was performed with 3% bovine serum albumin (BSA) in PBS for one hour at room temperature. Antibody constructs as culture supernatants from primary selection (PS) (FIGS. 8.1 and 8.2) and the first amplification step (1. Amp.) (FIGS. 8.3 and 8.4), respectively, were added and incubated for one hour at room temperature at different dilutions made in PBS containing 1% BSA.

Bound bifunctional antibody constructs were detected by a CD80-specific monoclonal antibody (Immunotech., Cat. No. 1449) diluted 1:1000 in PBS 1% BSA. After three times of washing with PBS 0.05% Tween 20, a polyclonal peroxidase-conjugated Goat Anti-Mouse IgG-antibody (Fc-specific) was added and incubated at room temperature for one hour. After four times of washing with PBS 0.05% Tween 20, the ELISA was finally developed by adding the following substrate solution: 22 mg ABTS (2.2 Azino-bis (3-Ethylbenzthiazoline-6 Sulfonic Acid) Diammonium salt) was dissolved in 10 ml 0,1 M citrat buffer pH 5,1 containing 2,3 mg Sodium perborate tetrahydrate. For negative controls, the plates were incubated with PBS instead of bifunctional antibody constructs. The coloured precipitate was measured at 405 nm using an ELISA-reader.

As shown in FIGS. 8.1 and 8.2, all clones proved to bind to the 17-1-A-antigen with varying binding intensities.

Example 9

Flowcytometry Analysis of Bifunctional CD80-anti-17-1A-scFv-constructs Produced by the Method of the Present Invention The culture supernatants from the first gene amplification step each containing one of the nine 17-1A-specific bifunctional CD80-scFv-constructs (Example 7) were tested on 17-1A-transfected CHO-cells by flow cytometry. These transfected cell-lines were generated by subcloning of a DNA-fragment encoding the complete amino acid sequence of the 17-1-A-antigen also known as GA733-2 (Szala, Proc. Natl. Acad. Sci. U.S.A. 87 (1990), 3542-3546), into the eukaryotic expression vector pEF-DHFR according to standard procedures (Sambrook, Molecular Cloning; A Laboratory Manual, Second Edition, Cold Spring Harbour Laboratory Press, Cold Spring Harbour, N.Y. (1989)); linearization of the resulting plasmid with the restriction enzyme Nde I and subsequent stable transfection into DHFR-deficient CHO cells was performed as described in Example 7. The expression of transmembrane 17-1A was increased by stepwise gene amplification induced by subsequent addition of increasing concentrations of the DHFR-inhibitor Methotrexat (MTX) to a final concentration of 500 nM, with the concentration steps in between being 20 nM and 100 nM (Kaufmann, Methods Enzymol. 185 (1990), 537-566). These cells were tested for membrane expression of 17-1A by flow cytometry using the 17-1A-specific monoclonal antibody M79 (Göttlinger, Int. J. Cancer 38 (1986), 47-53) at a concentration of 10 µg/ml followed by a polyclonal Goat Anti Mouse IgG+IgM (H+L) antibody diluted 1:100 in PBS. As negative control untransfected CHO cells were used whereas the 17-1A-positive human gastric cancer cell-line Kato, obtained from ATCC served as positive control. Results are shown in FIG. 9.2.

Binding of the bifunctional CD80-scFv-constructs produced by the method of the present invention on 17-1A-positive cells was analysed as follows:

For this purpose adherent untransfected and 17-1A-transfected CHO-cells were detached using PBS containing 0,05% Trypsine, respectively. $5 \times 10^5$ cells were incubated for 30 minutes on ice in 50 µl culture supernatant containing the corresponding bifunctional construct undiluted (FIG. 9.1). Bound bifunctional CD80-scFv-constructs were detected by a monoclonal anti-CD80 antibody (Immunotech. Cat. No: 1449) diluted 1:20 in 50 µl PBS. Incubation conditions were the same as above. Bound CD80-antibody was finally detected by a fluorescein conjugated polyclonal Goat Anti-Mouse IgG+IgM (H+L) antibody diluted 1:100 in PBS. Incubation was again carried out for 30 minutes on ice. For the fixation of fluorescein-labeled cells 1% paraformaldehyd in PBS was used.

As first negative control untransfected CHO-cells were used. The second negative control contained 17-1A-transfected cells that were incubated with PBS instead of bifunctional CD80-scFv-constructs. Staining with the monoclonal antibody M79 (Göttlinger, Int. J. Cancer 38 (1986), 47-53) was used as positive control.

Cells were analysed by flow cytometry on a FACS scan (Becton Dickenson). FACS staining and measuring of the fluorescence intensity were performed as described in Current Protocols in Immunology (Coligan, Kruisbeek, Margulies, Shevach and Strober, Wiley-Interscience, 1992)

As shown in FIG. 9.1 all nine bifunctional CD80-scFv-constructs bound to the 17-1A-antigen on the cell surfaced thus confirming the ELISA- results of Example 8.

Example 10

Construction and Binding Analysis of Bifunctional CD54, CD58- and CD86-anti-17-1A Single-chain Constructs Containing scFv-antibody-fragments Generated by the Method of the Invention In order to confirm that specific 17-1A antigen binding of scFv-antibody fragments obtained by the method of the invention does not depend on a particular further N-terminal domain within a bifunctional single chain construct, the extracellular part of CD80 forming the N-terminal region of the recombinant single chain proteins described in Examples 7-9 was replaced by that of CD54, CD58 and CD86, respectively. The construction of the different bifunctional single-chain constructs is described below.

CD54 Single-chain Constructs

The CD54 antigen known as ICAM-1 (Intercellular adhesion molecule-1) belongs to the Ig-superfamily. It is a heavily glycosilated protein which is expressed on many lymphoid cells, e.g. dendritic-cells. A more detailed description was published by Simmons D. et. al. Nature 331 (1987) 624-626. The cDNA template was obtained by reverse transcription of the total RNA prepared from TPA-stimulated HL-60-cells. To amplify the extracellular region of CD54, specific primers for the 5' and 3' end were used. These primers also introduced the restriction cleavage-sites EcoR1 and BspE1 (5' ICAM (SEQ ID NO: 26): CTC GAA TTC ACT ATG GCT CCC AGC AGC CCC CG and 3' ICAM (SEQ ID NO: 27): GAT TCC GGA CTC ATA CCG GGG GGA GAG CAC). The CD54-PCR fragment was cloned into the vector Bluescript KS+CTI+M79scFv (VL/VH) (see Example 1) using the restriction cleavage sites EcoR1 and BspE1, thus resulting in the vector Bluescript KS+CTI+CD54+M79scFv(VL/VH). The CD54-M79scFv (VL/VH) fragment was isolated by cleavage of the vector Bluescript KS+CTI+CD54+M79scFv(VL/VH) with EcoRI and SalI and subsequently introduced into the eukaryontic expression vector pEFDHFR (see Example 1). The resulting plasmid pEFDHFR CD54-M79scFv (VL/VH) was then cleaved with the restriction enzymes NdeI and BspEI in order to subclone the corresponding DNA-fragment (approximately 2 KB) containing the truncated CD54-sequence into the vectors pEFDHFR+CTI+CD80+scFv anti 17-1A 4-7, pEFDHFR+CTI+CD80+scFv anti 17-1A 5-3 and pEHDFR+CTI+CD80+scFv anti 17-1A 5-10 (see Example 7), respectively, thereby replacing CD80 by CD54. The final plasmids were linearized with the restriction enzyme NdeI and transfected into CHO-cells by electroporation (see Example 1). The transfected CHO-cells (pEF-DHFR-CTI-CD54- anti 17-1A 4-7, pEF-DHFR-CTI-CD54- anti 17-1A 5-3 and pEF-DHFR-CTI-CD54- anti 17-1A 5-10) were grown for selection in nucleoside free α-MEN medium supplemented with 10% dialyzed FCS and 2 mM L-glutamine. The expression of these constructs was subsequently increased by gene amplification induced by the addition of the DHFR-inhibitor methotrexate (MTX) to a final concentration of 20 nM as described (Kaufman, Methods Enzymol. 185 (1990), 537-566) Binding of the CD54-single-chain constructs to the 17-1A-antigen was analyzed using recombinant 17-1A-antigen obtained by stable expression in CHO-cells as described (Mack et. al. Proc. Natl. Acad. Sci. 92 (1995) 7021-7025); the corresponding ELISA was performed as described in Example 8 using cell-culture supernatants, except that specific detection was carried out with an anti-human CD54 antibody diluted 1:1000 (Immunotech Hamburg, Cat. no 0544). The colored precipitate was measured at 405 nm using an ELISA-reader. The results shown in FIG. 12 clearly demonstrate that binding of each of the constructed anti 17-1A-CD54 scFv constructs to the 17-1A-antigen could be detected.

CD58 Single-chain Constructs

CD58 also known as LFA-3 (Lymphocyte Function-Associated Antigen) is a protein belonging to the Ig-superfamily and is the counterreceptor of CD2. A more detailed description was published by Wallner B. P. et. al. J. Exp. Med 166 (1987) 923-932). The cDNA template was obtained by reverse transcription of the total RNA prepared from U937 cells. To amplify the extracellular region of CD58 and to introduce the restriction enzyme cleavage sites XbaI and BspE1, specific 5' and 3' primers were used (5'LFA-3 (SEQ ID NO: 28) AA TCT AGA ACC ATG GTT GCT GGG AGC GAC G and 3'LFA-3 (SEQ ID NO: 29) AAG TCC GGA TCT GTG TCT TGA ATG ACC GCT GC). The further cloning and expression procedure was the same as described above for the CD54 constructs except that XbaI instead of EcoRI was used due to an internal EcoRI-site within the CD58-DNA-fragment and a dam-methylase deficient *E. coli*-strain was used in order to prevent blocking of the BspEI site at the 3'-end of the CD58-fragment due to an overlapping dam-site. The finally resulting transfected CHO cells (pEF-DHFR-CTI-CD58-anti 17-1A 4-7, pEF-DHFR-CTI-CD58- anti 17-1A 5-3 and pEF-DHFR-CTI-CD58-anti 17-1A 5-10) were grown for selection in nucleoside free α-MEN medium supplemented with 10% dialyzed FCS and 2 mM L-glutamine. The expression of these constructs was subsequently increased by gene amplification induced by the addition of the DHFR-inhibitor methotrexate (MTX) to a final concentration of 20 nM as described (Kaufman, Methods Enzymol. 185 (1990), 537-566). Binding of the CD58-single-chain constructs to the 17-1A-antigen was analyzed as described above except that the specific detection was carried out with an anti human CD58 antibody diluted 1:1000 (Immunotech, Hamburg Cat. no. 0861). The results shown in FIG. 12 clearly demonstrate that binding of each of the constructed anti 17-1A-CD58 scFv constructs to the 17-1A-antigen could be detected.

CD86 Single-chain Constructs

The CD86 costimulatory protein also known as B7-2 belongs to the Ig superfamily. It is a heavily glycosylated protein of 306 amino acids. A more detailed description was published by Freeman G. J. et. al. Science 262 (1993) 909-911. The cDNA template was obtained by reverse transcription of the total RNA prepared from the Burkitt-Lymphoma cell line Raji. To amplify the extracellular region of CD86 specific 5' and 3' primers (5'B7-2 (SEQ ID NO: 30): 5'AAG TCT AGA AAA TGG ATC CCC AGT GCA CTA TG 3', 3'B7-2 (SEQ ID NO: 31): 5'AAT TCC GGA TGG GGG AGG CTG AGG GTC CTC AAG C '3) were used. These primers also introduce Xba1 and BspE1 cleavage sites which were used to clone the CD86 PCR-fragment into the vector Bluescript KS-CTI-M79scFv (VL/VH) (see Example 1). The further cloning and expression procedure was the same as described above for the CD54-construct except that XbaI instead of EcoRI was used due to an internal EcoRI-site within the CD86-DNA-fragment. The finally resulting transfected CHO cells (pEF-DHFR-CTI-CD86- anti 17-1A 4-7, pEF-DHFR-CTI-CD86-anti 17-1A 5-3 and pEF-DHFR-CTI-CD86- anti 17-1A 5-10) were grown for selection in nucleoside free α-MEN medium supplemented with 10% dialyzed FCS and 2 mM L-glutamine. The expression of these constructs was subsequently increased by gene amplification induced by the addition of the DHFR-inhibitor methotrexate (MTX) to a final concentration of 20 nM as described (Kaufman, Methods Enzymol. 185 (1990), 537-566).

Binding of the CD86-single-chain constructs to the 17-1A-antigen was analyzed as described above except that the specific detection was carried out with an anti-human CD86 antibody diluted 1:1000 (R&D Systems, Cat. No. MB141) The results shown in FIG. 12 clearly demonstrate that binding of each of the constructed anti 17-1A-CD86 scFv constructs to the 17-1A-antigen could be detected.

TABLE 1

Primer sets for the amplification of the VH- and VK-DNA-fragments (5' to 3')

murine V heavy chain:

5' primer (SEQ ID NO:32) MVH1 5'-(GC)AGGTGCAGCTCGAGGAGTCAGGACCT-3'

TABLE 1-continued

Primer sets for the amplification of the VH- and VK-DNA-fragments (5' to 3')

(SEQ ID NO:33) MVH2 5'-GAGGTCCAGCTCGAGCAGTCTGGACCT-3'

(SEQ ID NO:34) MVH3 5'-CAGGTCCAACTCGAGCAGCCTGGGGCT-3'

(SEQ ID NO:35) MVH4 5'-GAGGTTCAGCTCGAGCAGTCTGGGGCA-3'

(SEQ ID NO:36) MVH5 5'-GA(AG)GTGAAGCTCGAGGAGTCTGGAGGA-3'

(SEQ ID NO:37) MVH6 5'-GAGGTGAAGCTTCTCGAGTCTGGAGGT-3'

(SEQ ID NO:38) MVH7 5'-GAAGTGAAGCTCGAGGAGTCTGGGGGA-3'

(SEQ ID NO:39) MVH8 5'-GAGGTTCAGCTCGAGCAGTCTGGAGCT-3'

3' primer (SEQ ID NO: 40)

MUVHBstEII 5'-TGAGGAGACGGTGACCGTGGTCCCTTGGCCCCAG-3' murine V kappa chain:

5' primer (SEQ ID NO:41) MUVK1 5'-CCAGTTCCGAGCTCGTTGTGACTCAGGAATCT-3'

(SEQ ID NO:42) MUVK2 5'-CCAGTTCCGAGCTCGTGTTGACGCAGCCGCCC-3'

(SEQ ID NO:43) MUVK3 5'-CCAGTTCCGAGCTCGTGCTCACCCAGTCTCCA-3'

(SEQ ID NO:44) MUVK4 5'-CCAGTTCCGAGCTCCAGATGACCCAGTCTCCA-3'

(SEQ ID NO:45) MUVK5 5'-CCAGATGTGAGCTCGTGATGACCCAGACTCCA-3'

(SEQ ID NO:46) MUVK6 5'-CCAGATGTGAGCTCGTCATGACCCAGTCTCCA-3'

(SEQ ID NO:47) MUVK7 5'-CCAGTTCCGAGCTCGTGATGACACAGTCTCCA-3'

3' primer (SEQ ID NO: 48)

MUVKHindIII/BsiWI 5'-TGGTGCACTAGTCGTACGTTTGATCTCAAGCTTGGTCCC-3'

The invention claimed is:

1. A method of identifying at least one epitope binding domain capable of binding to a predetermined epitope comprising:
   (a) displaying on the surface of a biological display system a panel of recombinant polypeptides comprised of:
      (1) an N-terminal blocking domain at the N-terminus of said recombinant polypeptides,
      (2) a C-terminal anchoring domain at the C-terminus of said recombinant polypeptides, said C-terminal anchoring domain mediates anchoring of said recombinant polypeptides to the surface of said display system, and
      (3) at least one epitope binding domain positioned between said N-terminal blocking domain and said C-terminal anchoring domain;
   (b) exposing said recombinant polypeptides to said predetermined epitope; and
   (c) identifying a subset of said recombinant polypeptides that comprise an epitope binding domain capable of binding to said predetermined epitope.

2. The method of claim 1, wherein said N-terminal blocking domain and said epitope binding domain are linked by a polypeptide linker.

3. The method of claim 2, wherein said polypeptide linker comprises a plurality of hydrophilic amino acids and connects the C-terminalend of said blocking domain and the N-terminal end of said epitope binding domain.

4. The method of claim 1 or 2, wherein said epitope binding domain is a pair of $V_H$-$V_L$ domain.

5. The method of claim 4, wherein said pair of epitope binding domains are connected by a flexible linker.

6. The method of claim 5. wherein said polypeptide linker comprises a plurality of hydrophilic amino acids and allows for said epitope binding domains to assume a conformation suitable for binding epitope when disposed in aqueous solution.

7. The method of claim 1 wherein said display system is a filamentous phage system, a baculovirus expression system, a ribosome based expression system, a bacteriophage lambda display system or a bacterial surface expression system.

8. The method of claim 7, further comprising, prior to step (a), the further step of:

(a") transfecting bacteria with recombinant vectors encoding said recombinant polypeptides.

9. The method of claim 8, further comprising, prior to step (a"), the further step of:
(a) cloning a panel of nucleic acid molecules encoding epitope binding domains into a vector.

10. The method of claim 9, wherein said panel of nucleic acid molecules is derived from immune competent cells of a mammal, fish or bird.

11. The method of claim 1, wherein said N-terminal blocking domain comprises at least 9 amino acids.

12. The method of claim 11, wherein said N-terminal blocking domain is or is derived from the N2-domain of the gene III product of filamentous phase.

13. The method of claim 1, wherein said C-terminal anchoring domain is or is derived from the C-terminal CT-domain of the gene III product of filamentous phage.

14. The method of claim 1, wherein said recombinant polypeptide is a bifunctional- or a multifunctional polypeptide.

15. The method of claim 1, wherein said N-terminal blocking domain comprises an amino acid sequence that forms an effector domain having a biological activity.

16. The method of claim 15 wherein said effector domain is an enzyme, toxin, receptor, binding site, biosynthetic antibody binding site, growth factor, cell-differentiation factor, lymphokine, cytokine or hormone.

17. The method of claim 16, wherein said receptor comprises a co-stimulatory surface molecule important for T-cell activation, an epitope binding domain or a hormone binding site.

18. The method of claim 17, wherein said co-stimulatory surface molecule is CD80 (B7-1), CD86 (B7-2), CD58 (LFA-3) or CD54 (ICAM-1).

19. The method of claim 15, wherein said effector domain is capable of sequestering an ion or selective binding to a solid support.

20. The method of claim 19 wherein said effector domain capable of sequestering an ion is calmodulin, methallothionein, a fragment thereof, or an amino acid sequence rich in at least one of glutamic acid, aspartic acid, lysine, and arginine.

21. The method of claim 19 wherein said effector domain capable of selective binding to a solid support is a positively or negatively charged amino acid sequence, a cysteine-containing amino acid sequence, streptavidin, or a fragment of *Staphylococcus* protein A.

22. The method of claim 1, further comprising the step of:
(b''') verifying whether said epitope binding domain binds to said predetermined epitope.

23. An isolated epitope binding domain or recombinant polypeptide identified by the method of claim 1, wherein said epitope binding domain or recombinant polypeptide comprises six complementarity determining regions (CDR) from SEQ ID NO: 61, wherein said epitope binding domain or said recombinant polypeptide binds 17-1A.

24. An isolated epitope binding domain or recombinant polypeptide identified by the method of claim 1, wherein said epitope binding domain or recombinant polypeptide comprises the six complementarity determining regions that bind 17 1A (CDR) from SEQ ID No. 75.

25. An isolated polypeptide or antibody comprising at least one epitope binding domain or recombinant polypeptide according to claim 24.

26. The method of claim 1, wherein said epitope binding domain is comprised of at least two domains selected from the group consisting of $V_H$-$V_L$.

27. The method of claim 1, wherein said recombinant polypeptides are bivalent or multivalent.

28. An isolated epitope binding domain or recombinant polypeptide identified by the method of claim 1, wherein said epitope binding domain or recombinant polypeptide comprises six complementarity determining regions from SEQ ID NO: 63, and wherein said epitope binding domain or said recombinant polypeptide binds 17-1A.

29. An isolated epitope binding domain or recombinant polypeptide identified by the method of claim 1, wherein said epitope binding domain or recombinant polypeptide comprises six complementarity determining regions from SEQ ID NO: 65, and wherein said epitope binding domain or said recombinant polypeptide binds 17-1A.

30. An isolated epitope binding domain or recombinant polypeptide identified by the method of claim 1, wherein said epitope binding domain or recombinant polypeptide comprises six complementarity determining regions from SEQ ID NO: 67, and wherein said epitope binding domain or said recombinant polypeptide binds 17-1A.

31. An isolated epitope binding domain or recombinant polypeptide identified by the method of claim 1, wherein said epitope binding domain or recombinant polypeptide comprises six complementarity determining regions from SEQ ID NO: 69, and wherein said epitope binding domain or said recombinant polypeptide binds 17-1A.

32. An isolated epitope binding domain or recombinant polypeptide identified by the method of claim 1, wherein said epitope binding domain or recombinant polypeptide comprises six complementarity determining regions from SEQ ID NO: 71, and wherein said epitope binding domain or said recombinant polypeptide binds 17-1A.

33. An isolated epitope binding domain or recombinant polypeptide identified by the method of claim 1, wherein said epitope binding domain or recombinant polypeptide comprises six complementarity determining regions from SEQ ID NO: 73, and wherein said epitope binding domain or said recombinant polypeptide binds 17-1A.

34. An isolated epitope binding domain or recombinant polypeptide identified by the method of claim 1, wherein said epitope binding domain or recombinant polypeptide comprises six complementarity determining regions from SEQ ID NO: 75, and wherein said epitope binding domain or said recombinant polypeptide binds 17-1A.

35. An isolated epitope binding domain or recombinant polypeptide identified by the method of claim 1, wherein said epitope binding domain or recombinant polypeptide comprises six complementarity determining regions from SEQ ID NO: 77, and wherein said epitope binding domain or said recombinant polypeptide binds 17-1A.

36. A kit comprising:
(a) a panel of recombinant vectors encoding a panel of recombinant polypeptides comprised of:
i. an N-terminal blocking domain at the N-terminus of said recombinant polypeptides;
ii. a C-terminal anchoring domain at the C-terminus of said recombinant polypeptides;
iii. at least one epitope binding domain positioned between said N-terminal blocking domain and said C-terminal anchoring domain; and
(b) a bacterial library transfected with a panel of vectors as defined in (a).

37. An isolated polypeptide or antibody comprising at least one epitope binding domain selected from the group consisting of SEQ ID Nos. 61, 63, 65, 67, 69, 71, 73, 75 and 77, wherein said polypeptide or antibody comprises six complementarity determining regions that bind 17-1A.

38. An isolated polynucleotide that encodes a polypeptide or antibody according to claim 37.

39. A cell transfected with a polynucleotide according to claim 38.

40. A process for the preparation of a polypeptide or antibody comprising cultivating a cell of claim 39 under conditions suitable for the expression of the polypeptide and isolating the polypeptide from the cell culture medium.

41. A pharmaceutical composition comprising a polypeptide or antibody according to claim 37.

42. The pharmaceutical composition according to claim 41, further comprising a pharmaceutically acceptable carrier.

43. A diagnostic composition comprising the polypeptide or antibody of claim 37.

44. The diagnostic composition according to claim 43, further comprising means for detection.

45. An isolated polypeptide or antibody comprising the amino acid sequence of SEQ ID No.75 wherein said SEQ ID No. 75 comprises six complementarity determining regions that bind 17 1A.

46. The polypeptide of claim 45 comprising the amino acid sequence of SEQ ID No. 75.

47. An isolated polypeptide or an antibody comprising the epitope binding domain of SEQ ID No. 75 wherein said isolated polypeptide or antibody comprises six complementarity determining regions that bind 17 1A.

* * * * *